(12) United States Patent
Hara et al.

(10) Patent No.: US 9,970,031 B2
(45) Date of Patent: May 15, 2018

(54) METHOD FOR PRODUCING DICARBOXYLIC ACID

(71) Applicant: AJINOMOTO CO., INC., Tokyo (JP)

(72) Inventors: Yoshihiko Hara, Kanagawa (JP); Keita Fukui, Kanagawa (JP); Daiki Yahagi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days. days.

(21) Appl. No.: 15/630,115

(22) Filed: Jun. 22, 2017

(65) Prior Publication Data

US 2017/0298397 A1    Oct. 19, 2017

Related U.S. Application Data

(63) Continuation of application No. PCT/JP2015/086589, filed on Dec. 25, 2015.

(30) Foreign Application Priority Data

Dec. 26, 2014  (JP) .................. 2014-266560

(51) Int. Cl.
*C12P 7/46*      (2006.01)
*C07K 14/245*    (2006.01)
*C12N 1/20*      (2006.01)
*C12N 15/10*     (2006.01)

(52) U.S. Cl.
CPC .............. *C12P 7/46* (2013.01); *C07K 14/245* (2013.01); *C12N 1/20* (2013.01); *C12N 15/1031* (2013.01); *C12N 15/1082* (2013.01)

(58) Field of Classification Search
CPC ..... C12P 7/46; C07K 14/245; C12N 15/1031; C12N 15/1082; C12N 1/20
See application file for complete search history.

(56) References Cited

U.S. PATENT DOCUMENTS

| | | |
|---|---|---|
| 8,628,941 B2 | 1/2014 | Fukui et al. |
| 8,728,774 B2 | 5/2014 | Rybak et al. |
| 8,753,849 B2 | 6/2014 | Kozlov et al. |
| 8,785,161 B2 | 7/2014 | Rybak et al. |
| 8,969,048 B2 | 3/2015 | Kozlov et al. |
| 9,080,189 B2 | 7/2015 | Fukui et al. |
| 2010/0068774 A1 | 3/2010 | Fukui et al. |
| 2015/0259717 A1 | 9/2015 | Hara et al. |
| 2016/0130618 A1 | 5/2016 | Hara et al. |
| 2016/0222394 A1 | 8/2016 | Yamada et al. |

FOREIGN PATENT DOCUMENTS

| | | |
|---|---|---|
| WO | WO2008/126896 | 10/2008 |
| WO | WO2008/133161 | 11/2008 |
| WO | WO2015/005406 | 1/2015 |

OTHER PUBLICATIONS

Sousa et al., Microbiology 148(Pt5):1291-1303, 2002.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Koita et al., PLOS One 7(8):e43700, pp. 1-9, Aug. 2012.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Fukui, K., et al., "Identification of succinate exporter in Corynebacterium glutamicum and its physiological roles under anaerobic conditions," J. Biotechnol. 2011;154:25-34.
Database UniProt [Online], Feb. 1, 1994, "Inner membrane protein YeeA from *E. coli*;", XP002755507, retrieved from EBI accession No. UNIPROT:P33011 on Mar. 14, 2016, Database accession No. P33011 sequence.
Database UniProt [Online], May 18, 2010, "YeeA from Pantoea ananatis {EMBL:ADD77619.1};", XP002755508, retrieved from EBI accession No. UNIPROT:D4GHV2 on Mar. 15, 2016, Database accession No. D4GHV2, sequence.
Database Geneseq [Online]. Jul. 29, 2004, "Klebsiella pneumoniae polypeptide seqid 8377.", XP002755509, retrieved from EBI accession No. GSP:AB061860 on Mar. 15, 2016, Database accession No. AB061860 sequence.
International Search Report and Written Opinion for PCT Patent App. No. PCT/JP2015/086589 (dated Jun. 24, 2016).
U.S. Appl. No. 15/334,444, Hirano et al., filed Oct. 26, 2016.
U.S. Appl. No. 62/413,030, Mijts et al., filed Oct. 26, 2016.
U.S. Appl. No. 62/417,602, Mijts et al., filed Nov. 4, 2016.
U.S. Appl. No. 62/413,044, Mijts et al., filed Oct. 26, 2016.
U.S. Appl. No. 62/417,609, Mijts et al., filed Nov. 4, 2016.
U.S. Appl. No. 62/413,052, Mijts et al., filed Oct. 26, 2016.
U.S. Appl. No. 62/413,056, Mijts et al., filed Oct. 26, 2016.

* cited by examiner

*Primary Examiner* — Delia Ramirez
(74) *Attorney, Agent, or Firm* — Cermak Nakajima & McGowan LLP; Shelly Guest Cermak

(57) ABSTRACT

A method for producing a dicarboxylic acid is provided. A dicarboxylic acid is produced by culturing a bacterium having a dicarboxylic acid-producing ability, which has been modified so that the expression of one or more of the yeeA gene, ynfM gene, yjjP gene, and yjjB gene is increased, in a medium, and collecting the dicarboxylic acid from the medium.

7 Claims, 1 Drawing Sheet

US 9,970,031 B2

METHOD FOR PRODUCING DICARBOXYLIC ACID

This application is a Continuation of, and claims priority under 35 U.S.C. § 120 to, International Application No. PCT/JP2015/086589, filed Dec. 25, 2015, and claims priority therethrough under 35 U.S.C. § 119 to Japanese Patent Application No. 2014-266560, filed Dec. 26, 2014, the entireties of which are incorporated by reference herein. Also, the Sequence Listing filed electronically herewith is hereby incorporated by reference (File name: 2017-06-22T_US-560_Seq_List; File size: 175 KB; Date recorded: Jun. 22, 2017).

BACKGROUND OF THE INVENTION

Field of the Invention

The present invention relates to a method for producing a dicarboxylic acid using a bacterium.

Brief Description of the Related Art

Dicarboxylic acids such as succinic acid are produced by, for example, fermentation using a microorganism such as bacteria belonging to the family Enterobacteriaceae and coryneform bacteria. Specific known methods for producing a dicarboxylic acid such as succinic acid can include using a microorganism in which the expression of a gene encoding a transporter such as a sucE1 gene (WO2008/126896) and a ybjL gene (WO2008/133161) has been enhanced.

SUMMARY OF THE INVENTION

An aspect of the present invention is to develop a novel technique for improving the ability of a bacterium to produce a dicarboxylic acid and thereby provide a method for efficiently producing a dicarboxylic acid.

The present invention describes the genes yeeA, ynfM, yjjP, and yjjB. These genes encode dicarboxylic acid efflux carriers, and when a bacterium is modified so that the expression of one or more of these genes is increased, it has been found that the ability of the bacteria to produce dicarboxylic acid can be improved.

It is an aspect of the present invention to provide a method for producing a dicarboxylic acid, the method comprising culturing a bacterium having a dicarboxylic acid-producing ability in a medium to produce and accumulate the dicarboxylic acid in the medium; and collecting the dicarboxylic acid from the medium, wherein the bacterium has been modified so to increase the expression of a gene selected from the group consisting of yeeA, ynfM, yjjP, yjjB, and combinations thereof.

It is a further aspect of the present invention to provide the method as described above, wherein the expression of the gene(s) is increased by increasing the copy number of the gene(s), and/or by modifying an expression control sequence of the gene(s).

It is a further aspect of the present invention to provide the method as described above, wherein the yeeA gene is a DNA selected from the group consisting of (A) a DNA encoding a protein comprising the amino acid sequence of SEQ ID NO: 2, 4, or 6; (B) a DNA encoding a protein comprising the amino acid sequence of SEQ ID NO: 2, 4, or 6 but which includes substitution, deletion, insertion, or addition of one or several amino acid residues, and wherein said protein has a dicarboxylic acid-secreting activity; (C) a DNA encoding a protein comprising an amino acid sequence having an identity of 90% or more to the amino acid sequence of SEQ ID NO: 2, 4, or 6, and wherein said protein has a dicarboxylic acid-secreting activity; (D) a DNA comprising the nucleotide sequence of SEQ ID NO: 1, 3, or 5; and (E) a DNA hybridizable under stringent conditions with a sequence complementary to the nucleotide sequence of SEQ ID NO: 1, 3, or 5, or a probe that can be prepared from said complementary sequence, and wherein said DNA encodes a protein having a dicarboxylic acid-secreting activity.

It is a further aspect of the present invention to provide the method as described above, wherein the ynfM gene is a DNA selected from the group consisting of (A) a DNA encoding a protein comprising the amino acid sequence of SEQ ID NO: 8, 10, 12, 14, or 16; (B) a DNA encoding a protein comprising the amino acid sequence of SEQ ID NO: 8, 10, 12, 14, or 16 but which includes substitution, deletion, insertion, or addition of one or several amino acid residues, and wherein said protein has a dicarboxylic acid-secreting activity; (C) a DNA encoding a protein comprising an amino acid sequence having an identity of 90% or more to the amino acid sequence of SEQ ID NO: 8, 10, 12, 14, or 16, and wherein said protein has a dicarboxylic acid-secreting activity; (D) a DNA comprising the nucleotide sequence of SEQ ID NO: 7, 9, 11, 13, or 15; and (E) a DNA hybridizable under stringent conditions with a sequence complementary to the nucleotide sequence of SEQ ID NO: 7, 9, 11, 13, or 15, or a probe that can be prepared from said complementary sequence, and encoding a protein having a dicarboxylic acid-secreting activity.

It is a further aspect of the present invention to provide the method as described above, wherein the yjjP gene is a DNA selected from the group consisting of: (A) a DNA encoding a protein comprising the amino acid sequence of SEQ ID NO: 18 or 20; (B) a DNA encoding a protein comprising the amino acid sequence of SEQ ID NO: 18 or 20, but which includes substitution, deletion, insertion, or addition of one or several amino acid residues, and wherein said protein has a dicarboxylic acid-secreting activity; (C) a DNA encoding a protein comprising an amino acid sequence having an identity of 90% or more to the amino acid sequence of SEQ ID NO: 18 or 20, and wherein said protein has a dicarboxylic acid-secreting activity; (D) a DNA comprising the nucleotide sequence of SEQ ID NO: 17 or 19; and (E) a DNA hybridizable under stringent conditions with a sequence complementary to the nucleotide sequence of SEQ ID NO: 17 or 19, or a probe that can be prepared from said complementary sequence, and encoding a protein having a dicarboxylic acid-secreting activity.

It is a further aspect of the present invention to provide the method as described above, wherein the yjjB gene is a DNA selected from the group consisting of: (A) a DNA encoding a protein comprising the amino acid sequence of SEQ ID NO: 22 or 24; (B) a DNA encoding a protein comprising the amino acid sequence of SEQ ID NO: 22 or 24, but which includes substitution, deletion, insertion, or addition of one or several amino acid residues, and wherein said protein has a dicarboxylic acid-secreting activity; (C) a DNA encoding a protein comprising an amino acid sequence having an identity of 90% or more to the amino acid sequence of SEQ ID NO: 22 or 24, and wherein said protein has a dicarboxylic acid-secreting activity; (D) a DNA comprising the nucleotide sequence of SEQ ID NO: 21 or 23; and (E) a DNA hybridizable under stringent conditions with a sequence complementary to the nucleotide sequence of SEQ ID NO: 21 or 23, or a probe that can be prepared from said complementary sequence, and encoding a protein having a dicarboxylic acid-secreting activity.

It is a further aspect of the present invention to provide the method as described above, wherein the bacterium is a bacterium belonging to the family Enterobacteriaceae, or a coryneform bacterium.

It is a further aspect of the present invention to provide the method as described above, wherein the bacterium belonging to the family Enterobacteriaceae is a *Pantoea* bacterium or an *Enterobacter* bacterium.

It is a further aspect of the present invention to provide the method as described above, wherein the bacterium belonging to the family Enterobacteriaceae is *Pantoea ananatis* or *Enterobacter aerogenes*.

It is a further aspect of the present invention to provide the method as described above, wherein the coryneform bacterium is a *Corynebacterium* bacterium.

It is a further aspect of the present invention to provide the method as described above, wherein the coryneform bacterium is *Corynebacterium glutamicum*.

It is a further aspect of the present invention to provide the method as described above, wherein the dicarboxylic acid is selected from the group consisting of α-ketoglutaric acid, malic acid, fumaric acid, succinic acid, itaconic acid, and combinations thereof.

BRIEF DESCRIPTION OF THE DRAWING

FIG. 1(A) shows growth of the strains.

DETAILED DESCRIPTION OF THE PREFERRED EMBODIMENTS

Figure 1A:
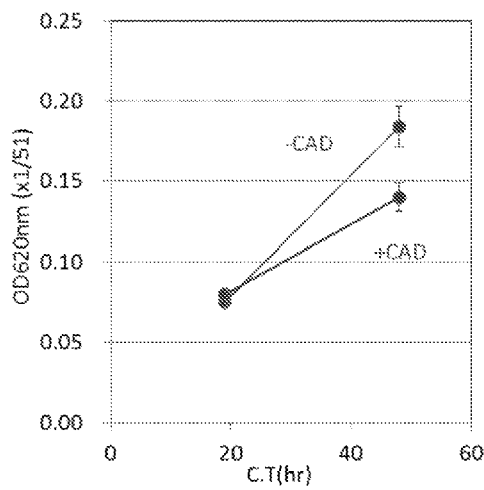
FIGS. 1(A) and (B) show the results of itaconic acid production culture using an itaconic acid-producing bacterium, ITC01 strain (+CAD), and a control strain (−CAD).

The method as described herein is a method for producing a dicarboxylic acid, which can include the steps of culturing a bacterium having a dicarboxylic acid-producing ability in a medium to produce and accumulate the dicarboxylic acid in the medium, and collecting the dicarboxylic acid from the medium, wherein the bacterium has been modified so that the expression of one or more of the yeeA gene, ynfM gene, yjjP gene, and yjjB gene is/are increased. The bacterium used for this method can also be called the "bacterium". The yeeA gene, ynfM gene, yjjP gene, and yjjB gene can also be collectively referred to as "dicarboxylic acid efflux carrier gene".

<1> Bacterium

The bacterium can have a dicarboxylic acid-producing ability, which has been modified so that the expression of a dicarboxylic acid efflux carrier gene is increased.

<1-1> Bacterium Having Dicarboxylic Acid-Producing Ability

A "bacterium having a dicarboxylic acid-producing ability" can refer to a bacterium having an ability to produce and accumulate an objective dicarboxylic acid in a medium in such a degree that the dicarboxylic acid can be collected, when the bacterium is cultured in the medium. The bacterium having a dicarboxylic acid-producing ability can be a bacterium that is able to accumulate an objective dicarboxylic acid in a medium in an amount larger than that obtained with a non-modified strain. The "non-modified strain" can refer to a control strain that has not been modified so that the expression of a dicarboxylic acid efflux carrier gene is increased. Examples of the non-modified strain can include wild-type strains and parent strains of the bacterium. Specific examples of the non-modified strain can include strains exemplified herein, such as *Corynebacterium glutamicum* ATCC 13869 and ATCC 13032 for coryneform bacteria, and *Escherichia coli* K-12 W3110 (ATCC 27325) and MG1655 (ATCC 47076), *Pantoea ananatis* SC17 (FERM BP-11091) and SC17(0) (VKPM B-9246), and *Enterobacter aerogenes* AJ110637 (FERM BP-10955) for Enterobacteriaceae bacteria. The bacterium having a dicarboxylic acid-producing ability may be a bacterium that is able to accumulate an objective dicarboxylic acid in a medium in an amount of 0.5 g/L or more, or 1.0 g/L or more.

Examples of the dicarboxylic acid can include dicarboxylic acids having 3 to 8 carbon atoms ($C_3$-$C_8$ dicarboxylic acids). Specific examples of the dicarboxylic acid can include α-ketoglutaric acid (α-KG, synonymous with 2-oxoglutaric acid), malic acid, fumaric acid, succinic acid, itaconic acid, malonic acid, adipic acid, glutaric acid, pimelic acid, and suberic acid. The bacterium may have an ability to produce only one kind of dicarboxylic acid, or may have an ability to produce two or more kinds of dicarboxylic acids.

The combination of the dicarboxylic acid efflux carrier gene to be overexpressed, and the dicarboxylic acid to be produced is not particularly limited. When the expression of the yeeA gene is enhanced, the dicarboxylic acid may be, for example, α-KG, malic acid, fumaric acid, succinic acid, and itaconic acid. When the expression of the ynfM gene is enhanced, the dicarboxylic acid may be, for example, α-KG, malic acid, fumaric acid, and succinic acid. When the expression of the yjjPB genes is enhanced, the dicarboxylic acid may be, for example, succinic acid.

Examples of the bacterium can include bacteria belonging to the family Enterobacteriaceae and coryneform bacteria.

Examples of bacteria belonging to the family Enterobacteriaceae can include bacteria belonging to the genus *Escherichia, Enterobacter, Pantoea, Klebsiella, Serratia, Erwinia, Photorhabdus, Providencia, Salmonella, Morganella*, or the like. Specifically, bacteria classified into the family Enterobacteriaceae according to the taxonomy used in the NCBI (National Center for Biotechnology Information) database (ncbi.nlm.nih.gov/Taxonomy/Browser/wwwtax.cgi?id=91347) can be used.

The *Escherichia* bacteria are not particularly limited, and examples thereof can include those classified into the genus *Escherichia* according to the taxonomy known to those skilled in the field of microbiology. Examples of the *Escherichia* bacteria can include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Specific examples of *Escherichia coli* strains can include, for example, *Escherichia coli* K-12 strains such as W3110 (ATCC 27325) and MG1655 (ATCC 47076); *Escherichia coli* K5 (ATCC 23506); *Escherichia coli* B strains such as BL21 (DE3); and derivative strains thereof.

The *Enterobacter* bacteria are not particularly limited, and examples can include those classified into the genus *Enterobacter* according to the taxonomy known to those skilled in the field of microbiology. Examples the *Enterobacter* bacterium can include, for example, *Enterobacter agglomerans* and *Enterobacter aerogenes*. Specific examples of *Enterobacter agglomerans* can include, for example, the *Entero-* bacter agglomerans ATCC 12287 strain. Specific examples of *Enterobacter aerogenes* strains can include, for example, the *Enterobacter aerogenes* ATCC 13048, NBRC 12010 (Biotechnol. Bioeng., 2007, Mar. 27; 98(2):340-348), and AJ110637 (FERM BP-10955). Examples of the *Enterobacter* bacteria also can include, for example, the strains described in European Patent Application Laid-open (EP-A) No. 0952221. In addition, *Enterobacter agglomerans* also can include some strains classified as *Pantoea agglomerans*.

The *Pantoea* bacteria are not particularly limited, and examples can include those classified into the genus *Pantoea* according to the taxonomy known to those skilled in the field of microbiology. Examples the *Pantoea* bacteria can include, for example, *Pantoea ananatis, Pantoea stewartii, Pantoea agglomerans*, and *Pantoea citrea*. Specific examples of *Pantoea ananatis* strains can include, for example, the *Pantoea ananatis* LMG20103, AJ13355 (FERM BP-6614), AJ13356 (FERM BP-6615), AJ13601 (FERM BP-7207), SC17 (FERM BP-11091), SC17(0) (VKPM B-9246), and SC17sucA (FERM BP-8646). Some of *Enterobacter* bacteria and *Erwinia* bacteria were reclassified into the genus *Pantoea* (Int. J. Syst. Bacteriol., 39, 337-345 (1989); Int. J. Syst. Bacteriol., 43, 162-173 (1993)). For example, some strains of *Enterobacter agglomerans* were recently reclassified into *Pantoea agglomerans, Pantoea ananatis, Pantoea stewartii*, or the like on the basis of nucleotide sequence analysis of 16S rRNA etc. (Int. J. Syst. Bacteriol., 39, 337-345 (1989)). The *Pantoea* bacteria can include those reclassified into the genus *Pantoea* as described above.

Examples of the *Erwinia* bacteria can include *Erwinia amylovora* and *Erwinia carotovora*. Examples of the *Klebsiella* bacteria can include *Klebsiella planticola*.

Examples of the coryneform bacteria can include bacteria belonging to the genus *Corynebacterium, Brevibacterium, Microbacterium*, or the like.

Specific examples of the coryneform bacteria can include the following species.

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of the coryneform bacteria can include the following strains.

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria can include bacteria that had previously been classified into the genus *Brevibacterium*, but are now united into the genus *Corynebacterium* (Int. J. Syst. Bacteriol., 41, 255 (1991)). Moreover, *Corynebacterium stationis* can includes bacteria that had previously been classified as *Corynebacterium ammoniagenes*, but are now re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

The bacterium may inherently have a dicarboxylic acid-producing ability, or may be a bacterium that is modified so that it has a dicarboxylic acid-producing ability. The bacterium having a dicarboxylic acid-producing ability can be obtained by imparting a dicarboxylic acid-producing ability to such a bacterium as mentioned above, or enhancing a dicarboxylic acid-producing ability of such a bacterium as mentioned above.

Hereafter, specific examples of the dicarboxylic acid-producing bacteria and the method for imparting or enhancing a dicarboxylic acid-producing ability will be described. Such modifications as exemplified below for imparting or enhancing a dicarboxylic acid-producing ability may be independently used, and may be used in an appropriate combination.

Examples of the method for imparting or enhancing a dicarboxylic acid-producing ability can include a method of modifying a bacterium so that the activity of an enzyme that catalyzes a reaction branching off from the biosynthesis pathway of an objective dicarboxylic acid to generate a compound other than the objective dicarboxylic acid is reduced. The phrase "enzyme that catalyzes a reaction branching off from the biosynthesis pathway of an objective dicarboxylic acid to generate a compound other than the objective dicarboxylic acid" also can include an enzyme involved in decomposition of the objective dicarboxylic acid. The activity or activities of one or two or more kinds of enzymes may be reduced. An enzyme activity can be reduced, for example, by reducing the expression of a gene encoding the enzyme, or by disrupting a gene encoding the enzyme as described herein.

For example, succinic acid-producing ability can be imparted or enhanced by reducing the activity or activities of one or more enzymes of the lactic acid biosynthesis system (WO2005/052135, WO2005/116227, U.S. Pat. No. 5,770,435, U.S. Patent Published Application No. 20070054387, WO99/53035, Alam, K. Y. and Clark, D. P., 1989, J. Bacteriol., 171:6213-6217). The same shall apply to the other dicarboxylic acids such as α-KG, malic acid, fumaric acid, and itaconic acid. Examples of the enzymes of the lactic acid biosynthesis system can include lactate dehydrogenase (ldhA). The nucleotide sequence of the ldhA gene of the *Pantoea ananatis* AJ13355 strain is shown as SEQ ID NO: 101, and the amino acid sequence of the protein encoded by this gene is shown as SEQ ID NO: 102. Shown in the parenthesis following the enzyme name is an example of gene encoding the enzyme (the same shall apply to the following descriptions).

The term "lactate dehydrogenase" can refer to a protein having an activity for catalyzing a reaction of generating lactate from pyruvate using NADH or NADPH as an electron donor. This activity may also be referred to as an "lactate dehydrogenase activity". The lactate dehydrogenase is roughly classified into L-lactate dehydrogenase (L-LDH, EC 1.1.1.27) that generates L-lactic acid, and D-lactate dehydrogenase (D-LDH, EC1.1.1.28) that generates D-lactate, and the activity or activities of either or both of them may be reduced. Reduction of the lactate dehydrogenase activity can be confirmed by, for example, measuring the lactate dehydrogenase activity by a known method (L. Kanarek and R. L. Hill, J. Biol. Chem., 239, 4202 (1964)). Specific examples of the method for constructing a mutant strain of Enterobacteriaceae bacterium having a reduced lactate dehydrogenase activity can include the method described in Alam, K. Y, Clark, D. P., 1989, J. Bacteriol., 171, 6213-6217, and so forth.

Succinic acid-producing ability can also be imparted or enhanced by reducing the activity or activities of one or more enzymes of the acetic acid biosynthesis system (U.S. Patent Published Application No. 20070054387, WO2005/052135, WO99/53035, WO2006/031424, WO2005/113745, WO2005/113744). The same shall apply to the other dicarboxylic acids such as α-KG, malic acid, fumaric acid, and itaconic acid. Examples of the enzymes of the acetic acid biosynthesis system can include phosphotransacetylase (pta), acetate kinase (ack), pyruvate oxidase (poxB), acetyl-CoA synthetase (acs), and acetyl-CoA hydrolase.

The term "phosphotransacetylase" can refer to a protein having an activity for catalyzing a reaction of generating CoA and acetyl phosphate from acetyl-CoA and phosphate (EC 2.3.1.8). This activity may also be referred to as "phosphotransacetylase activity". Reduction of the phosphotransacetylase activity can be confirmed by measuring the phosphotransacetylase activity by a known method (Klotzsch, H. R., Meth. Enzymol., 12, 381-386 (1969)).

Succinic acid-producing ability can also be imparted or enhanced by reducing the activity or activities of one or more enzymes of the formic acid biosynthesis system (U.S. Patent Published Application No. 20070054387, WO2005/116227, WO2005/52135, Donnelly, M. I. et al., 1998, Appl. Biochem. Biotechnol., 70-72:187-198). The same shall apply to the other dicarboxylic acids such as α-KG, malic acid, fumaric acid, and itaconic acid. Examples of the enzymes of the formic acid biosynthesis system can include pyruvate formate lyase (pflB, pflD, tdcE).

The term "pyruvate formate lyase" can refer to a protein having an activity for catalyzing a reaction of generating acetyl-CoA and formate from pyruvate and CoA (EC 2.3.1.54). This activity may also be referred to as a "pyruvate formate lyase activity". Reduction of the pyruvate formate lyase activity can be confirmed by measuring the pyruvate formate lyase activity by a known method (Knappe, J. & Blaschkowski, H. P., Meth. Enzymol., 41, 508-518 (1975)).

Succinic acid-producing ability can also be imparted or enhanced by reducing the activity or activities of one or more enzymes of the ethanol biosynthesis system (WO2006/031424). The same shall apply to the other dicarboxylic acids such as α-KG, malic acid, fumaric acid, and itaconic acid. Examples of the enzymes of the ethanol biosynthesis system can include alcohol dehydrogenase (adhE). The nucleotide sequence of the adhE gene of the *Pantoea ananatis* AJ13355 strain is shown as SEQ ID NO: 103, and the amino acid sequence of the protein encoded by this gene is shown as SEQ ID NO: 104.

The term "alcohol dehydrogenase" can refer to a protein having an activity for catalyzing a reaction of generating an alcohol from an aldehyde by using NADH or NADPH as an electron donor (EC 1.1.1.1, EC 1.1.1.2, or EC 1.1.1.71). This activity may also be referred to as an "alcohol dehydrogenase activity". Reduction of the alcohol dehydrogenase activity can be confirmed by, for example, measuring the alcohol dehydrogenase activity by a known method (Lutstorf, U. M., Schurch, P. M. & von Wartburg, J. P., Eur. J. Biochem., 17, 497-508 (1970)). Specific examples of the method for constructing a mutant strain of Enterobacteriaceae bacterium having a reduced alcohol dehydrogenase activity can include the method described in Sanchez, A. M., Bennett, G. N., San, K.-Y., Biotechnol. Prog., 21, 358-365 (2005), and so forth.

Succinic acid-producing ability can also be imparted or enhanced by reducing the activity or activities of one or more enzymes of the 2,3-butanediol biosynthesis system. The same shall apply to the other dicarboxylic acids such as α-KG, malic acid, fumaric acid, and itaconic acid. Examples of the enzymes of the 2,3-butanediol biosynthesis system can include acetolactate synthase (budB, ilvB, ilvG, ilvI), acetolactate decarboxylase (budA), and acetoin reductase (budC, butA). The nucleotide sequences of the budB, budA, and budC genes of the *Pantoea ananatis* AJ13355 strain are shown as SEQ ID NOS: 105, 107, and 109, respectively, and the amino acid sequences of the proteins encoded by these genes are shown as SEQ ID NOS: 106, 108, and 110, respectively.

The term "acetolactate synthase" can refer to a protein having an activity for catalyzing a reaction of generating acetolactate and $CO_2$ from two molecules of pyruvate (EC 2.2.1.6). This activity may also be referred to as an"acetolactate synthase activity". The isozymes AHAS I to III are known for having acetolactate synthase (AHAS) activity, and the activity or activities of any one or more of these isozymes may be reduced. Reduction of the acetolactate synthase activity can be confirmed by, for example, measuring the acetolactate synthase activity by a known method (F. C. Stormer and H. E. Umbarger, Biochem. Biophys. Res. Commun., 17, 5, 587-592 (1964)).

The term "acetolactate decarboxylase" can refer to a protein having an activity for catalyzing a reaction of decarboxylating acetolactate to generate acetoin (EC 4.1.1.5). This activity may also be referred to as an "acetolactate decarboxylase activity". For example, *E. coli* and *Corynebacterium glutamicum* do not have the acetolactate decarboxylase. Reduction of the acetolactate decarboxylase activity can be confirmed by, for example, measuring the acetolactate decarboxylase activity by a known method (Juni E., J. Biol. Chem., 195(2):715-726 (1952)).

The term "acetoin reductase" can refer to a protein having an activity for catalyzing a reaction of generating 2,3-butanediol from acetoin using NADH or NADPH as an electron donor (EC 1.1.1.4). This activity may also be referred to as an "acetoin reductase activity". For example, *E. coli* does not have the acetoin reductase. Reduction of the acetoin reductase activity can be confirmed by, for example, measuring the acetoin reductase activity by a known method (K. Blomqvist et al., J. Bacteriol., 175, 5, 1392-1404 (1993)).

Succinic acid-producing ability can also be imparted or enhanced by reducing the activity or activities of one or more of pyruvate kinase (pykE pykA), glucose PTS (ptsG), ArcA (arcA), IclR (iclR), glutamate dehydrogenase (gdhA), glutamine synthetase (glnA), and glutamate synthase (gltBD) (WO2006/107127, WO2007/07933, Japanese Patent Laid-open (Kokai) No. 2005-168401). The succinic acid-producing ability can also be imparted or enhanced by reducing the activity of succinate dehydrogenase (sdhA). The nucleotide sequence of the sdhA gene of the *Pantoea ananatis* AJ13355 strain is shown as SEQ ID NO: 111, and the amino acid sequence of the protein encoded by the gene is shown as SEQ ID NO: 112.

The term "succinate dehydrogenase" can refer to a protein having an activity for catalyzing a reaction of oxidizing succinic acid using quinone as an electron acceptor (EC 1.3.5.1). This activity may also be referred to as "succinate dehydrogenase". Reduction of the succinate dehydrogenase activity can be confirmed by, for example, measuring the succinate dehydrogenase activity by a known method (Tatsuki Kurokawa and Junshi Sakamoto, Arch. Microbiol., 183:317-324 (2005)).

Malic acid-producing ability can be imparted or enhanced by reducing the activity or activities of one or more of malate dehydrogenase (mdh), malate-quinone oxidoreductase (mqo), and malic enzyme (sfcA, maeB). The nucleotide sequences of mdh, mqo1, mqo2, sfcA, and maeB genes of the *Pantoea ananatis* AJ13355 strain are shown as SEQ ID NOS: 113, 115, 117, 119, and 121, respectively, and the amino acid sequences of the proteins encoded by these genes are shown as SEQ ID NOS: 114, 116, 118, 120, and 122, respectively.

The term "malate-quinone oxidoreductase" can refer to a protein having an activity for catalyzing a reaction of oxidizing malate by using quinone as an electron acceptor. This activity may also be referred to as an "malate-quinone oxidoreductase activity". The malate-quinone oxidoreductase conjugates with the NAD-type malate dehydrogenase to form a cycle of malate and oxaloacetate, and thereby provide net oxidation of NADH. For example, some of the *Pantoea* bacteria have 2 copies of the malate-quinone oxidoreductase gene. In such a case, either one of the genes may be disrupted or the like, or the both genes may be disrupted or the like. Reduction of the malate-quinone oxidoreductase activity can be confirmed by, for example, measuring the malate-quinone oxidoreductase activity by a known method (Hoyt J. C. et al. (1988) Biochim. Biophys. Acta, 14; 966(1):30-5; Mackintosh, C. et al. (1988) Biochem. J., 250, 25-31).

Itaconic acid-producing ability can be imparted or enhanced by reducing the activity or activities of isocitrate dehydrogenase (icd) and/or isocitrate lyase (aceA).

The term "isocitrate lyase" can refer to a protein having an activity for reversibly catalyzing a reaction of generating glyoxylate and succinate from isocitrate (EC 4.1.3.1). This activity may also be referred to as an "isocitrate lyase activity". For example, some of the *Corynebacterium* bacteria have 2 copies of the isocitrate lyase gene. In such a case, either one of the genes may be disrupted or the like, or the both genes may be disrupted or the like. Reduction of the isocitrate lyase activity can be confirmed by, for example, measuring the isocitrate lyase activity by a known method (Hoyt J. C. et al. (1988) Biochim. Biophys. Acta, 14; 966(1):30-5; Mackintosh, C. et al. (1988) Biochem. J., 250, 25-31)

The aceA gene encoding isocitrate lyase typically forms an operon as one of the aceBAK genes. The aceB gene is a gene encoding malate synthase. The aceK gene is a gene encoding isocitrate dehydrogenase kinase/phosphatase. To reduce the isocitrate lyase activity, the entire aceBAK operon may also be disrupted or the like. The nucleotide sequences of the aceB, aceA, and aceK genes of the *Pantoea ananatis* AJ13355 strain are shown as SEQ ID NOS: 123, 125, and 127, respectively, and the amino acid sequences of the proteins encoded by these genes are shown as SEQ ID NOS: 124, 126, and 128, respectively.

Itaconic acid-producing ability can also be imparted or enhanced by increasing the activity of cis-aconitate decarboxylase (CAD). Cis-aconitate decarboxylase (CAD) can refer to a protein having an activity for catalyzing a reaction of decarboxylating cis-aconitate to generate itaconate (EC 4.1.1.6). This activity may also be referred to as a "CAD activity". Increase of CAD activity can be confirmed by, for example, measuring CAD activity by a known method (L. Dwiarti, K. Yamane, H. Yamatani, P. Kahar, M. Okabe. Purification and characterization of cis-aconitic acid decarboxylase from *Aspergillus terreus* TN484-M1. J. of Bioscience and Bioengineering, 94(1), p. 29-33, 2004). Examples of the cis-aconitate decarboxylase gene (CAD gene) can include the CAD gene of *Aspergillus terreus* (Japanese Patent Laid-open (Kokai) No. 2013-051900). The nucleotide sequence of the CAD gene of *Aspergillus terreus* optimized for the codon usage of *E. coli* is shown as SEQ ID NO: 49. In the nucleotide sequence of SEQ ID NO: 49, the coding region corresponds to the positions 91 to 1563. The amino acid sequence of the protein encoded by this gene is shown as SEQ ID NO: 131.

α-KG-producing ability can be imparted or enhanced by reducing the activity of α-ketoglutarate dehydrogenase (sucA, odhA). The nucleotide sequence of the sucA gene of *Pantoea ananatis* AJ13355 strain is shown as SEQ ID NO: 129, and the amino acid sequence of the protein encoded by this gene is shown as SEQ ID NO: 130.

Examples of the method for imparting or enhancing a dicarboxylic acid-producing ability also can include a method of modifying a bacterium so that the activity of an enzyme of the biosynthesis system of the objective dicarboxylic acid is increased. The activity or activities of one or two or more kinds of enzymes may be increased. An enzyme activity can be increased by, for example, enhancing the expression of a gene encoding the enzyme as described herein.

For example, a dicarboxylic acid-producing ability can be imparted or enhanced by increasing the activity or activities of one or more enzymes of an anaplerotic pathway of the TCA cycle. Examples of enzymes of an anaplerotic pathway of the TCA cycle can include pyruvate carboxylase (pyc), phosphoenolpyruvate carboxylase (ppc), phosphoenolpyruvate carboxykinase (pckA), citrate synthase (gltA), and methyl citrate synthase (prpC).

Examples of genes encoding pyruvate carboxylase can include, for example, pyc genes of coryneform bacteria such as *Corynebacterium glutamicum* and *Brevibacterium flavum, Bacillus stearothermophilus, Rhizobium etli*, and yeast such as *Saccharomyces cerevisiae* and *Schizosaccharomyces pombe* (WO2009/072562). Examples of genes encoding phosphoenolpyruvate carboxykinase can include, for example, pckA gene of *Actinobacillus succinogenes* (GenBank Accession No. YP_001343536.1), pckA gene of *Haemophilus influenzae* (GenBank Accession No. YP_248516.1), pckA gene of *Pasteurella multocida* (GenBank Accession No. NP_246481.1), pckA gene of *Mannheimia succiniciproducens* (GenBank Accession No. YP_089485.1), pckA gene of *Yersinia pseudotuberculosis* (GenBank Accession No. YP_072243), pckA gene of *Vibrio cholerae* (GenBank Accession No. ZP_01981004.1), and pckA gene of *Selenomonas ruminantium* (GenBank Accession No. AB016600) (WO2009/072562). Examples of genes encoding phosphoenolpyruvate carboxylase can include, for example, ppc genes of coryneform bacteria such as *Corynebacterium glutamicum* and *Brevibacterium flavum, Escherichia* bacteria such as *Escherichia coli*, and *Rhodopseudomonas palustris*. An enzyme activity can also be increased by, for example, reducing or eliminating feedback inhibition. For example, the activity of phosphoenolpyruvate carboxylase (PEPC) is inhibited by L-malic acid, which is an intermediate product of the succinic acid biosynthesis pathway (Masato Yano and Katsura Izui, Eur. Biochem. FEBS, 247, 74-81, 1997). The inhibition by L-malic acid can be reduced by, for example, introducing a desensitization mutation based on one amino acid substitution into PEPC. Specific example of the desensitization mutation based on one amino acid substitution can include, for example, replacing the 620th amino acid, lysine, with serine, in the PEPC protein of *Escherichia coli* (ibid.).

Examples of dicarboxylic acid-producing bacteria can include the bacteria described in Fermentation Handbook (Kyoritsu Shuppan).

Specific examples of succinic acid-producing bacteria belonging to the family Enterobacteriaceae can include the following strains:

*Escherichia coli* SS373 strain (WO99/06532)
*Escherichia coli* AFP111 strain (WO97/6528)
*Escherichia coli* NZN111 strain (U.S. Pat. No. 6,159,738)
*Escherichia coli* AFP184 strain (WO2005/116227)
*Escherichia coli* SBS100MG strain, SBS110MG strain, SB S440MG strain, SBS550MG strain, and SBS660MG strain (WO2006/031424)
*Enterobacter aerogenes* AJ110637 strain (FERM BP-10955)
*Enterobacter aerogenes* VP-1 strain (J. Biosci. Bioeng., 2004, 97(4):227-32)

Specific examples of succinic acid-producing bacteria belonging to coryneform bacteria can include the following strains:

*Brevibacterium flavum* AB-41 strain (Japanese Patent Laid-open (Kokai) No. 11-113588)
*Brevibacterium flavum* PC-amplified strain of AB-41 strain (Japanese Patent Laid-open (Kokai) No. 11-196888)

*Corynebacterium glutamicum* AJ110655 strain (FERM BP-10951)
*Brevibacterium flavum* MJ233Δldh strain (WO2005/021770)
*Brevibacterium lactofermentum* 2256Δ(ldh,ach,pta,ack) (WO2005/113744)
*Brevibacterium lactofermentum* 2256Δ(ldh,pta,ack,poxB) (WO2005/113745)
*Corynebacterium glutamicum* R ldh-/pCRB-1 PC strain (WO2005/010182)

The genes and proteins used for breeding dicarboxylic acid-producing bacteria may have, for example, the nucleotide sequences and amino acid sequences of known genes and proteins, such as the nucleotide sequences and amino acid sequences exemplified above, respectively. Also, the genes and proteins used for breeding dicarboxylic acid-producing bacteria may be conservative variants of known genes and proteins, such as conservative variants of genes and proteins having the nucleotide sequences and amino acid sequences exemplified above, respectively. Specifically, for example, the genes used for breeding dicarboxylic acid-producing bacteria may each be a gene encoding a protein having an amino acid sequence of a known protein including substitution, deletion, insertion, or addition of one or several amino acid residues at one or several positions. As for conservative variants of genes or proteins, the descriptions concerning conservative variants of the dicarboxylic acid efflux carrier gene and dicarboxylic acid efflux carrier described herein can be applied mutatis mutandis.

<1-2> Enhancement of Expression of Dicarboxylic Acid Efflux Carrier Gene

The bacterium is modified so that the expression of a dicarboxylic acid efflux carrier gene is increased. A dicarboxylic acid-producing ability of a bacterium can be improved by modifying the bacterium so that the expression of a dicarboxylic acid efflux carrier gene is increased.

The bacterium can be obtained by modifying a bacterium having a dicarboxylic acid-producing ability so that the expression of a dicarboxylic acid efflux carrier gene is increased. The bacterium can also be obtained by modifying a bacterium so that the expression of a dicarboxylic acid efflux carrier gene is increased, and then imparting dicarboxylic acid-producing ability or enhancing a dicarboxylic acid-producing ability thereof. The bacterium may also be a bacterium that has acquired a dicarboxylic acid-producing ability by being modified so that the expression of a dicarboxylic acid efflux carrier gene is increased. The modifications for constructing the bacterium can be performed in an arbitrary order.

The dicarboxylic acid efflux carrier gene can be any of the yeeA gene, ynfM gene, yjjP gene, and yjjB gene. Although it has not been previously reported that these genes are dicarboxylic acid efflux carrier genes, it is estimated that these genes are dicarboxylic acid efflux carrier genes on the basis of the results of the experiments shown in the Examples section of this description. The proteins encoded for by the yeeA gene, ynfM gene, yjjP gene, and yjjB gene can also be referred to as the YeeA protein, YnfM protein, YjjP protein, and YjjB protein, respectively. The expression of one kind of dicarboxylic acid efflux carrier gene may be enhanced, or the expression of two or more of the dicarboxylic acid efflux carrier genes may be enhanced. For example, the expression of the yjjP gene and yjjB gene may be enhanced.

<yeeA Gene>

The yeeA gene is a gene encoding a protein presumed to be a conserved inner membrane protein. The yeeA gene of the *Escherichia coli* MG1655 strain can also be referred to as b2008 or ECK2002. The nucleotide sequence of the yeeA gene of the *Escherichia coli* MG1655 strain is shown as SEQ ID NO: 1, and the amino acid sequence of the protein encoded by this gene (GenBank Accession No. NP_416512.1) is shown as SEQ ID NO: 2. The nucleotide sequence of the yeeA gene of the *Pantoea ananatis* AJ13355 strain is shown as SEQ ID NO: 3, and the amino acid sequence of the protein encoded by this gene is shown as SEQ ID NO: 4. The nucleotide sequence of the yeeA gene of the *Enterobacter aerogenes* AJ110637 strain is shown as SEQ ID NO: 5, and the amino acid sequence of the protein encoded by this gene is shown as SEQ ID NO: 6.

<ynfM Gene>

The ynfM gene is a gene encoding a protein presumed to be a transport protein YnfM. The ynfM gene of the *Escherichia coli* MG1655 strain can also be referred to as b1596 or ECK1591. The nucleotide sequence of the ynfM gene of the *Escherichia coli* MG1655 strain is shown as SEQ ID NO: 7, and the amino acid sequence of the protein encoded by this gene (GenBank Accession No. NP_416113.1) is shown as SEQ ID NO: 8. The nucleotide sequence of the ynfM gene of *Pantoea ananatis* AJ13355 strain is shown as SEQ ID NO: 9, and the amino acid sequence of the protein encoded by this gene is shown as SEQ ID NO: 10. The nucleotide sequence of the ynfM gene of the *Enterobacter aerogenes* AJ110637 strain is shown as SEQ ID NO: 11, and the amino acid sequence of the protein encoded by this gene is shown as SEQ ID NO: 12. The nucleotide sequence of the ynfM gene of *Corynebacterium glutamicum* ATCC 13032 is shown as SEQ ID NO: 13, and the amino acid sequence of the protein encoded by this gene (GenBank Accession No. NP_602116.1) is shown as SEQ ID NO: 14. The nucleotide sequence of the ynfM gene of *Corynebacterium glutamicum* ATCC 13869 is shown as SEQ ID NO: 15, and the amino acid sequence of the protein encoded by this gene is shown as SEQ ID NO: 16.

<yjjP Gene>

The yjjP gene is a gene encoding a protein presumed to be an inner membrane structural protein. The yjjP gene of the *Escherichia coli* MG1655 strain can also be referred to as b4364 or ECK4354. The nucleotide sequence of the yjjP gene of the *Escherichia coli* MG1655 strain is shown as SEQ ID NO: 17, and the amino acid sequence of the protein encoded by this gene (GenBank Accession No. NP_418784.4) is shown as SEQ ID NO: 18. The nucleotide sequence of the yjjP gene of the *Enterobacter aerogenes* AJ110637 strain is shown as SEQ ID NO: 19, and the amino acid sequence of the protein encoded by this gene is shown as SEQ ID NO: 20.

<yjjB Gene>

The yjjB gene is a gene encoding a protein presumed to be a conserved inner membrane protein. The yjjB gene of the *Escherichia coli* MG1655 strain can also be referred to as b3463 or ECK4353. The nucleotide sequence of the yjjB gene of the *Escherichia coli* MG1655 strain is shown as SEQ ID NO: 21, and the amino acid sequence of the protein encoded by this gene (GenBank Accession No. NP_418783.2) is shown as SEQ ID NO: 22. The nucleotide sequence of the yjjB gene of the *Enterobacter aerogenes* AJ110637 strain is shown as SEQ ID NO: 23, and the amino acid sequence of the protein encoded by this gene is shown as SEQ ID NO: 24.

That is, the dicarboxylic acid efflux carrier gene may be, for example, a gene, such as a DNA, having the nucleotide sequence shown as SEQ ID NOS: 1, 3, 5, 7, 9, 11, 13, 15, 17, 19, 21, or 23. Also, the dicarboxylic acid efflux carrier may be, for example, a protein having the amino acid sequence shown as SEQ ID NOS: 2, 4, 6, 8, 10, 12, 14, 16, 18, 20, 22, or 24. The expression "a gene or protein has a nucleotide or amino acid sequence" can include when a gene or protein includes the nucleotide or amino acid sequence, and also when a gene or protein includes only the nucleotide or amino acid sequence.

The dicarboxylic acid efflux carrier gene may be a variant of the dicarboxylic acid efflux carrier genes exemplified above, namely, yeeA gene, ynfM gene, yjjP gene, and yjjB gene exemplified above, so long as the original function thereof is maintained. Similarly, the dicarboxylic acid efflux carrier may be a variant of the dicarboxylic acid efflux carriers exemplified above, namely, YeeA protein, YnfM protein, YjjP protein, and YjjB protein above-mentioned, so long as the original function thereof is maintained. Such a variant that maintains the original function may also be referred to as "conservative variant". That is, the terms "yeeA gene", "ynfM gene", "yjjP gene", and "yjjB gene" can include not only the yeeA gene, ynfM gene, yjjP gene, and yjjB gene exemplified above, respectively, but also can include conservative variants thereof. Similarly, the terms "YeeA protein", "YnfM protein", "YjjP protein", and "YjjB protein" can include not only the YeeA protein, YnfM protein, YjjP protein, and YjjB protein exemplified above, respectively, but also can include conservative variants thereof. Examples of the conservative variant can include, for example, homologues and artificially modified versions of the dicarboxylic acid efflux carrier genes and dicarboxylic acid efflux carriers exemplified above.

The expression "the original function is maintained" can mean that a variant of gene or protein has a function, such as activity or property, corresponding to the function, such as activity or property, of the original gene or protein. The expression "the original function is maintained" when referencing a gene can mean that a variant of the gene encodes a protein that maintains the original function. The expression "the original function is maintained" when referencing a dicarboxylic acid efflux carrier gene can mean that a variant of the gene encodes a protein having a dicarboxylic acid-secreting activity. The expression "the original function is maintained" when referencing a dicarboxylic acid efflux carrier can mean that the variant of the protein has a dicarboxylic acid-secreting activity.

Examples of the dicarboxylic acid secreted by the dicarboxylic acid efflux carrier can include the dicarboxylic acids mentioned above. The dicarboxylic acid efflux carrier may have a dicarboxylic acid-secreting activity for only a single kind of dicarboxylic acid, or may have a dicarboxylic acid-secreting activity for two or more kinds of dicarboxylic acids. The combination of dicarboxylic acid efflux carrier and dicarboxylic acid secreted thereby is not particularly limited. The term "dicarboxylic acid-secreting activity" when referencing the yeeA gene and the YeeA protein can mean, for example, an activity for secreting a dicarboxylic acid such as α-KG, malic acid, fumaric acid, succinic acid, and itaconic acid. The term "dicarboxylic acid-secreting activity" when referencing the ynfM gene and the YnfM protein can mean, for example, an activity for secreting a dicarboxylic acid such as α-KG, malic acid, fumaric acid, and succinic acid. The term "dicarboxylic acid-secreting activity" when referencing the yjjP gene, yjjB gene, YjjP protein, and YjjB protein can mean, for example, an activity for secreting succinic acid.

It can be confirmed that a variant of a protein has a dicarboxylic acid-secreting activity by, for example, introducing a gene encoding the variant into a strain having low succinic acid resistance such as the *P. ananatis* SC17(0) ΔsdhA strain, and confirming improvement of the succinic acid resistance. It can also be confirmed that a variant of a protein has a dicarboxylic acid-secreting activity by, for example, introducing a gene encoding the variant into a dicarboxylic acid-producing bacterium, and confirming improvement of dicarboxylic acid production amount.

Hereafter, examples of the conservative variants will be described.

Homologues of a dicarboxylic acid efflux carrier gene or homologues of a dicarboxylic acid efflux carrier can be easily obtained from public databases by, for example, BLAST search or FASTA search using any of the nucleotide sequences of the dicarboxylic acid efflux carrier genes exemplified above or any of the amino acid sequences of dicarboxylic acid efflux carriers exemplified above as a query sequence. Furthermore, homologues of a dicarboxylic acid efflux carrier gene can also be obtained by, for example, PCR using a chromosome of a microorganism such as bacteria as the template, and oligonucleotides prepared on the basis of a nucleotide sequence of any one of those known dicarboxylic acid efflux carrier genes as primers.

The dicarboxylic acid efflux carrier gene may be a gene, such as a DNA, encoding a protein having any of the aforementioned amino acid sequences, for example, the amino acid sequences of SEQ ID NOS: 2, 4, and 6 for the YeeA protein, the amino acid sequences of SEQ ID NOS: 8, 10, 12, 14, and 16 for the YnfM protein, the amino acid sequences of SEQ ID NOS: 18 and 20 for the YjjP protein, and the amino acid sequences of SEQ ID NOS: 22 and 24 for the YjjB protein, but which include substitution, deletion, insertion, or addition of one or several amino acid residues at one or several positions, so long as the original function is maintained. For example, the encoded protein may have an extended or deleted N-terminus and/or C-terminus. Although the number meant by the term "one or several" may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, or addition of one or several amino acid residues can be a conservative mutation that maintains normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if the substitution site is a hydrophobic amino acid; between Gln and Asn, if the substitution site is a polar amino acid; among Lys, Arg, and His, if the substitution site is a basic amino acid; between Asp and Glu, if the substitution site is an acidic amino acid; and between Ser and Thr, if the substitution site is an amino acid having hydroxyl group. Examples of substitutions considered to be conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, inversion, or the like of amino acid residues as mentioned above can includes a naturally occurring mutation due to an individual difference, or a difference of species of the organism from which the gene is derived (mutant or variant).

Furthermore, the dicarboxylic acid efflux carrier gene may be a gene, such as a DNA, encoding a protein having a homology of, for example, 50% or more, 65% or more, 80% or more, 90% or more, 95% or more, 97% or more, or 99% or more, to the entire amino acid sequence of any of the amino acid sequences mentioned above, so long as the original function is maintained. In this description, "homology" means "identity".

Furthermore, the dicarboxylic acid efflux carrier gene may be a DNA that is able to hybridize under stringent conditions with a probe that can be prepared from any of the aforementioned nucleotide sequences, for example, the nucleotide sequences shown as SEQ ID NOS: 1, 3, and 5 for the yeeA gene, the nucleotide sequences shown as SEQ ID NOS: 7, 9, 11, 13, and 15 for the ynfM gene, the nucleotide sequences shown as SEQ ID NOS: 17 and 19 for the yjjP gene, and the nucleotide sequences shown as SEQ ID NOS: 21 and 23 for the yjjB gene, such as a sequence complementary to the whole sequence or a partial sequence of any of the aforementioned nucleotide sequences, so long as the original function is maintained. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, 80%, 90%, 95%, 97%, or 99% homologous, and DNAs less homologous than the above do not hybridize to each other. Such stringent conditions can include washing conditions typical of Southern hybridization, for example, washing once, twice, or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

As described above, the probe used for the aforementioned hybridization may be a part of a sequence that is complementary to a gene. Such a probe can be prepared by PCR using oligonucleotides prepared on the basis of a known gene sequence as the primers and a DNA fragment containing any of the aforementioned genes as the template. For example, a DNA fragment having a length of about 300 bp can be used as the probe. When a DNA fragment having a length of about 300 bp is used as the probe, the washing conditions of the hybridization may be, for example, 50° C., 2×SSC and 0.1% SDS.

Furthermore, since properties concerning degeneracy of codons changes depending on the host, the dicarboxylic acid efflux carrier gene may can include substitution of corresponding codons for arbitrary codons. For example, the dicarboxylic acid efflux carrier gene may be modified to as to have codons optimum for the codon usage of a host to be used.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison, such as alignment, can be used to determine the sequence identity. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, a BLAST nucleotide search can be performed by using the BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program, for example, BLASTN for nucleotide sequences, and BLASTX for amino acid sequences, can be used. Alignment can also be manually performed.

The sequence identity between two sequences is calculated as a ratio of the same residues found at corresponding positions in the two sequences, when the two sequences are aligned so that the maximum coincidence of the residues is obtained for them.

<1-3> Method for Enhancing (Increasing) Expression of Gene

The methods for enhancing or increasing the expression of a gene such as dicarboxylic acid efflux carrier gene will be explained below.

The phrase "the expression of a gene is increased" can mean that the expression amount of the gene per cell is increased as compared with that of a non-modified strain. The term "non-modified strain" can refer to a reference strain that has not been modified so that the expression of an objective gene is increased. Examples of the non-modified strain can include a wild-type strain or a parent strain. The phrase "the expression of a gene is increased" may specifically mean that the transcription amount of the gene, such as the amount of mRNA, is increased, and/or the translation amount of the gene, such as the amount of the protein expressed from the gene, is increased. The phrase "the expression of a gene is increased" can also mean that "the expression of a gene is enhanced". The degree of the increase in the expression of a gene is not particularly limited, so long as the expression of the gene is increased as compared with that of a non-modified strain. The expression of a gene may be increased 1.5 times or more, 2 times or more, or 3 times or more, as compared with that of a non-modified strain. Furthermore, the phrase "the expression of a gene is increased" can include not only when the expression amount of an objective gene is increased in a strain that inherently expresses the objective gene, but also when the gene is introduced into a strain that does not inherently express the objective gene, and is expressed therein. That is, the phrase "the expression of a gene is increased" may also mean, for example, that an objective gene is introduced into a strain that does not possess the gene, and is expressed therein. Furthermore, so long as the expression of a gene is increased as a result, modification such as attenuation of the expression of an objective gene originally possessed by a host, or disruption of an objective gene originally possessed by a host may be performed, and then an appropriate type of the objective gene may be introduced into the host.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, or a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pACYC series vectors, and the broad host spectrum vector RSF1010. Specific examples of vector autonomously replicable in coryneform bacteria can include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; and pVC7 described in Japanese Patent Laid-open (Kokai) No. 9-070291.

When a gene is introduced, it is sufficient that the gene is able to be expressed in the chosen bacterium. Specifically, it is sufficient that the gene is introduced so that it can be expressed under the control of a promoter sequence that is able to function in the chosen bacterium. The promoter may be derived from the host, or may be a heterogenous promoter. The promoter may be the native promoter of the gene to be introduced, or a promoter of another gene. As the promoter, for example, such a stronger promoter as described herein may also be used.

A terminator for terminating the gene transcription can be provided downstream of the gene. The terminator is not particularly limited so long as it is able to function in the chosen bacterium. The terminator may be a terminator derived from the host, or may be a heterogenous terminator. The terminator may be the native terminator of the gene to be introduced, or may be a terminator of another gene. Specific examples of the terminator can include, for example, the T7 terminator, T4 terminator, fd phage terminator, tet terminator, and trpA terminator.

Vectors, promoters, and terminators available for use in various microorganisms are disclosed in detail in "Fundamental Microbiology Vol. 8, Genetic Engineering, KYORITSU SHUPPAN CO., LTD, 1987".

Furthermore, when two or more of genes are introduced, it is sufficient that the genes each are able to be expressed by the bacterium. For example, all the genes may be carried by a single expression vector or a chromosome. Furthermore, the genes may be separately carried by two or more expression vectors, or separately carried by one, or two or more expression vectors and a chromosome. An operon made up of two or more genes may also be introduced. The phrase "introducing two or more genes" can include, for example, introducing two or more kinds of the dicarboxylic acid efflux carrier genes, introducing genes coding for two or more kinds of proteins, such as enzymes, introducing genes coding for two or more subunits that make up a single protein complex, such as a single enzyme complex, and a combination of the foregoing.

The gene to be introduced is not particularly limited so long as it codes for a protein that functions in the host. The gene to be introduced may be a gene derived from the host, or may be a heterogenous gene. When two or more kinds of genes are introduced, these genes may be derived from one kind of organism, or may be derived from two or more different organisms. That is, for example, when two or more kinds of the dicarboxylic acid efflux carrier genes are introduced, all of the genes may be derived from the same organism, or they may be derived from different organisms.

The gene to be introduced can be obtained by, for example, PCR using primers designed on the basis of the nucleotide sequence of the gene, and using the genomic DNA of an organism having the gene, a plasmid carrying the gene, or the like as the template. The gene to be introduced may also be totally synthesized, for example, on the basis of the nucleotide sequence of the gene (Gene, 60(1), 115-127 (1987)). The obtained gene can be used as it is, or after being modified as required.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, a promoter, Shine-Dalgarno (SD) sequence, which can also be referred to as a ribosome binding site (RBS), or a spacer region between the RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The "stronger promoter" can mean a promoter providing an improved transcription of a gene compared with an inherent wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, PR promoter, and PL promoter. Examples of stronger promoters usable in coryneform bacteria can include the artificially modified P54-6 promoter (Appl. Microbiol. Biotechnolo., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence, which can also be referred to as ribosome binding site (RBS), for the gene on a chromosome with a stronger SD sequence. The "stronger SD sequence" can mean a SD sequence that provides an improved translation of mRNA compared with the inherent wild-type SD sequence of the gene. Examples of stronger SD sequences can include, for example, the RBS of the gene 10 derived from phage T7 (Olins P. O. et al, Gene, 1988, 73, 227-235). Furthermore, it is known that substitution, insertion, or deletion of several nucleotides in a spacer region between the RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. In *Escherichia coli* etc., a clear codon bias exists among the 61 amino acid codons found within the population of mRNA molecules, and the level of cognate tRNA appears directly proportional to the frequency of codon usage (Kane, J. F., Curr. Opin. Biotechnol., 6 (5), 494-500 (1995)). That is, if there is a large amount of mRNA containing an excess number of rare codons, a translational problem may arise. According to recent research, it has been suggested that clusters of AGG/AGA, CUA, AUA, CGA, or CCC codons may especially reduce both the quantity and quality of a synthesized protein. Such a problem occurs especially at the time of expression of a heterologous gene. Therefore, in the case of heterogenous expression of a gene or the like, the translation efficiency of the gene can be improved by replacing a rare codon present in the gene with a more frequently used synonymous codon. That is, the gene to be introduced may be modified, for example, so as to contain optimal codons according to the frequencies of codons observed in a chosen host. Codons can be replaced by, for example, the site-specific mutation method for introducing an objective mutation into an objective site of DNA. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

The method for the transformation is not particularly limited, and conventionally known methods can be used. Exemplary methods include treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternative examples include a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the expression of a gene can be confirmed by measuring an increase in the transcription amount of the gene, or by measuring an increase in the amount of a protein expressed from the gene. An increase in the expression of a gene can also be confirmed by measuring an increase in the activity of the protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

An increase in the activity of a protein can be confirmed by measuring the activity of the protein. The activity of a protein may be increased, for example, 1.5 times or more, 2 times or more, or 3 times or more, as compared with that of a non-modified strain.

The aforementioned methods for increasing the expression of a gene can be used for enhancement of the expression of arbitrary genes such as a gene encoding an enzyme of the dicarboxylic acid biosynthesis system, in addition to the enhancement of the expression of a dicarboxylic acid efflux carrier gene.

<1-4> Methods for Increasing Activity of Protein

The methods for increasing the activity of a protein will be explained below.

The expression "the activity of a protein is increased" can mean that the activity of the protein per cell is increased as compared with that of a non-modified strain. The term "non-modified strain" can refer to a reference strain that has not been modified so that the activity of an objective protein is increased. Examples of the non-modified strain can include a wild-type strain and parent strain. The state that "the activity of a protein is increased" may also be expressed as "the activity of a protein is enhanced". Specifically, the expression "the activity of a protein is increased" can mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but can also mean the transcription amount of a gene, i.e. the amount of mRNA, coding for the protein, or the translation amount of the protein, i.e. the amount of the protein. Furthermore, the phrase "the activity of a protein is increased" can include not only when the activity of an objective protein is increased in a strain inherently having the activity of the objective protein, but also when the activity of an objective protein is imparted to a strain not inherently having the activity of the objective protein. Furthermore, so long as the activity of the protein is eventually increased, the activity of an objective protein inherently present in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased 1.5 times or more, 2 times or more, or 3 times or more, as compared with that of a non-modified strain. Furthermore, when the strain before the modification does not have the activity of the objective protein, it is sufficient that the protein is produced as a result of introduction of the gene encoding the protein, and for example, the protein may be produced to such an extent that the enzyme activity can be measured.

The modification for increasing the activity of a protein is attained by, for example, increasing the expression of a gene coding for the protein. The method for increasing expression of a gene is as described above.

Furthermore, the modification that increases the activity of a protein can also be attained by, for example, enhancing the specific activity of the enzyme. Enhancement of the specific activity also can include desensitization to feedback inhibition. That is, when a protein is subject to feedback inhibition by a metabolite, the activity of the protein can be increased by making the bacterium harbor a gene encoding a mutant protein that has been desensitized to the feedback inhibition. The phrase "desensitization to feedback inhibition" can include complete elimination of the feedback inhibition, and attenuation of the feedback inhibition, unless otherwise stated. A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several positions of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

In addition, when a protein functions as a complex having a plurality of subunits, some or all of the subunits may be modified, so long as the activity of the protein is eventually increased. That is, for example, when the activity of a protein is increased by increasing the expression of a gene, the expression of a some or all of the genes that code for the subunits may be enhanced. It is usually preferable to enhance the expression of all of the genes coding for the subunits. Furthermore, the subunits that make up the complex may be derived from a single organism or from two or more kinds of organisms, so long as the complex has a function of the objective protein. That is, for example, genes of the same organism coding for a plurality of subunits may be introduced into a host, or genes of different organisms coding for a plurality of subunits may be introduced into a host.

An increase in the activity of a protein can be confirmed by measuring the activity of the protein. An increase in the activity of a protein can also be confirmed by confirming an increase in the expression of a gene coding for the protein.

The aforementioned methods for increasing the activity of a protein can be used for enhancement of activities of arbitrary proteins such as dicarboxylic acid biosynthesis system enzymes, and enhancement of the expression of arbitrary genes such as genes encoding those arbitrary proteins.

<1-5> Method for Reducing Activity of Protein

The methods for reducing activity of a protein will be explained below.

The expression "the activity of a protein is reduced" can mean that the activity of the protein per cell is reduced as compared with that of a non-modified strain. The term "non-modified strain" can refer to a reference strain that has not been modified so that the activity of an objective protein is reduced. Examples of the non-modified strain can include a wild-type strain or parent strain. The phrase "the activity of a protein is reduced" also can include when the activity of the protein has completely disappeared. Specifically, the expression "the activity of a protein is reduced" can mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene, i.e. the amount of mRNA, coding for the protein or the translation amount of the protein, i.e. the amount of the protein. The phrase "the number of molecules of the protein per cell is reduced" also can include when the protein does not exist at all. The phrase "the function of each molecule of the protein is reduced" also can include when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene coding for the protein. The phrase "the expression of a gene is reduced" can mean that the expression of the gene per cell is reduced as compared with that of a non-modified strain such as a wild-type strain and parent strain. The expression "the expression of a gene is reduced" may specifically mean that the transcription amount of the gene, i.e. the amount of mRNA, is reduced, and/or the translation amount of the gene, i.e. the amount of the protein expressed from the gene, is reduced. The phrase "the expression of a gene is reduced" also can include when the gene is not expressed at all. The phrase "the expression of a gene is reduced" can also be referred to as "the expression of a gene is attenuated". The degree of the reduction in the expression of a gene is not particularly limited, so long as the expression is reduced as compared with that of a non-modified strain. The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of these. The expression of a gene can be reduced by modifying an expression control sequence of the gene such as a promoter, Shine-Dalgarno (SD) sequence, which can also be referred to as ribosome-binding site (RBS), and a spacer region between the RBS and the start codon of the gene. When an expression control sequence is modified, one or more nucleotides, two or more nucleotides, or three or more nucleotides, of the expression control sequence can be modified. Furthermore, a part of or the entire expression control sequence may be deleted. The expression of a gene can also be reduced by, for example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a less frequently used synonymous codon in the chosen host. Furthermore, for example, the gene expression may be reduced due to disruption of a gene as described herein.

The modification for reducing the activity of a protein can also be attained by, for example, disrupting a gene coding for the protein. The expression "a gene is disrupted" can mean that a gene is modified so that a protein that can normally function is not produced. The phrase "a protein that normally functions is not produced" can include when the protein is not produced at all from the gene, and also when the function, such as activity or property, per molecule of the protein is reduced or eliminated.

Disruption of a gene can be attained by, for example, deleting a part of or the entire coding region of the gene on a chromosome. Furthermore, the entire gene including sequences upstream and downstream from the gene on a chromosome may be deleted. The region to be deleted may be any region such as an N-terminus region, an internal region, or a C-terminus region, so long as the activity of the protein can be reduced. Deletion of a longer region will usually more surely inactivate the gene. Furthermore, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region will usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof can include, for example, a marker gene such as antibiotic resistance genes, and a gene useful for production of an objective substance.

Such modification of a gene on a chromosome as described above can be attained by, for example, preparing a deficient-type gene modified so that it is unable to produce a protein that normally functions, and transforming a host with a recombinant DNA containing the deficient-type gene to cause homologous recombination between the deficient-type gene and the wild-type gene on a chromosome and thereby substitute the deficient-type gene for the wild-type gene on the chromosome. In this procedure, if a marker gene selected according to the characteristics of the host such as auxotrophy is included in the recombinant DNA, the operation becomes easier. Examples of the deficient-type gene can include a gene including deletion of all or a part of the gene, gene including a missense mutation, gene including a nonsense mutation, gene including a frame shift mutation, and gene including insertion of a transposon or marker gene. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex made up of a plurality of subunits, a part or all of the subunits may be modified, so long as the activity of the protein is eventually reduced. That is, for example, a part or all of the genes that code for the respective subunits may be disrupted or the like. Furthermore, when there is a plurality of isozymes of a protein, a part or all of the activities of the isozymes may be reduced, so long as the activity of the protein is eventually reduced. That is, for example, a part or all of the genes that code for the respective isozymes may be disrupted or the like.

A reduction in the activity of a protein can be confirmed by measuring the activity of the protein.

A reduction in the activity of a protein can also be confirmed by measuring a reduction in the expression of a gene coding for the protein. A reduction in the expression of a gene can be confirmed by measuring a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0%, of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be reduced to, for example, 50% or less, 20% or less, 10% or less, 5% or less, or 0%, of that of a non-modified strain.

Disruption of a gene can be confirmed by determining a nucleotide sequence of a part of or the entire gene, restriction enzyme map, full length, or the like of the gene depending on the method used for the disruption.

The aforementioned methods for reducing the activity of a protein as mentioned above can also be applied to reduction in the activities of arbitrary proteins such as an enzyme that catalyzes a reaction branching off from the biosynthesis pathway of an objective dicarboxylic acid to generate a compound other than the objective dicarboxylic acid, and reduction in the expression of arbitrary genes such as genes encoding those arbitrary proteins.

<2> Method for Producing Dicarboxylic Acid

The method as described herein includes a method for producing a dicarboxylic acid by culturing the bacterium in a medium to produce and accumulate the dicarboxylic acid in the medium, and collecting the dicarboxylic acid from the medium. One kind of dicarboxylic acid may be produced, or two or more kinds or dicarboxylic acids may be produced.

The medium is not particularly limited, so long as the bacterium can proliferate in the medium and produce a dicarboxylic acid. As the medium, for example, a medium typically used for culture of bacteria such as those belonging to the family Enterobacteriaceae and coryneform bacteria can be used. The medium may contain carbon source, nitrogen source, phosphorus source, and sulfur source, as well as other components various organic components and inorganic components as required. The types and concentrations of the medium components can be appropriately determined according to various conditions such as the type of the bacterium and the type of the dicarboxylic acid.

Specific examples of the carbon source can include, for example, saccharides such as glucose, fructose, sucrose, lactose, galactose, xylose, arabinose, blackstrap molasses, hydrolysate of starches, and hydrolysate of biomass, organic acids such as acetic acid, and citric acid, alcohols such as ethanol, glycerol, and crude glycerol, and fatty acids. As the carbon source, plant-derived materials can be used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the bacterium. As the carbon source, one kind of carbon source may be used, or two or more kinds of carbon sources may be used in combination.

The concentration of the carbon source in the medium is not particularly limited, so long as the bacterium can proliferate and produce a dicarboxylic acid. It is preferable to adjust the concentration of the carbon source in the medium to be as high as possible and within such a range that production of the dicarboxylic acid is not inhibited. Initial concentration of the carbon source in the medium may be, for example, usually 1 to 30% (w/v), or 3 to 10% (w/v). Furthermore, in accordance with consumption of the carbon source accompanying progress of the fermentation, the carbon source may be additionally added.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition product, ammonia, and urea. Ammonia gas and aqueous ammonia used for pH adjustment may also be used as a nitrogen source. As the nitrogen source, one kind of nitrogen source may be used, or two or more kinds of nitrogen sources may be used in combination.

Specific examples of the phosphate source can include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of other various organic and inorganic components can include, for example, inorganic salts such as sodium chloride and potassium chloride; trace metals such as iron, manganese, magnesium and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Furthermore, when an auxotrophic mutant strain that requires an amino acid or the like for growth thereof is used, it is preferable to add a required nutrient to the medium. For example, an itaconic acid-producing bacterium may require L-glutamic acid due to deficiency of isocitrate dehydrogenase etc. In such a case, it is preferable to add L-glutamic acid to the medium.

Culture conditions are not particularly limited, so long as the bacterium can proliferate and produce a dicarboxylic acid. The culture can be performed with, for example, conditions typically used for culture of bacteria such as those belonging to the family Enterobacteriaceae or coryneform bacteria. The culture conditions may be appropriately determined according to various conditions such as the type of the bacterium and the type of the dicarboxylic acid.

The culture can be performed by using a liquid medium. At the time of the culture, the bacterium cultured on a solid medium such as agar medium may be directly inoculated into a liquid medium, or the bacterium cultured in a liquid medium as seed culture may be inoculated into a liquid medium for main culture. That is, the culture may be performed separately as seed culture and main culture. In such a case, the culture conditions of the seed culture and the main culture may be or may not be the same. The amount of the bacterium present in the medium at the time of the start of the culture is not particularly limited. For example, seed culture showing an OD660 of 4 to 8 may be added to a medium for main culture at a ratio of 0.1 to 30 mass %, or 1 to 10 mass %, at the time of the start of the culture.

The culture can be performed as batch culture, fed-batch culture, continuous culture, or a combination of these. The medium used at the start of the culture can also be referred to as "starting medium". The medium added to the culture system (fermentation tank) in the fed-batch culture or the continuous culture can also be referred to as a "feed medium". To supply a feed medium to the culture system in the fed-batch culture or the continuous culture can also be referred to as "feed". Furthermore, when the culture is performed separately as seed culture and main culture, the culture schemes of the seed culture and the main culture may be or may not be the same. For example, both the seed culture and the main culture may be performed as batch culture. Alternatively, for example, the seed culture may be performed as batch culture, and the main culture may be performed as fed-batch culture or continuous culture.

The culture may be performed under an aerobic condition, microaerobic condition, or anaerobic condition. The culture can be performed under a microaerobic condition or anaerobic condition. The aerobic condition can mean that the dissolved oxygen concentration in the liquid medium is not lower than 0.33 ppm, which is the detection limit when using an oxygen membrane electrode, and preferably not lower than 1.5 ppm. The microaerobic condition can mean that, although oxygen is supplied to the culture system, dissolved oxygen concentration in the liquid medium is lower than 0.33 ppm. The anaerobic condition can mean a condition that oxygen is not supplied to the culture system. The culture may be performed under the condition chosen above during the whole culture period, or during only a part of the culture period. That is, "to culture under an aerobic condition" can mean that the culture is performed under an aerobic condition during at least a part of the whole culture period. Furthermore, "to culture under a microaerobic condition" can mean that the culture is performed under a microaerobic condition during at least a part of the culture period. Furthermore, "to culture under an anaerobic condition" can mean that the culture is performed under an anaerobic condition during at least a part of the culture period. The "part of the culture period" may be, for example, a period of 50% or more, 70 or more, 80% or more, 90% or more, 95% or more, or 99% or more, of the entire culture period. When the culture is performed separately as seed culture and main culture, the "entire culture period" may mean the entire period of the main culture. Specifically, the culture under an aerobic condition can be performed by aeration culture or shaking culture. The microaerobic condition or anaerobic condition can be attained by reducing aeration volume or stirring velocity, performing the culture in a sealed vessel without aeration, aerating an inert gas containing carbon dioxide gas, or the like to reduce dissolved oxygen concentration in the liquid medium.

The pH of the medium may be, for example, 3 to 10, or 4.0 to 9.5. The pH of the medium can be adjusted during the culture as required. The pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide.

The medium may contain carbonate ions, bicarbonate ions, carbon dioxide gas, or a combination of these. These components may be supplied, for example, by metabolism of the bacterium, or from carbonate salt and/or bicarbonate salt used for pH adjustment. These components may also be supplied by further adding carbonic acid, bicarbonic acid, salts thereof, or carbon dioxide gas, as required. Specific examples of salts of carbonic acid or bicarbonic acid can include, for example, calcium carbonate, magnesium carbonate, ammonium carbonate, sodium carbonate, potassium carbonate, ammonium bicarbonate, sodium bicarbonate, and potassium bicarbonate. Carbonate ions and/or bicarbonate ions may be added at a concentration of 0.001 to 5 M, 0.1 to 3 M, or 1 to 2 M. When carbon dioxide gas is present, carbon dioxide gas may be present in an amount of 50 mg to 25 g, 100 mg to 15 g, or 150 mg to 10 g, per litter of the solution.

The culture temperature may be, for example, 20 to 45° C., or 25 to 37° C. The culture time may be, for example, 10 to 120 hours. The culture may be continued, for example, until the carbon source present in the medium is consumed, or until the activity of the bacterium is lost.

By culturing the bacterium under such conditions as described above, a dicarboxylic acid can accumulate in the medium.

Production of a dicarboxylic acid can be confirmed by known methods used for detection or identification of compounds. Examples of such methods can include, for example, HPLC, LC/MS, GC/MS, and NMR. These methods can be independently used, or can be used in an appropriate combination.

The produced dicarboxylic acid can be collected by known methods used for separation and purification of compounds. Examples of such methods can include, for example, ion-exchange resin method, membrane treatment, precipitation, and crystallization. These methods can be independently used, or can be used in an appropriate combination. When a dicarboxylic acid is accumulated in cells of the bacterium, the cells can be disrupted with, for example, ultrasonic waves or the like, and then the dicarboxylic acid can be collected by the ion exchange resin method or the like from supernatant obtained by removing the cells from the cell-disrupted suspension by centrifugation. The collected dicarboxylic acid may be a free compound, a salt thereof, or a mixture of these. That is, the term "dicarboxylic acid" can mean a free dicarboxylic acid, a salt thereof, or a mixture of these, unless otherwise stated. Examples of the salt can include, for example, ammonium salt, sodium salt, and potassium salt.

Furthermore, when the dicarboxylic acid deposits in the medium, it can be collected by centrifugation or filtration. Dicarboxylic acid deposited in the medium and dicarboxylic acid dissolving in the medium may be isolated together after the dicarboxylic acid dissolving in the medium is crystallized.

The collected dicarboxylic acid may contain, for example, bacterial cells, medium components, moisture, and by-product metabolites of the bacterium, in addition to the dicarboxylic acid. Purity of the collected dicarboxylic acid may be, for example, 30% (w/w) or higher, 50% (w/w) or higher, 70% (w/w) or higher, 80% (w/w) or higher, 90% (w/w) or higher, or 95% (w/w) or higher.

EXAMPLES

Hereafter, the present invention will be more specifically explained with reference to examples. However, the present invention is not limited by these examples.

<Reference Example> Methods for Genetic Manipulation in *P. ananatis*

<1> Construction of *P. ananatis* SC17(0)/RSFRedTER Strain

The *P. ananatis* SC17(0) strain (VKPM B-9246) was cultured overnight in the LB liquid medium. The SC17(0) strain was deposited at the Russian National Collection of Industrial Microorganisms (VKPM, FGUP GosNII Genetika, 1 Dorozhny proezd., 1 Moscow 117545, Russia) on Sep. 21, 2005, and assigned an accession number VKPM B-9246. The culture broth (100 µL) was inoculated into fresh LB liquid medium (4 mL), and shaking culture was performed at 34° C. for 3 hours. The cells were collected, washed 3 times with 10% glycerol, and used as competent cells. A helper plasmid RSFRedTER (WO2008/090770A1) was introduced into the competent cells by electroporation. RSFRedTER is also referred to as RSF-Red-TER. The electroporation was performed by using GENE PULSER II (BioRad) under the conditions of an electric field intensity of 20 kV/cm, capacitor capacity of 25 µF, and resistance of 200Ω. After the electroporation, the cells were cultured for 2 hours in the SOC medium (20 g/L of Bacto tryptone, 5 g/L of yeast extract, 0.5 g/L of NaCl, 10 g/L of glucose), applied to the LB agar medium containing 25 mg/L of chloramphenicol (Cm), and cultured at 34° C. for 16 hours. As a result, a transformant that showed chloramphenicol resistance was obtained, and designated as SC17(0)/RSFRedTER strain.

<2> Construction of Gene-Disrupted Strain of *P. ananatis* SC17(0) Strain

The SC17(0)/RSFRedTER strain was cultured overnight in the LB liquid medium containing 25 mg/L of chloramphenicol. The culture broth (1 mL) was inoculated into the LB liquid medium (100 mL) containing IPTG at a final concentration of 1 mM and 25 mg/L of chloramphenicol, and shaking culture was performed at 34° C. for 3 hours. The cells were collected, then washed 3 times with 10% glycerol, and used as competent cells. By PCR using a plasmid having a drug resistance gene (drug resistance gene cassette) flanked by attL and attR sequences of λ phage as the template, a DNA fragment for disrupting objective gene having sequences of 50 bp complementary to internal sequences of the objective gene at both ends, and the drug resistance gene cassette between them was amplified. This DNA fragment was purified by using Wizard PCR Prep (Promega), and introduced into the competent cells by electroporation. The electroporation was performed by using GENE PULSER II (BioRad) under the conditions of an electric field intensity of 20 kV/cm, capacitor capacity of 25 µF, and resistance of 200Ω. After the electroporation, the SOC medium cooled on ice was immediately added to the cells, restoration culture was performed at 34° C. for 2 hours with shaking, and a strain in which the objective gene was replaced with the drug resistance gene cassette was selected on the LB agar medium containing the drug corresponding to the drug resistance gene.

<3> Removal of RSFRedTER Plasmid

If the RSFRedTER plasmid should be removed from a strain harboring this plasmid, the strain was streaked and cultured on a medium not containing the drug, and a colony that appeared was applied to the LB agar medium containing the M9 components (17.1 g/L of $Na_2HPO_4.12H_2O$, 3 g/L of $KH_2PO_4$, 0.5 g/L of NaCl, and 1 g/L of $NH_4Cl$), 10% sucrose, and 1 mM IPTG to obtain the strain from which the RSFRedTER plasmid was removed.

<4> Removal of Drug Resistance Gene

If the drug resistance gene should be removed from a strain containing this gene, the pMW-intxis-sacB(Cm) plasmid (see Reference Example <5>) was introduced into the strain by electroporation, and a transformant was selected on the LB agar medium containing 25 mg/L of chloramphenicol. The obtained transformant was streaked and cultured on an agar medium that did not contain any drug, replicated on a medium containing the drug corresponding to the drug resistance gene and a medium not containing the drug, and a strain in which the drug resistance gene was removed was selected.

<5> Construction of pMW-intxis-sacB(Cm)

The pMW-intxis-sacB(Cm) plasmid for removal of drug resistance gene was constructed by inserting the chloramphenicol resistance gene and the sacB gene derived from RSFRedTER (WO2008/090770A1) into pMW-intxis-ts (WO2007/037460) at the PstI-SphI site. Specifically, a fragment of about 4.0 kb containing the chloramphenicol resistance gene and the sacB gene was amplified by PCR using RSFRedTER as the template and the primers of SEQ ID NOS: 25 and 26, and purified. Separately, pMW-intxis-ts was treated with PstI and SphI, blant-ended, and phosphorylated by using BKL Kit (Takara). These two fragments were ligated by a ligation reaction, and used to transform the *E. coli* DH5α strain, and a transformant was selected on an L agarose plate (10 g/L of Bacto trypton, 5 g/L of Bacto yeast extract, 5 g/L of NaCl, 2% agarose) containing 25 mg/L of chloramphenicol and 100 mg/L of ampicillin to obtain DH5α/pMW-intxis-sacB(Cm) strain. From this strain, the plasmid pMW-intxis-sacB(Cm) was obtained in a conventional manner.

<Example 1> Evaluation of Effect of yeeA Gene Amplification in *P. ananatis* Succinic Acid-Producing Strain and α-KG-Producing Strain In this example, the yeeA gene was obtained by screening for dicarboxylic acid efflux carrier gene, and effect of yeeA gene amplification on dicarboxylic acid production was evaluated by using succinic acid-producing strain derived from the *P. ananatis* SC17(0) strain and α-KG-producing strain derived from the *P. ananatis* SC17 strain as the hosts.

<1-1> Screening for Dicarboxylic Acid Efflux Carrier Gene

<1-1-1> Construction of P. ananatis SC17(0)ΔsdhA Strain

First, a strain in which the sdhA gene encoding succinate dehydrogenase was disrupted was constructed by using the SC17(0) strain as the parent strain by the following method. PCR was performed by using the primers shown as SEQ ID NOS: 27 and 28, and pMW118-attL-Km$^r$-attR (WO2008/090770A1) as the template to amplify a DNA fragment for disruption of the sdhA gene containing the kanamycin (Km) resistance gene. By introducing this DNA fragment into the competent cells of the SC17(0)/RSFRedTER strain, and selecting a transformant on the LB agar medium containing 40 mg/L of kanamycin and 20 mM disodium malate, the SC17(0)ΔsdhA::Km strain was obtained, in which the sdhA gene was replaced with the Km resistance gene. The Km resistance gene was removed from this strain to obtain the SC17(0)ΔsdhA strain deficient in the sdhA gene.

<1-1-2> Screening for Dicarboxylic Acid Efflux Carrier Gene

The genomic library of the P. ananatis AJ13355 strain (FERM BP-6614) was introduced into the SC17(0)ΔsdhA strain, and screening for dicarboxylic acid efflux carrier gene was performed by using the succinic acid resistance as the marker. The AJ13355 strain was deposited at the Agency of Industrial Science and Technology, National Institute of Bioscience and Human-Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998, and assigned an accession number of FERM P-16644. Then, the deposit was converted to an international deposit under the provisions of Budapest Treaty on Jan. 11, 1999, and assigned an accession number of FERM BP-6614. As a result, improvement in the succinic acid resistance was observed for the strain into which a plasmid containing the yeeA gene was introduced, and thus it was estimated that the yeeA gene was a dicarboxylic acid efflux carrier gene.

<1-2> Evaluation of Effect of yeeA Gene Amplification in P. ananatis Succinic Acid-Producing Strain

<1-2-1> Construction of Succinic Acid-Producing Bacterium, P. ananatis SC17(0)ΔsdhA/RSFPP Strain The RSFPP plasmid was obtained by removing the region containing the gdhA gene from the RSFPPG plasmid (WO2010/027022A1). Specifically, the RSFPPG plasmid was treated with the restriction enzyme NspV, subjected to a heat treatment at 75° C. for 10 minutes for in activation of the enzyme, and then self-ligated by using DNA Ligation Kit (Takara Bio). The E. coli DH5α strain was transformed by using this DNA solution, and selection was performed on the LB agar medium containing 12.5 mg/L of tetracycline to obtain DH5α/RSFPP strain. The plasmid RSFPP was obtained from this strain in a conventional manner. The RSFPP plasmid is an expression plasmid for the prpC gene encoding methyl citrate synthase and the ppc gene encoding phosphoenolpyruvate carboxylase. The RSFPP plasmid can be used for enhancing carbon flow into the TCA cycle.

By introducing the RSFPP plasmid into the SC17(0) ΔsdhA strain, and selecting transformants on the LBGM9 agar medium (10 g/L of Bacto tryptone, 5 g/L of yeast extract, 10 g/L of NaCl, 6 g/L of Na$_2$HPO$_4$, 3 g/L of KH$_2$PO$_4$, 0.5 g/L of NaCl, 1 g/L of NH$_4$Cl, 5 g/L of glucose, 15 g/L of agar) containing 12.5 mg/L of tetracycline, a succinic acid-producing bacterium, SC17(0)ΔsdhA/RSFPP strain, was constructed.

<1-2-2> Evaluation of Effect of yeeA Gene Amplification in P. ananatis Succinic Acid-Producing Strain The plasmid containing the yeeA gene obtained by the screening was introduced into the succinic acid-producing bacterium, SC17(0)ΔsdhA/RSFPP strain, to thereby construct ayeeA gene-amplified strain (yeeA-amplified strain). pSTV28 was also introduced into the succinic acid-producing bacterium, SC17(0)ΔsdhA/RSFPP strain, to thereby construct a control strain (vector control strain). These strains were each cultured with shaking at 34° C. for 20.5 hours by using the MS 3% Sucrose for Succinate medium. After the culture, growth, consumed sugar amount, and accumulation amounts of α-KG and succinic acid in the medium were measured. The composition of the MS 3% Sucrose for Succinate medium is shown below.

Composition of MS 3% Sucrose for Succinate medium:

Group A:

| Sucrose | 30 g/L |
|---|---|
| MgSO$_4$•7H$_2$O | 0.5 g/L |

Group B:

| (NH$_4$)$_2$SO$_4$ | 5.0 g/L |
|---|---|
| KH$_2$PO$_4$ | 2.0 g/L |
| Yeast extract | 2.0 g/L |
| FeSO$_4$•7H$_2$O | 0.01 g/L |
| MnSO$_4$•5H$_2$O | 0.01 g/L |

(adjusted to pH 6.5 with KOH)

Group C:

| CaCO$_3$ | 20 g/L |
|---|---|

The components of the groups A and B were each sterilized in an autoclave at 115° C. for 10 minute, the component of Group C was sterilized with hot air at 180° C. for 3 hours, then they were mixed, and tetracycline and chloramphenicol were added to the mixture at 12.5 mg/L and 25 mg/L, respectively.

The results are shown in Table 1. The data are shown in the table as average±standard deviation of the results of the culture performed in triplicate for each strain. The succinic acid accumulation amount of the yeeA-amplified strain was almost equivalent to that of the control strain. The α-KG accumulation amount of the yeeA-amplified strain was higher than that of the control strain. These results suggest that YeeA recognizes not only succinic acid but also α-KG as a substrate.

TABLE 1

Effect of yeeA gene amplification in P. ananatis succinic acid-producing strain SC17(0)ΔsdhA/RSFPP

| | OD 620 nm (x1/51) | α-KG (g/L) | Succinate (g/L) | Consumed Sucrose (g/L) |
|---|---|---|---|---|
| Vector control strain | 0.334 ± 0.005 | 0.3 ± 0.0 | 9.6 ± 0.1 | 31.4 ± 0.0 |
| yeeA-Amplified strain | 0.345 ± 0.021 | 6.5 ± 1.5 | 9.2 ± 0.6 | 31.4 ± 0.0 |

<1-3> Evaluation of Effect of yeeA Gene Amplification in *P. ananatis* α-KG-Producing Strain <1-3-1> Construction of α-KG-Producing Bacterium, *P. ananatis* SC17sucA/RSFPP Strain The RSFPP plasmid was introduced into the *P. ananatis* SC17sucA strain (WO2005/085419), to thereby construct an α-KG-producing bacterium, SC17sucA/RSFPP strain. The SC17sucA strain was a sucA gene-deficient strain of the *P. ananatis* SC17 strain, and is also referred to as AJ417 strain. The SC17sucA strain (AJ417 strain) was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 26, 2004, and assigned an accession number of FERM BP-08646.

<1-3-2> Evaluation of Effect of yeeA Gene Amplification in *P. ananatis* α-KG-Producing Strain The plasmid containing the yeeA gene obtained by the screening was introduced into the α-KG-producing bacterium, SC17sucA/RSFPP strain, to thereby construct a yeeA gene-amplified strain (yeeA-amplified strain). pSTV28 was also introduced into the α-KG-producing bacterium, SC17sucA/RSFPP strain, to thereby construct a control strain (vector control strain).

These strains were each cultured with shaking at 34° C. for 23 hours by using the MS 3% Sucrose for Succinate medium supplemented with 200 mg/L each of Lys, Met, and DAP. After the culture, growth, consumed sugar amount, and accumulation amounts of Glu, α-KG, and acetic acid in the medium were measured. The results are shown in Table 2. The data are shown in the table as average±standard deviation of the results of the culture performed in quadruplicate for each strain. The Glu accumulation amount of the yeeA-amplified strain decreased, and the α-KG and acetic acid accumulation amounts of the yeeA-amplified strain increased, as compared with those of the control strain. On the basis of these results, it is considered that the α-KG concentration in the cells was reduced due to the amplification of the yeeA gene, and thereby conversion of α-KG into Glu was suppressed.

TABLE 2

Effect of yeeA gene amplification in *P. ananatis* α-KG-producing strain SC17sucA/RSFPP

|  | OD 620 nm (x1/51) | Glu (g/L) | Consumed Sucrose (g/L) | α-KG (g/L) | Acetate (g/L) |
| --- | --- | --- | --- | --- | --- |
| Vector control strain | 0.311 ± 0.005 | 2.7 ± 0.1 | 31 ± 0 | 14 ± 0.2 | 0.1 ± 0 |
| yeeA-Amplified strain | 0.311 ± 0.007 | 0.6 ± 0 | 31 ± 0 | 15.2 ± 0.5 | 0.9 ± 0.1 |

<1-4> Verification of Effect of Amplification of yeeA Gene Alone

The plasmid containing the yeeA gene obtained by the screening also contained genes around the yeeA gene. Therefore, it was determined whether the same effect as that obtained by introducing the aforementioned plasmid could also be obtained by amplification of the yeeA gene alone.

PCR was performed by using the primers shown as SEQ ID NOS: 29 and 30, and the chromosomal DNA of the *P. ananatis* AJ13355 strain (FERM BP-6614) as the template to obtain a DNA fragment containing the yeeA gene. The obtained DNA fragment was treated with HindIII and KpnI, and then inserted into pMW219 at the site for these restriction enzymes to obtain a yeeA gene expression plasmid pMW-PanyeeA. pMW-PanyeeA was introduced into the succinic acid-producing bacterium, SC17(0)ΔsdhA/RSFPP strain, and the α-KG-producing bacterium, SC17sucA/RSFPP strain, to thereby construct yeeA gene-amplified strains. Furthermore, pMW218 was also introduced into the succinic acid-producing bacterium, SC17(0)ΔsdhA/RSFPP strain, and the α-KG-producing bacterium, SC17sucA/RSFPP strain, to thereby construct control strains.

These strains were each cultured with shaking at 34° C. for 18.5 hours using the MS 3% Sucrose for Succinate medium supplemented with 200 mg/L each of Lys, Met, and DAP. After the culture, growth, consumed sugar amount, and accumulation amounts of α-KG and succinic acid in the medium were measured. The results are shown in Table 3. The data are shown in the table as average±standard deviation of the results of the culture performed in triplicate for each strain. When the yeeA gene alone was amplified in the succinic acid-producing bacterium, SC17(0)ΔsdhA/RSFPP strain, the accumulation amount of α-KG increased, and the accumulation amount of succinic acid did not substantially change, as in the case where the plasmid obtained by the screening was introduced. When the yeeA gene alone was amplified also in the α-KG-producing bacterium, SC17sucA/RSFPP strain, the accumulation amount of α-KG increased as in the case where the plasmid obtained by the screening was introduced. On the basis of these results, it was confirmed again that the yeeA gene is a dicarboxylic acid efflux carrier gene.

TABLE 3

Effect of amplification of yeeA gene alone in *P. ananatis* succinic acid-producing strain and α-KG-producing strain

|  | OD 620 nm (x1/51) | Consumed Sucrose (g/L) | α-KG (g/L) | Succinate (g/L) |
| --- | --- | --- | --- | --- |
| SC17(0)ΔsdhA/RSFPP pMW218 | 0.274 ± 0.007 | 32.3 ± 0.1 | 0.8 ± 0.1 | 10 ± 0.2 |
| SC17(0)ΔsdhA/RSFPP pMW-PanyeeA | 0.222 ± 0.021 | 33.1 ± 0 | 5.4 ± 0.2 | 9.2 ± 0.3 |
| SC17sucA/RSFPP pMW218 | 0.242 ± 0.002 | 31.7 ± 0.4 | 11.2 ± 0.1 | 0.1 ± 0 |
| SC17sucA/RSFPP pMW-PanyeeA | 0.28 ± 0.003 | 33.3 ± 0.1 | 17.2 ± 0.6 | 0.1 ± 0 |

<Example 2> Evaluation of Effect of ynfM Gene Amplification in *P. ananatis* Succinic Acid-Producing Strain and α-KG-Producing Strain In this example, effect of ynfM gene amplification on dicarboxylic acid production was evaluated by using succinic acid-producing strain derived from the *P. ananatis* SC17(0) strain and α-KG-producing strain derived from the *P. ananatis* SC17 strain as the hosts.

PCR was performed by using the primers shown as SEQ ID NOS: 31 and 32, and the chromosomal DNA of the *P. ananatis* AJ13355 strain (FERM BP-6614) as the template to obtain a DNA fragment containing the ynfM gene. The obtained DNA fragment was treated with EcoRI and PstI, and then inserted into pMW218 at the site for these restriction enzymes to obtain a ynfM gene expression plasmid pMW-PanynfM. pMW-PanynfM was introduced into the succinic acid-producing bacterium, SC17(0)ΔsdhA/RSFPP strain, and the α-KG-producing bacterium, SC17sucA/RSFPP strain, to thereby construct ynfM gene-amplified strains. Furthermore, pMW218 was also introduced into the succinic acid-producing bacterium, SC17(0)ΔsdhA/RSFPP strain, and the α-KG-producing bacterium, SC17sucA/RSFPP strain, to thereby construct control strains.

These strains were each cultured with shaking at 34° C. for 18.5 hours by using the MS 3% Sucrose for Succinate medium supplemented with 200 mg/L each of Lys, Met, and DAP. After the culture, growth, consumed sugar amount, and accumulation amounts of α-KG and succinic acid in the medium were measured. The results are shown in Table 4. The data are shown in the table as average±standard deviation of the results of the culture performed in triplicate for each strain. When the ynfM gene was amplified in the succinic acid-producing bacterium, SC17(0)ΔsdhA/RSFPP strain, the accumulation amount of α-KG slightly increased, and the accumulation amount of succinic acid did not significantly change. When the ynfM gene was amplified in the α-KG-producing bacterium, SC17sucA/RSFPP strain, the accumulation amount of α-KG markedly increased.

TABLE 4

Effect of amplification of ynfM gene in *P. ananatis* succinic acid-producing strain and α-KG-producing strain

|  | OD 620 nm (x1/51) | Consumed Sucrose (g/L) | α-KG (g/L) | Succinate (g/L) |
| --- | --- | --- | --- | --- |
| SC17(0)ΔsdhA/ RSFPP pMW218 | 0.274 ± 0.007 | 32.3 ± 0.1 | 0.8 ± 0.1 | 10 ± 0.2 |
| SC17(0)ΔsdhA/ RSFPP pMW - PanynfM | 0.214 ± 0.014 | 33.3 ± 0.1 | 2.5 ± 0.1 | 9.1 ± 0.2 |
| SC17sucA/RSFPP pMW218 | 0.242 ± 0.002 | 31.7 ± 0.4 | 11.2 ± 0.1 | 0.1 ± 0 |
| SC17sucA/RSFPP pMW - PanynfM | 0.28 ± 0.007 | 33.1 ± 0.1 | 15.4 ± 0.3 | 0.1 ± 0 |

<Example 3> Evaluation of Effect of yeeA Gene and ynfM Gene Amplification in *P. ananatis* Malic Acid-Producing Strain In this example, effects of yeeA gene amplification and ynfM gene amplification on dicarboxylic acid production were evaluated by using a malic acid-producing strain derived from *P. ananatis* SC17(0) strain as the host.

<3-1> Construction of Malic Acid-Producing Bacterium, *P. ananatis* SC17(0)Δm5/RSFPP Strain

*P. ananatis* contains three enzymes and five genes for them, malate dehydrogenase (mdh), malate-quinone oxidoreductase (mqo1 and mqo2), and malic enzyme (sfcA and maeB), as candidates for enzymes and genes of the malic acid decomposition system. Therefore, a multiple deficient strain for these five genes was constructed first.

PCR was performed by using the primers shown as SEQ ID NOS: 33 and 34, and pMW118-attL-Km$^r$-attR as the template to amplify a DNA fragment for disruption of the mdh gene. The SC17(0)/RSFRedTER strain was transformed with the obtained DNA fragment to obtain SC17(0) Δmdh::Km strain in which the mdh gene was replaced with the kanamycin (Km) resistance gene. The Km resistance gene was removed from this strain to obtain SC17(0)Δmdh deficient in the mdh gene.

PCR was performed by using the primers shown as SEQ ID NOS: 35 and 36, and pMW118-attL-Tet$^r$-attR (WO2005/010175) as the template to amplify a DNA fragment for disruption of the mqo1 gene. The SC17(0)/RSFRedTER strain was transformed with the obtained DNA fragment to obtain SC17(0)Δmqo::Tet strain in which the mqo1 gene was replaced with the tetracycline (Tet) resistance gene. The chromosome was extracted from this strain, and used to transform the SC17(0)Δmdh strain to obtain SC17(0) ΔmdhΔmqo::Tet strain.

PCR was performed by using the primers shown as SEQ ID NOS: 37 and 38, and pMW118-attL-Km$^r$-attR as the template to amplify a DNA fragment for disruption of the mqo2 gene. The SC17(0)/RSFRedTER strain was transformed with the obtained DNA fragment to obtain SC17(0) Δmqo2::Km strain in which the mqo2 gene was replaced with the Km resistance gene. The chromosome was extracted from this strain, and used to transform the SC17 (0)ΔmdhΔmqo::Tet strain to obtain SC17(0)ΔmdhΔmqo:: TetΔmqo2::Km strain. The drug resistance genes were removed from this strain to obtain SC17(0)Δm3 strain deficient in the mdh, mqo1, and mqo2 genes.

PCR was performed by using the primers shown as SEQ ID NOS: 39 and 40, and pMW118-attL-Km$^r$-attR as the template to amplify a DNA fragment for disruption of the sfcA gene. The SC17(0)/RSFRedTER strain was transformed with the obtained DNA fragment to obtain SC17(0) ΔsfcA::Km strain in which the sfcA gene was replaced with the Km resistance gene. The chromosome was extracted from this strain, and used to transform the SC17(0)Δm3 strain to obtain SC17(0)Δm3ΔsfcA::Km strain.

PCR was performed by using the primers shown as SEQ ID NOS: 41 and 42, and pMW118-attL-Tet$^r$-attR as the template to amplify a DNA fragment for disruption of the maeB gene. The SC17(0)/RSFRedTER strain was transformed with the obtained DNA fragment to obtain SC17(0) ΔmaeB::Tet strain in which the maeB gene was replaced with the Tet resistance gene. The chromosome was extracted from this strain, and used to transform the SC17(0) Δm3ΔsfcA::Km strain to obtain SC17(0)Δm3ΔsfcA::KmΔmaeB::Tet strain. The drug resistance genes were removed from this strain to obtain SC17(0)Δm5 strain deficient in the mdh, mqo1, mqo2, sfcA, and maeB genes.

The RSFPP plasmid was introduced into the SC17(0)Δm5 strain, to thereby construct a malic acid-producing bacterium, SC17(0)Δm5/RSFPP strain.

These strains were each cultured with shaking at 34° C. for 19 hours by using the MS 3% Sucrose for Succinate medium. After the culture, growth, consumed sugar amount, and accumulation amounts of organic acids in the medium were measured. The results are shown in Table 5. The data are shown in the table as average±standard deviation. In the RSFPP-introduced strain, the acetic acid accumulation amount decreased, and growth, sugar consumption amount, and malic acid accumulation amount increased, as compared with the strain not introduced with RSFPP.

TABLE 5

Malic acid-producing ability of malic acid decomposition system
enzyme-multiple deficient P. ananatis strain

|  | OD620 nm (x1/51) | Consumed Sucrose (g/L) | α-KG (g/L) | Malate (g/L) | Succinate (g/L) | Fumarate (g/L) | Acetate (g/L) |
| --- | --- | --- | --- | --- | --- | --- | --- |
| SC17 (0) Δm5 | 0.045 ± 0.003 | 3.6 ± 0.1 | 0.1 ± 0.1 | 0.5 ± 0.1 | 0.1 ± 0.1 | 0 ± 0 | 1.3 ± 0.2 |
| SC17 (0) Δm5/RSFPP | 0.068 ± 0.01 | 6.1 ± 0.3 | 0 ± 0.1 | 2.2 ± 0.1 | 0.2 ± 0.1 | 0.2 ± 0.1 | 0.6 ± 0 |

<3-2> Evaluation of Effect of yeeA Gene and ynfM Gene Amplification in *P. ananatis* Malic Acid-Producing Bacterium pMW-PanyeeA and pMW-PanynfM were each introduced into the malic acid-producing bacterium, SC17(0)Δm5/RSFPP strain, to thereby construct a yeeA gene-amplified strain and ynfM gene-amplified strain, respectively. pMW218 was also introduced into the malic acid-producing bacterium, SC17(0)Δm5/RSFPP strain, to thereby construct a control strain.

These strains were each cultured with shaking at 34° C. for 18.5 hours by using the MS 3% Sucrose for Succinate medium. After the culture, growth, consumed sugar amount, and accumulation amounts of organic acids in the medium were measured. The results are shown in Table 6. The data are shown in the table as average±standard deviation. In the yeeA gene-amplified strain and the ynfM gene-amplified strain, growth, consumed sugar amount, and accumulation amounts of various dicarboxylic acids such as malic acid markedly increased as compared with the control strain. Marked effect was obtained especially in the yeeA-amplified strain. These results strongly suggested that these dicarboxylic acid efflux carriers are transporters for excreting various dicarboxylic acids.

template to amplify a DNA fragment for disruption of the icd gene. The icd gene is a gene encoding isocitrate dehydrogenase (ICDH). The SC17(0)/RSFRedTER strain was transformed with the obtained DNA fragment to obtain SC17(0) Δicd::Km strain in which the icd gene was replaced with the Km resistance gene. The Km resistance gene was removed from this strain to obtain SC17(0)Δicd deficient in the icd gene.

PCR was performed by using the primers shown as SEQ ID NOS: 45 and 46, and pMW118-attL-Km$^r$-attR as the template to amplify a DNA fragment for disruption of the sdhA gene. The sdhA gene is a gene encoding succinate dehydrogenase. The SC17(0)/RSFRedTER strain was transformed with the obtained DNA fragment to obtain SC17(0) ΔsdhA::Km strain in which the sdhA gene was replaced with the Km resistance gene. The chromosome was extracted from this strain, and used to transform the SC17(0)Δicd strain to obtain SC17(0)ΔicdΔsdhA::Km strain.

PCR was performed by using the primers shown as SEQ ID NOS: 47 and 48, and pMW118-attL-Tet$^r$-attR as the template to amplify a DNA fragment for disruption of the aceBAK genes. This DNA fragment had a sequence complementary to an internal sequence of the aceB gene, and a sequence complementary in an internal sequence of the

TABLE 6

Effect of amplification of yeeA gene and ynfM gene in *P. ananatis* malic acid-producing bacterium

|  | OD620 nm (x1/51) | Consumed Sucrose (g/L) | α-KG (g/L) | Malate (g/L) | Succinate (g/L) | Fumarate (g/L) | Acetate (g/L) |
| --- | --- | --- | --- | --- | --- | --- | --- |
| pMW 218 | 0.054 ± 0.002 | 4.5 ± 0 | 0.9 ± 0 | 1.7 ± 0 | 0.1 ± 0 | 0.3 ± 0 | 0.5 ± 0 |
| pMW-PanyeeA | 0.265 ± 0.013 | 31.7 ± 0 | 1.6 ± 0.2 | 6.9 ± 1.3 | 5.2 ± 1.3 | 0.7 ± 0.1 | 0.1 ± 0 |
| pMW-PanynfM | 0.122 ± 0.005 | 10.5 ± 0.3 | 0.9 ± 0 | 3.2 ± 0.1 | 1 ± 0 | 0.6 ± 0 | 0.2 ± 0 |

<Example 4> Evaluation of Effect of yeeA Gene and ynfM Gene Amplification in *P. ananatis* Itaconic Acid-Producing Strain In this example, effects of yeeA gene amplification and ynfM gene amplification on itaconic acid production were evaluated by using an itaconic acid-producing strain derived from *P. ananatis* SC17(0) strain as the host.

<4-1> Construction of Itaconic Acid-Producing Bacterium, *P. ananatis* ITC01 Strain Itaconic acid is generated by decarboxylation of cis-aconitic acid, which is an intermediate of the citrate-isocitrate conversion in the TCA cycle. The decarboxylation of cis-aconitic acid is catalyzed by cis-aconitate decarboxylase (CAD). Therefore, CAD was enhanced, and isocitrate dehydrogenase (ICDH) and isocitrate lyase (ICL), which are isocitric acid decomposition system enzymes, were blocked.

PCR was performed by using the primers shown as SEQ ID NOS: 43 and 44, and pMW118-attL-Km$^r$-attR as the aceK gene, at the respective ends. The aceB gene is a gene encoding malate synthase. The aceA gene is a gene encoding isocitrate lyase. The aceK gene is a gene encoding isocitrate dehydrogenase kinase/phosphatase. The SC17(0)/RSFRedTER strain was transformed with the obtained DNA fragment to obtain SC17(0)ΔaceBAK::Tet strain in which the aceB-aceA-aceK genes were replaced with the Tet resistance gene. The chromosome was extracted from this strain, and used to transform the SC17(0)ΔicdΔsdhA::Km strain to obtain SC17(0)ΔicdΔsdhA::KmΔaceBAK::Tet strain. The drug resistance genes were removed from this strain to obtain SC17(0)ΔicdΔsdhAΔaceBAK strain deficient in the icd, sdhA, and aceBAK genes.

Figure 1B:
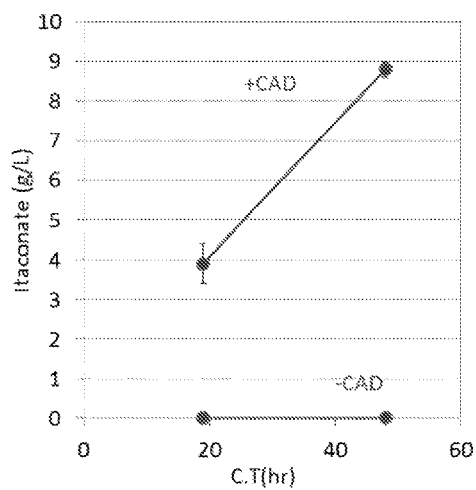
FIG. 1(B) shows the accumulation amounts of itaconic acid.

As for the cis-aconitate decarboxylase (CAD) gene, a nucleotide sequence optimized for the codon usage of *E. coli* (SEQ ID NO: 49) was designed on the basis of the nucleotide sequence of the CAD gene of *Aspergillus terreus*, and used. Optimization and synthesis of the nucleotide sequence of the CAD gene were entrusted to Genscript, and pSTV- CAD having the CAD gene introduced into the HindIII-KpnI site of pSTV28 was obtained. The pSTV-CAD plasmid and the RSFPP plasmid were introduced into the SC17(0) ΔicdΔsdhAΔaceBAK strain to construct an itaconic acid-producing bacterium, ITC01 (SC17(0) ΔicdΔsdhAΔaceBAK/RSFPP+pSTV-CAD) strain. The pSTV28 plasmid and the RSFPP plasmid were introduced into the SC17(0)ΔicdΔsdhAΔaceBAK strain to construct a control strain (–CAD). These strains were each cultured with shaking at 34° C. by using the MS 3% Sucrose for Succinate medium supplemented with glutamic acid at a final concentration of 5 g/L, and growth, and accumulation amount of itaconic acid in the medium were measured. The results are shown in FIG. 1. Whereas the control strain (–CAD) did not produce itaconic acid at all, the ITC01 strain accumulated about 9 g/L of itaconic acid.

<4-2> Evaluation of Effect of yeeA Gene and ynfM Gene Amplification in *P. Ananatis* Itaconic-Acid-Producing Strain pMW-PanyeeA and pMW-PanynfM were each introduced into the itaconic acid-producing bacterium, ITC01 strain, to thereby construct a yeeA gene-amplified strain and ynfM gene-amplified strain, respectively. pMW219 was also introduced into the itaconic acid-producing bacterium, ITC01 strain, to thereby construct a control strain.

These strains were each cultured with shaking at 34° C. for 48 hours by using the MS 3% Sucrose for Succinate medium supplemented with glutamic acid at a final concentration of 5 g/L. After the culture, growth, consumed sugar amount, amount of remaining glutamic acid, and accumulation amount of itaconic acid in the medium were measured. The results are shown in Table 7. The data are shown in the table as average±standard deviation. In the yeeA gene-amplified strain and the ynfM gene-amplified strain, consumed sugar amount increased, and accumulation amount of itaconic acid also increased, as compared with the control strain. With the yeeA gene-amplified strain and the ynfM gene-amplified strain, the added Glu was totally consumed, and most of it was converted into succinic acid (data are not shown).

Kazusakamatari, Kisarazu-shi, Chiba-ken, 292-0818, Japan) on Aug. 22, 2007, and assigned an accession number of FERM BP-10955.

<5-1> Construction of *E. aerogenes* ES06 Strain

The poxB gene on the genome of the *E. aerogenes* ES04 strain (US20100297716A1) constructed from the *Enterobacter aerogenes* AJ110637 (FERM BP-10955) strain was replaced with the pckA gene derived from the *Actinobacillus succinogenes* 130Z strain to construct *Enterobacter aerogenes* ES06 strain. The procedure is shown below.

Construction of λattL-Km$^r$-λattR-Ptac-pckA Gene Fragment

The total nucleotide sequence of the genomic DNA of the *Actinobacillus succinogenes* 130Z strain (ATCC 55618) (GenBank Accession No. CP000746) has already been opened to public, and the gene encoding phosphoenolpyruvate carboxykinase (gene name pckA, registration number Asuc_0221) has also been elucidated. The nucleotide sequence of the pckA gene of the *Actinobacillus succinogenes* 130Z strain is shown as SEQ ID NO: 50, and the amino acid sequence of the phosphoenolpyruvate carboxykinase encoded by this gene is shown as SEQ ID NO: 51. By using the genomic DNA of the *Actinobacillus succinogenes* 130Z strain as the template, and the primers shown as SEQ ID NOS: 52 and 53 designed on the basis of the aforementioned nucleotide sequence, PCR was performed (TaKaRa Prime Star (registered trademark), 94° C. for 10 seconds, 54° C. for 20 seconds, 72° C. for 90 seconds, 30 cycles) to obtain a DNA fragment containing the ORF region of pckA. PCR was also performed by using a DNA fragment containing λattL-Km$^r$-λattR-Ptac (WO2008/090770A1) as the template, and the primers shown as SEQ ID NOS: 54 and 55 (TaKaRa Prime Star (registered trademark), 94° C. for 10 seconds, 54° C. for 20 seconds, 72° C. for 90 seconds, 30 cycles) to obtain a DNA fragment containing λattL-Km$^r$-λattR-Ptac. Then, by using the DNA fragment containing the ORF region of pckA and the DNA fragment containing λattL-Km$^r$-λattR-Ptac as the template, and the primers shown as SEQ ID NOS: 53 and 54, PCR was

TABLE 7

Effect of amplification of yeeA gene and ynfM gene in *P. ananatis* itaconic acid-producing strain derived from SC17(0)

|  | OD 620 nm (x1/51) | Glu (g/L) | Consumed sucrose (g/L) | Itaconate (g/L) | Itaconate yield (%) |
| --- | --- | --- | --- | --- | --- |
| ITC01/pMW219 | 0.081 ± 0.004 | 3.2 ± 0 | 11.2 ± 0.5 | 5.3 ± 0.4 | 47.5 ± 3.1 |
| ITC01/pMW - PanyeeA | 0.048 ± 0.003 | 0 ± 0 | 34.5 ± 0.1 | 18.1 ± 0.1 | 52.5 ± 0.2 |
| ITC01/pMW - PanynfM | 0.081 ± 0.014 | 0 ± 0 | 32.5 ± 0.6 | 14 ± 2 | 43.1 ± 5.7 |

<Example 5> Evaluation of Effect of yjjPB Gene Amplification on Succinic Acid Production in *E. aerogenes*

In this example, effects of yjjPB gene amplification on succinic acid production was evaluated by using a succinic acid-producing strain derived from the *Enterobacter aerogenes* AJ110637 strain (FERM BP-10955) as the host. The AJ110637 strain (FERM BP-10955) was deposited at the independent administrative agency, National Institute of Advanced Industrial Science and Technology, International Patent Organism Depository (currently, independent administrative agency, National Institute of Technology and Evaluation, International Patent Organism Depositary, #120, 2-5-8 performed (TaKaRa Prime Star (registered trademark), 94° C. for 10 seconds, 54° C. for 20 seconds, 72° C. for 180 seconds, 35 cycles) to obtain a λattL-Km$^r$-λattR-Ptac-pckA gene fragment having sequences for recombination with the gene encoding pyruvate oxidase (gene name, poxB) at the both ends.

Construction of ES04/RSFRedTER Strain

The ES04 strain (US20100297716A1) was cultured overnight in the LB liquid medium. Then, the culture broth (100 μL) was inoculated into fresh LB liquid medium (4 mL), and shaking culture was performed at 34° C. for 3 hours. The cells were collected, washed 3 times with 10% glycerol, and used as competent cells. RSFRedTER (WO2008/090770A1) was introduced into the competent cells by electroporation. The electroporation was performed by using GENE PULSER II (BioRad) under the conditions of an electric field intensity of 20 kV/cm, capacitor capacity of 25 μF, and resistance of 200Ω. The cells were cultured for 2 hours in the SOC medium (20 g/L of Bacto tryptone, 5 g/L of yeast extract, 0.5 g/L of NaCl, 10 g/L of glucose), then applied to the LB agar medium containing 40 mg/L of chloramphenicol, and cultured for 16 hours. As a result, a transformant showing chloramphenicol resistance was obtained, and designated as ES04/RSFRedTER strain.

Construction of ES04ΔpoxB::λattL-Km$^r$-λattR-Ptac-pckA Strain

The ES04/RSFRedTER strain was cultured overnight in the LB liquid medium. Then, the culture broth (1 mL) was inoculated into LB liquid medium (100 mL) containing IPTG at a final concentration of 1 mM and 40 mg/L of chloramphenicol, and shaking culture was performed at 34° C. for 3 hours. The cells were collected, washed 3 times with 10% glycerol, and used as competent cells. The amplified λattL-Km$^r$-λattR-Ptac-pckA gene fragment was purified by using Wizard PCR Prep DNA Purification System (Promega), and introduced into the competent cells by electroporation. The cells were cultured for 2 hours in the SOC medium, then applied to the LB agar medium containing 50 mg/L of kanamycin, and cultured for 16 hours. A colony that appeared was purified on the same medium, and used together with the primers shown as SEQ ID NOS: 56 and 57 to perform colony PCR (TaKaRa Speed Star (registered trademark), 92° C. for 10 seconds, 56° C. for 10 seconds, 72° C. for 30 seconds, 40 cycles) and thereby confirm that the poxB gene on the genome had been replaced with the λattL-Km$^r$-λattR-Ptac-pckA gene. The obtained strain was applied to the LB agar medium containing 10% sucrose and 1 mM IPTG to remove the RSFRedTER plasmid and thereby obtain ES04ΔpoxB::λattL-Km$^r$-λattR-Ptac-pckA strain.

Removal of Kanamycin Resistance Gene from ES04ΔpoxB::λattL-Km$^r$-λattR-Ptac-pckA Strain In order to remove the kanamycin resistance gene from the ES04ΔpoxB::λattL-Km$^r$-λattR-Ptac-pckA strain, the RSF-int-xis plasmid (US20100297716A1) was used. RSF-int-xis was introduced into the ES04ΔpoxB::λattL-Km$^r$-λattR-Ptac-pckA strain by electroporation, and the strain was applied to the LB agar medium containing 40 mg/L of chloramphenicol, and cultured at 30° C. to obtain ES04ΔpoxB::λattL-Km$^r$-λattR-Ptac-pckA/RSF-int-xis strain. The obtained strain harboring the plasmid was purified on the LB agar medium containing 40 mg/L of chloramphenicol and 1 mM IPTG to obtain a plurality of single colonies. Then, the colonies were applied on the medium containing 50 mg/L of kanamycin, and cultured overnight at 37° C. A strain confirmed to be a strain from which the kanamycin resistance gene was removed by confirming that it could not grow was obtained. Then, in order to remove the RSF-int-xis plasmid from the obtained strain, it was applied to the LB agar medium containing 10% sucrose and 1 mM IPTG, and cultured overnight at 37° C. A strain showing chloramphenicol susceptibility among those of the colonies that appeared was designated as ES06 strain.

<5-2> Construction of *E. aerogenes* ES06ΔyeeA Strain

The ES06ΔyeeA strain was constructed by the λ-red method. Specifically, PCR was performed by using the primers shown as SEQ ID NOS: 58 and 59, and pMW118-attL-Km$^r$-attR as the template to amplify a fragment having sequences of 50 bp complementary to an internal sequence of the yeeA gene of *Enterobacter aerogenes* at the both ends, and the kanamycin resistance gene between the attL and attR sequences of λ phage. ES06/RSFRedTER strain obtained by introducing RSFRedTER into the ES06 strain by electroporation was cultured overnight in the LB liquid medium, the culture broth (1 mL) was inoculated into the LB liquid medium (100 mL) containing IPTG at a final concentration of 1 mM and 25 mg/L of chloramphenicol, and shaking culture was performed at 34° C. for 3 hours. The cells were collected, then washed 3 times with 10% glycerol, and used as competent cells. The amplified PCR fragment was purified by using Wizard PCR Prep (Promega), and introduced into the competent cells by electroporation. The electroporation was performed by using GENE PULSER II (BioRad) under the conditions of an electric field intensity of 20 kV/cm, capacitor capacity of 25 μF, and resistance of 200Ω. By selection on the LB agar medium containing 40 mg/L of kanamycin, ES06ΔyeeA::Km strain was obtained. The obtained strain was applied to the LB agar medium containing the M9 components (17.1 g/L of Na$_2$HPO$_4$.12H$_2$O, 3 g/L of KH$_2$PO$_4$, 0.5 g/L of NaCl, and 1 g/L of NH$_4$Cl), 10% sucrose, and 1 mM IPTG to obtain a strain from which the RSFRedTER plasmid was removed. Into this strain, the pMW-intxis-sacB(Cm) plasmid was introduced by electroporation, and by selection on the LB agar medium containing 25 mg/L of chloramphenicol, ES06ΔyeeA::Km/pMW-intxis-sacB(Cm) strain was obtained. This strain was purified on the LB agar medium, then replicated on the LB agar medium containing 40 mg/L of kanamycin, and a strain that became kanamycin and chloramphenicol-sensitive was designated as ES06ΔyeeA strain.

<5-3> Construction of *E. aerogenes* ES06ΔyeeAΔynfM Strain

The ES06ΔyeeAΔynfM strain was constructed by the aforementioned λ-red method from the ES06ΔyeeA strain. Specifically, PCR was performed by using the primers shown as SEQ ID NOS: 60 and 61, and pMW118-attL-Km$^r$-attR as the template to amplify a fragment having sequences of 50 bp complementary to an internal sequence of the ynfM gene of *Enterobacter aerogenes* at the both ends, and the kanamycin resistance gene between the attL and attR sequences of λ phage. ES06ΔyeeA/RSFRedTER strain obtained by introducing RSFRedTER into the ES06ΔyeeA strain by electroporation was cultured overnight in the LB liquid medium, the culture broth (1 mL) was inoculated into the LB liquid medium (100 mL) containing IPTG at a final concentration of 1 mM and 25 mg/L of chloramphenicol, and shaking culture was performed at 34° C. for 3 hours. The cells were collected, then washed 3 times with 10% glycerol, and used as competent cells. The amplified PCR fragment was purified by using Wizard PCR Prep (Promega), and introduced into the competent cells by electroporation. The electroporation was performed by using GENE PULSER II (BioRad) under the conditions of an electric field intensity of 20 kV/cm, capacitor capacity of 25 μF, and resistance of 200Ω. By selection on the LB agar medium containing 40 mg/L of kanamycin, ES06ΔyeeAΔynfM::Km strain was obtained. The obtained strain was applied to the LB agar medium containing the M9 components (17.1 g/L of Na$_2$HPO$_4$.12H$_2$O, 3 g/L of KH$_2$PO$_4$, 0.5 g/L of NaCl, and 1 g/L of NH$_4$Cl), 10% sucrose, and 1 mM IPTG to obtain a strain from which the RSFRedTER plasmid was removed. To this strain, the pMW-intxis-sacB(Cm) plasmid was introduced by electroporation, and by selection on the LB agar medium containing 25 mg/L of chloramphenicol, ES06ΔyeeAΔynfM::Km/pMW-intxis-sacB(Cm) strain was obtained. This strain was purified on the LB agar medium, then replicated on the LB agar medium containing 40 mg/L of kanamycin, and a strain that became kanamycin-sensitive was designated as ES06ΔyeeAΔynfM strain.

<5-4> Construction of *E. aerogenes* sdhA-Disrupted Strain

ES06ΔsdhA strain deficient in the sdhA gene encoding a subunit of succinate dehydrogenase was constructed from the ES06 strain by the aforementioned λ-red method. Specifically, PCR was performed by using the primers shown as SEQ ID NOS: 62 and 63, and pMW118-attL-Km$^r$-attR as the template to amplify a fragment having sequences of 50 bp complementary to an internal sequence of the sdhA gene of *Enterobacter aerogenes* at the both ends, and the kanamycin resistance gene between the attL and attR sequences of λ phage. The ES06/RSFRedTER strain was cultured overnight in the LB liquid medium, the culture broth (1 mL) was inoculated into the LB liquid medium (100 mL) containing IPTG at a final concentration of 1 mM and 25 mg/L of chloramphenicol, and shaking culture was performed at 34° C. for 3 hours. The cells were collected, then washed 3 times with 10% glycerol, and used as competent cells. The amplified PCR fragment was purified by using Wizard PCR Prep (Promega), and introduced into the competent cells by electroporation. The electroporation was performed by using GENE PULSER II (BioRad) under the conditions of an electric field intensity of 20 kV/cm, capacitor capacity of 25 µF, and resistance of 200Ω. By selection on the LB agar medium containing 40 mg/L of kanamycin, and 20 mM disodium malate, ES06ΔsdhA::Km strain was obtained. The obtained strain was applied to the LB agar medium containing the M9 components (17.1 g/L of Na$_2$HPO$_4$.12H$_2$O, 3 g/L of KH$_2$PO$_4$, 0.5 g/L of NaCl, and 1 g/L of NH$_4$Cl), 10% sucrose, and 1 mM IPTG to obtain a strain from which the RSFRedTER plasmid was removed. To this strain, the pMW-intxis-sacB(Cm) plasmid was introduced by electroporation, and by selection on the LB agar medium containing 25 mg/L of chloramphenicol, and 20 mM disodium malate, ES06ΔsdhA::Km/pMW-intxis-sacB(Cm) strain was obtained. This strain was purified on the LB agar medium containing 20 mM disodium malate, and then replicated on the LB agar medium containing 40 mg/L of kanamycin and 20 mM disodium malate, and a strain that became kanamycin-sensitive was designated as ES06ΔsdhA strain. Strains deficient in the sdhA gene were also derived from the ES06ΔyeeA and ES06ΔyeeAΔynfM strains in a similar manner, and designated as ES06ΔsdhAΔyeeA strain and ES06ΔsdhAΔyeeAΔynfM strain, respectively.

<5-5> Construction of pSTV28-AeyjjPB Plasmid pSTV28-AeyjjPB plasmid is a plasmid consisting of pSTV vector carrying the yjjPB genes derived from the *E. aerogenes* AJ110637 strain (FERM BP-10955). Specifically, it was constructed by the following method.

Primers S3 and S4 (SEQ ID NOS: 64 and 65) for amplifying the yjjPB genes derived from *E. aerogenes* AJ110637 strain were designed. PCR was performed by using these primers and the genome of the *E. aerogenes* AJ110637 strain as the template to obtain a DNA fragment containing the yjjPB genes. The obtained DNA fragment was inserted into the pSTV28 vector treated with BamHI and PstI using In Fusion HD Cloning Kit (Clontech). Competent cells of *Escherichia coli* JM109 (Takara Shuzo) were transformed with this DNA, applied to the LB agar medium containing 100 µM IPTG, 40 µg/mL of X-Gal, and 25 µg/mL of Cm, and cultured overnight. Then, white colonies that appeared were picked up, and subjected to single colony isolation to obtain transformants. Plasmids were extracted from the obtained transformants, and a plasmid in which the objective PCR product was inserted was designated as pSTV28-AeyjjPB.

<5-6> Construction of pSTV28-AeyjjP Plasmid pSTV28-AeyjjP plasmid is a plasmid consisting of pSTV vector carrying the yjjP gene derived from the *E. aerogenes* AJ110637 strain. Specifically, it was constructed by the following method.

Primers S3 and S5 (SEQ ID NOS: 64 and 66) for amplifying the yjjP gene derived from the *E. aerogenes* AJ110637 strain were designed. PCR was performed by using these primers and the genome of the *E. aerogenes* AJ110637 strain as the template to obtain a DNA fragment containing the yjjP gene. The obtained DNA fragment was inserted into the pSTV28 vector treated with BamHI and PstI by using In Fusion HD Cloning Kit (Clontech). Competent cells of *Escherichia coli* JM109 (Takara Shuzo) were transformed with this DNA, applied to the LB agar medium containing 100 µM IPTG, 40 µg/mL of X-Gal, and 25 µg/mL of Cm, and cultured overnight. Then, white colonies that appeared were picked up, and subjected to single colony isolation to obtain transformants. Plasmids were extracted from the obtained transformants, and a plasmid in which the objective PCR product was inserted was designated as pSTV28-AeyjjP.

<5-7> Construction of pSTV28-AePtac1000yjjB Plasmid pSTV28-AePtac1000yjjB plasmid is a plasmid consisting of the pSTV vector carrying the Ptac1000 promoter (SEQ ID NO: 67) and the yjjB gene derived from the *E. aerogenes* AJ110637 strain ligated together. Specifically, it was constructed by the following method.

First, primers S6 and S7 (SEQ ID NOS: 68 and 69) for amplifying a Ptac1000 promoter fragment were designed. PCR was performed by using these primers and λattL-Km$^r$-λattR-Ptac (WO2008/090770A1) as the template to obtain a DNA fragment containing the Ptac1000 promoter. Then, primers S8 and S4 (SEQ ID NOS: 70 and 65) for amplifying the yjjB gene derived from the *E. aerogenes* AJ110637 strain were designed. PCR was performed by using these primers and the genome of the *E. aerogenes* AJ110637 strain as the template to obtain a DNA fragment containing the yjjB gene. The obtained both DNA fragments were inserted into the pSTV28 vector treated with BamHI and PstI by using In Fusion HD Cloning Kit (Clontech). Competent cells of *Escherichia coli* JM109 (Takara Shuzo) were transformed with this DNA, applied to the LB agar medium containing 100 µM IPTG, 40 µg/mL of X-Gal, and 25 µg/mL of Cm, and cultured overnight. Then, white colonies that appeared were picked up, and subjected to single colony isolation to obtain transformants. Plasmids were extracted from the obtained transformants, and a plasmid in which the objective PCR product was inserted was designated as pSTV28-AePtac1000yjjB.

<5-8> Construction of *E. aerogenes* Strains for Evaluation

Into the ES06ΔsdhA strain and ES06ΔsdhAΔyeeAΔynfM strain, the RSFPP plasmid, and pSTV28 vector, pSTV28-AeyjjPB plasmid, pSTV28-AeyjjP plasmid, or pSTV28-AePtac1000yjjB plasmid were introduced by electroporation, and the transformed cells were selected on the LB agar medium containing 12.5 mg/L of tetracycline, and 25 mg/L of chloramphenicol, and purified on the LB agar medium to obtain ES06ΔsdhA/RSFPP+pSTV28 strain and ES06ΔsdhAΔyeeAΔynfM/RSFPP+pSTV28 strain as control strains, as well as ES06ΔsdhAΔyeeAΔynfM/RSFPP+pSTV28-AeyjjPB strain, ES06ΔsdhAΔyeeAΔynfM/RSFPP+pSTV28-AeyjjP strain, and ES06ΔsdhAΔyeeAΔynfM/RSFPP+pSTV28-AePtac1000yjjB strain as dicarboxylic acid efflux carrier gene-amplified strains.

<5-9> Evaluation of Succinic Acid-Producing Ability

Then, succinic acid-producing abilities of these strains were evaluated. These strains were each cultured overnight at 34° C. on an LBGM9 agar medium plate containing 12.5 mg/L of tetracycline and 25 mg/L of chloramphenicol. An appropriate amount of the obtained cells were inoculated into 5 mL of a succinic acid production medium contained in a test tube, and cultured at 34° C. with shaking at 120 rpm. The composition of the succinic acid production medium is shown below.

Composition of succinic acid production medium:
Group A:

| Sucrose | 30 g/L |
|---|---|
| MgSO$_4$•7H$_2$O | 0.5 g/L |

Group B:

| (NH$_4$)$_2$SO$_4$ | 5.0 g/L |
|---|---|
| KH$_2$PO$_4$ | 2.0 g/L |
| Yeast extract | 2.0 g/L |
| FeSO$_4$•7H$_2$O | 0.01 g/L |
| MnSO$_4$•5H$_2$O | 0.01 g/L |

(adjusted to pH 6.5 with KOH)

Group C:

| CaCO$_3$ | 20 g/L |
|---|---|

The components of the groups A and B were each sterilized in an autoclave at 115° C. for 10 minute, the component of Group C was sterilized with hot air at 180° C. for 3 hours, then they were mixed, and tetracycline and chloramphenicol were added to the mixture at 12.5 mg/L and 25 mg/L, respectively.

The results of yjjPB gene amplification are shown in Table 8. As compared with the ES06ΔsdhA/RSFPP strain as the control, the succinic acid-producing ability decreased in the ES06ΔsdhAΔyeeAΔynfM/RSFPP strain deficient in the yeeA gene and the ynfM gene. When the yjjPB genes were amplified in the ES06ΔsdhAΔyeeAΔynfM/RSFPP strain as the host, succinic acid-producing ability increased to be higher than that of the ES06ΔsdhA/RSFPP strain not deficient in the yeeA gene and the ynfM gene. These results revealed that, by amplifying the yjjPB genes in *Enterobacter aerogenes*, succinic acid-producing ability thereof is improved.

<Example 6> Evaluation of Effect of ynfM Gene Amplification on Succinic Acid Production by Coryneform Bacterium In this example, effect of ynfM gene amplification on succinic acid production was evaluated by using a succinic acid-producing strain derived from the *Brevibacterium lactofermentum* (*Corynebacterium glutamicum*) 2256 strain (ATCC 13869) as the host.

<6-1> Construction of Plasmid pVK9::PmsrA-ynfM for Expression of ynfM Gene

Plasmid pVK9::PmsrA-ynfM for expressing the ynfM gene derived from the *B. lactofermentum* 2256 strain was constructed by the following method.

First, the ynfM gene was ligated with the promoter of the msrA gene derived from the *B. lactofermentum* 2256 strain by crossover PCR. Specifically, PCR was performed by using the genomic DNA of the *B. lactofermentum* 2256 strain as the template, and the synthetic DNAs of SEQ ID NOS: 71 and 72 as the primers to obtain a PCR product containing the promoter region of the msrA gene. Separately, PCR was performed by using the genomic DNA of the *B. lactofermentum* 2256 strain as the template, and the synthetic DNAs of SEQ ID NOS: 73 and 74 as the primers to obtain a PCR product containing the ORF region of the ynfM gene. The sequences of SEQ ID NOS: 72 and 73 are partially complementary to each other. Then, the both PCR products were inserted into the pVK9 vector (WO2013/069634) treated with BamHI and PstI by using In Fusion HD Cloning Kit (Clontech). pVK9 is a shuttle vector of *Corynebacterium* bacteria and *E. coli*. With this DNA, competent cells of *Escherichia coli* JM109 (Takara Shuzo) were transformed, and applied to the LB agar medium containing 100 μM IPTG, 40 μg/mL of X-Gal, and 40 μg/mL of kanamycin, and cultured overnight. Then, white colonies that appeared were picked up, and subjected to single colony isolation to obtain transformants. Plasmids were extracted from the obtained transformants, and a plasmid in which the target PCR product was inserted was designated as pVK9::PmsrA-ynfM.

<6-2> Construction of *B. lactofermentum* 2256ΔsdhA Strain

<6-2-1> Construction of Plasmid pBS4SΔsdhA for Deleting sdhA Gene

PCR was performed by using the genomic DNA of the *B. lactofermentum* 2256 strain as the template, and the synthetic DNAs of SEQ ID NOS: 75 and 76 as the primers to obtain a DNA fragment containing the N-terminus side coding region of the sdhA gene. Separately, PCR was performed by using the genomic DNA of the *B. lactofermentum* 2256 strain as the template, and the synthetic DNAs of SEQ ID NOS: 77 and 78 as the primers to obtain a PCR

TABLE 8

Influence of yjjPB gene amplification on succinic acid production in *E. aerogenes*

| | OD 620 nm (x1/51) | Consumed sugar (g/l) | Succinate (g/l) | Succinate (%) |
|---|---|---|---|---|
| ES06ΔsdhA/RSFPP + pSTV28 | 0.27 ± 0.020 | 27 ± 2.1 | 7.9 ± 0.66 | 29.1 ± 0.82 |
| ES06ΔsdhAΔyeeAΔynfM/RSFPP + pSTV28 | 0.21 ± 0.0070 | 24 ± 0.85 | 4.1 ± 0.11 | 17.2 ± 0.19 |
| ES06ΔsdhAΔyeeAΔynfM/RSFPP + pSTV28-AeyjjPB | 0.32 ± 0.12 | 25 ± 7.2 | 9.1 ± 1.9 | 37.7 ± 3.8 | product containing the C-terminus side coding region of the sdhA gene. The sequences of SEQ ID NOS: 76 and 77 are complementary to each other. Then, both the PCR products were mixed in substantially equimolar amounts, and used together with the synthetic DNAs of SEQ ID NOS: 79 and 80 as the primers to perform crossover PCR, and thereby obtain a DNA fragment for deleting sdhA. Then, this DNA fragment was treated with BamHI, and inserted into the pBS4S vector (WO2007/046389) at the BamHI site. Competent cells of *Escherichia coli* JM109 (Takara Shuzo) were transformed with this DNA, applied to the LB agar medium containing 100 µM IPTG, 40 µg/mL of X-Gal, and 40 µg/mL of Km, and cultured overnight. Then, white colonies that appeared were picked up, and subjected to single colony isolation to obtain transformants. Plasmids were extracted from the obtained transformants, and a plasmid in which the objective PCR product was inserted was designated as pΔsdhA56.

<6-2-2> Construction of *B. lactofermentum* 2256ΔsdhA Strain pΔsdhA56 obtained above does not contain any region that enables autonomous replication thereof in cells of coryneform bacteria. Thus, when coryneform bacteria are transformed with this plasmid, a strain in which this plasmid is incorporated into the genome by homologous recombination appears as a transformant, although it occurs at an extremely low frequency. Therefore, pΔsdhA56 was introduced into the *B. lactofermentum* 2256 strain by the electric pulse method. The cells were applied to the CM-Dex agar medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate, 10 µg/L of biotin, 15 g/L of agar, adjusted to pH 7.5 with NaOH) containing 25 µg/mL of kanamycin, and cultured at 31.5° C. It was confirmed by PCR that the grown strain was a once-recombinant strain in which pΔsdhA56 was incorporated into the genome by homologous recombination. This once-recombinant strain had both the wild-type sdhA gene and the deletion type sdhA gene.

The once-recombinant strain was cultured overnight in the CM-Dex liquid medium (having the same composition as that of the CM-Dex agar medium, with the proviso that 15 g/L of agar is omitted), and the culture broth was applied to the S10 agar medium (100 g/L of sucrose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.4-5H_2O$, 3 g/L of urea, 1.2 g/L of soybean protein hydrolysate solution, 20 g/L of agar, adjusted to pH 7.5 with NaOH, and autoclaved at 120° C. for 20 minutes), and cultured at 31.5° C. Among colonies that appeared, a strain that showed kanamycin susceptibility was purified on the CM-Dex agar medium. The genomic DNA was prepared from the purified strain, and used together with the synthetic DNAs of SEQ ID NOS: 75 and 78 as the primers to perform PCR and thereby confirm deletion of the wild-type sdhA gene, and the strain was designated as 2256ΔsdhA strain.

<6-3> Evaluation of Succinic Acid-Producing Ability

Into the 2256ΔsdhA strain, the pVK9 plasmid and the pVK9::PAmsrA-ynfM plasmid were each introduced by electroporation to obtain 2256ΔsdhA/pVK9 strain as a control strain, and 2256ΔsdhA/pVK9::PmsrA-ynfM as a ynfM gene-amplified strain.

Then, succinic acid-producing abilities of these strains were evaluated. These strains were each cultured overnight at 31.5° C. on a CM-Dex agar medium plate containing 25 mg/L of kanamycin. An appropriate amount of the obtained cells were inoculated into 5 mL of a succinic acid production medium contained in a test tube, and cultured at 31.5° C. with shaking at 120 rpm. The composition of the succinic acid production medium is shown below.

Composition of Succinic Acid Production Medium:

| Glucose | 60 g/L |
|---|---|
| Ammonium sulfate | 6 g/L |
| $KH_2PO_4$ | 0.54 g/L |
| $FeSO_4•7H_2O$ | 12 mg/L |
| $MnSO_4•5H_2O$ | 12 mg/L |
| $VB_1$ | 120 mg/L |
| Biotin | 120 mg/L |
| Mameno | 68 mg/L (in terms of total nitrogen) |

The medium was adjusted to pH 7.0 with KOH, and sterilized at with 120° C. for 20 minutes in an autoclave, and then $MgCO_3$ sterilized with hot air at 180° C. for 3 hours or longer and left to cool was added to the medium at 50 g/L.

The results are shown in Table 9. As compared with the 2256ΔsdhA/pVK9 strain as the control, succinic acid-producing ability of the 2256ΔsdhA/pVK9::PmsrA-ynfM strain, in which the ynfM gene was enhanced, was improved. These results revealed that, by amplifying the ynfM gene in coryneform bacteria, succinic acid-producing ability is improved.

TABLE 9

Influence of ynfM gene amplification on succinic acid production in coryneform bacterium

| | Accumulation amount of succinate (g/L) ± S.E. | Yield of succinate (%) ± S.E. |
|---|---|---|
| 2256ΔsdhA/pVK9 | 7.8 ± 0.43 | 17.3 ± 0.89 |
| 2256ΔsdhA/pVK9::PmsrA-ynfM | 12.7 ± 0.19 | 22 ± 0.33 |

<Example 7> Evaluation of Effect of yjjPB Gene Amplification on Succinic Acid Production by *P. ananatis* Under Anaerobic Condition In this example, effect of yjjPB gene amplification on succinic acid production under an anaerobic condition was evaluated by using a succinic acid-producing strain derived from the *P. ananatis* SC17(0) strain as the host.

<7-1> Construction of *P. ananatis* FKPS13 Strain

By substituting the Tet$^r$ gene for the budABC genes encoding the 2,3-butanediol biosynthesis system on the genome of the *P. ananatis* SC17(0) strain, *P. ananatis* FKSP 13 strain (SC17(0)ΔbudABC::Tet$^r$ strain) was constructed. The method is shown below.

PCR was performed by using the primers shown as SEQ ID NOS: 81 and 82, and pMW118-attL-Tet$^r$-attR as the template to amplify a DNA fragment for disruption of the budABC genes. The obtained DNA fragment was purified by using Wizard PCR Prep DNA Purification System (Promega), and introduced into competent cells of the SC17(0)/RSFRedTER strain by electroporation. The cells were cultured for 2 hours in the SOC medium, then applied to the LB agar medium containing 25 mg/L of chloramphenicol and 12.5 mg/L of tetracycline, and cultured at 34° C. for 16 hours. Colonies that appeared were purified on the same medium, and then used together with the primers shown as SEQ ID NOS: 83 and 84 to perform colony PCR (TaKaRa Speed Star (registered trademark), 92° C. for 10 seconds, 56° C. for 10 seconds, 72° C. for 30 seconds, 40 cycles), and thereby it was confirmed that the budABC genes on the genome was replaced with the Tet resistance gene. The obtained strain was applied to the LB agar medium containing 10% sucrose and 1 mM IPTG to remove the RSFRedTER plasmid to obtain SC17(0)ΔbudABC::Tet$^r$ strain. This strain was designated as FKSP13.

<7-2> Construction of *P. ananatis* YDSP24

As a strain that accumulates succinic acid in a medium under an anaerobic condition, YDSP24 strain, which was deficient in the alcohol dehydrogenase adhE gene and the lactate dehydrogenase ldhE gene, and in which the pyruvate carboxylasepyc gene was amplified, was constructed from the FKSP13 strain. In the construction of this strain, in order to make the λ-red method and removal of the drug resistance gene easier, a plasmid RSFRedIX was constructed and introduced.

<7-2-1> Construction of RSFRedIX

PCR was performed by using the RSFParaIX plasmid (Appl. Environ. Microbiol., 2014 Nov. 21, pii:AEM.03213-14) as the template, and the primers shown as SEQ ID NOS: 85 and 86 to obtain a DNA fragment comprising the araC gene and the xis-int genes of λ-phage, in which the xis-int genes were ligated downstream of the ParaBAD promoter in the reverse direction with respect to the araC gene. This DNA fragment was purified by using Wizard PCR Prep Kit (Promega), and then digested with NotI. This digested fragment and a fragment obtained by digesting RSFRedTER with NotI were ligated by using Takara DNA Ligation Kit, and the *E. coli* DH5α strain was transformed with the ligated fragment, and applied on the LB agar medium containing 25 mg/L of chloramphenicol to obtain a transformant. The objective plasmid RSFRedIX was obtained from the transformant. RSFRedIX carries the λ-Red genes, gam, bet, and exo, downstream from the Plac promoter, and carries the int-xis genes downstream from the ParaBAD promoter. With RSFRedIX, there can be performed incorporation by the λ-Red system based on IPTG induction, and removal of drug resistance gene based on arabinose induction.

<7-2-2> Removal of Tetracycline Resistance Gene from SC17(0)ΔbudABC::Tet$^r$ Strain RSFRedIX was introduced into the SC17(0)ΔbudABC::Tet$^r$ strain by electroporation, and the strain was applied to the LB agar medium containing 25 mg/L chloramphenicol, and cultured at 34° C. to obtain SC17(0)ΔbudABC::Tet$^r$/RSFRedIX strain. The SC17(0)ΔbudABC::Tet$^r$/RSFRedIX strain was purified on the LB agar medium containing 25 mg/L chloramphenicol and 10 mM arabinose to obtain a plurality of single colonies. Then, they were applied to the LB agar medium containing 12.5 mg/L of tetracycline, and cultured at 34° C. for 16 hours. A strain confirmed to be a strain from which the tetracycline resistance gene was removed by confirming that it could not grow was designated as SC17(0)ΔbudABC/RSFRedIX strain.

<7-2-3> Construction of *P. ananatis* SC17(0) ΔbudABCΔadhE::Tet$^r$/RSFRedIX Strain PCR was performed by using the primers shown as SEQ ID NOS: 87 and 88, and pMW118-attL-Tet$^r$-attR as the template to amplify a DNA fragment for disruption of the adhE gene. The SC17(0)ΔbudABC/RSFRedIX strain was cultured overnight in the LB liquid medium, 1 mL of the culture broth was inoculated into 100 mL of the LB liquid medium containing IPTG at a final concentration of 1 mM, and 25 mg/L of chloramphenicol, and shaking culture was performed at 34° C. for 3 hours. The cells were collected, then washed 3 times with 10% glycerol, and used as competent cells. The amplified DNA fragment was purified by using Wizard PCR Prep (Promega), and introduced into the competent cells by electroporation. The electroporation was performed by using GENE PULSER II (BioRad) under the conditions of an electric field intensity of 20 kV/cm, capacitor capacity of 25 µF, and resistance of 200Ω. The cells were cultured at 34° for 16 hours on the LB agar medium containing 12.5 mg/L of tetracycline and 25 mg/L of chloramphenicol. A colony that appeared was purified on the same medium, and used together with the primers shown as SEQ ID NOS: 89 and 90 to perform colony PCR, and it was thereby confirmed that the adhE gene on the genome had been replaced with the Tet resistance gene to obtain SC17(0),ΔbudABCΔadhE::Tet$^r$/RSFRedIX strain.

<7-2-4> Construction of *P. ananatis* SC17(0),ppc::P4071-pyc::Km$^r$ Strain and SC17(0),ldh::P4071-pyc::Km$^r$ Strain For deletion of the ldhA gene encoding the lactate dehydrogenase of the SC17(0),ΔbudABCΔadhE::Tet$^r$/RSFRedIX strain (corresponding to the nucleotide numbers 1621607 to 1622599 of the *P. ananatis* AJ13355 strain registered as GenBank Accession Number NC_017531.1), and for enhancement of pyruvate carboxylase of the same at the same time, SC17(0),ppc::P4071-pyc::Km$^r$ strain was constructed first. Then, by introducing a λattL-Km$^r$-λattR-P4071-pyc gene fragment having sequences homologous to upstream and downstream sequences of the ldh gene, which was prepared by PCR by using the genomic DNA of the SC17(0),ppc::P4071-pyc::Km$^r$ strain as the template, into the SC17(0) strain by the λ-red method, SC17(0),ldh::P4071-pyc::Km$^r$ strain was constructed.

Construction of SC17(0),ppc::P4071-pyc::Km$^r$ Strain

First, the ldh gene region on the genome of SC17(0) was replaced with a sequence containing the pyc gene as follows. PCR was performed by using the chromosomal DNA of the *Brevibacterium lactofermentum* (*Corynebacterium glutamicum*) 2256 strain (ATCC 13869) as the template, and the synthetic DNAs shown as SEQ ID NOS: 91 and 92 as the primers to amplify a DNA fragment containing the ORF region of the pyc gene. Furthermore, PCR was performed by using a DNA fragment containing λattL-Km$^r$-λattR-Ptac (WO2008/090770A1) as the template, and the synthetic DNAs shown as SEQ ID NOS: 93 and 94 as the primers to amplify a DNA fragment containing λattL-Km$^r$-λattR-P4071. Then, PCR was performed by using the DNA fragment containing the ORF region of the pyc gene and the DNA fragment containing λattL-Km$^r$-λattR-P4071 as the template, as well as the synthetic DNAs shown as SEQ ID NOS: 92 and 93 as the primers to obtain a λattL-Km$^r$-λattR-P4071-pyc gene fragment having sequences homologous to upstream and downstream sequences of the ppc gene at the respective ends. The λattL-Km$^r$-λattR-P4071-pyc gene fragment was purified by using Wizard PCR Prep (Promega), and introduced into the SC17(0)/RSF-Red-TER strain by the aforementioned λ-red method. By selecting transformants on an LB agarose plate containing 40 mg/L of kanamycin, SC17(0),ppc::P4071-pyc::Km$^r$/RSF-Red-TER strain was obtained, in which the objective characteristic was introduced into the ppc gene region. The obtained strain was purified on an LB agarose plate containing 10% sucrose and 1 mM IPTG to obtain a strain in which the RSF-Red-TER plasmid was removed. The obtained strain was designated as SC17(0),ppc::P4071-pyc::Km$^r$ strain.

Construction of SC17(0),ldh::P4071-pyc::Km$^r$ Strain

In the SC17(0),ppc::P4071-pyc::Km$^r$ strain, the pyc gene was inserted into the ppc gene region, and therefore it was deficient in the ppc gene. Therefore, the following operations were performed in order to change the insertion position of the pyc gene from the ppc gene region to the ldh gene region. PCR was performed by using extracted genome of the SC17(0),ppc::P4071-pyc::Km$^r$ strain as the template, and the primers shown as SEQ ID NOS: 95 and 96 to obtain a λattL-Km$^r$-λattR-P4071-pyc gene fragment having sequences homologous to upstream and downstream regions of the ldh gene of *P. ananatis* at the respective ends. This fragment was introduced into the SC17(0)/RSF-Red-TER strain by the aforementioned λ-red method. Transformants were selected on an LB agarose plate containing 40 mg/L of kanamycin, and the genome structures thereof were confirmed by PCR using the synthetic DNAs shown as SEQ ID NOS: 97 and 98 as the primers to obtain SC17(0),ldh::P4071-pyc::Km$^r$/RSFRed-TER strain, in which the objective characteristic was introduced into the ldh gene region. This strain was deficient in the ldh gene instead of the ppc gene. The obtained strain was purified on an L agarose plate containing 10% sucrose and 1 mM IPTG to obtain a strain in which the RSF-Red-TER plasmid was removed. The obtained strain was designated as SC17(0),ldh::P4071-pyc::Km$^r$ strain.

<7-2-5> Construction of *P. ananatis* YDSP24

The ldhA gene of the SC17(0),ΔbudABCΔadhE::Tet$^r$/RSFRedIX strain was deleted by the aforementioned λ-red method, and pyruvate carboxylase of the same was enhanced at the same time. The procedure is shown below.

The genome of the SC17(0),ldh::P4071-pyc::Km$^r$ was extracted, and introduced in an amount of 700 μg into the SC17(0),ΔbudABCΔadhE::Tet$^r$/RSFRedIX strain by the electric pulse method. The cells were applied on an LB agarose plate containing 12.5 mg/L of tetracycline and 50 μg/mL of kanamycin, and cultured at 34° C. for about 16 hours. For a grown tetracycline and kanamycin-resistant strain, introduction of the characteristic of P4071-pyc::Km$^r$ in the ldh gene region was confirmed by PCR using the synthetic DNAs shown as SEQ ID NOS: 97 and 98 as the primers, and this strain was designated as SC17(0)ΔbudABCΔadhE::Tet$^r$ ldh::P4071-pyc::Km$^r$/RSFRedIX strain. This strain was purified in the LB agar medium containing 25 mg/L of chloramphenicol and 10 mM arabinose to obtain a plurality of single colonies. Then, they were applied to the LB agar medium containing 12.5 mg/L of tetracycline and 40 μg/mL of kanamycin, and cultured overnight at 34° C. A strain confirmed to be a strain in which the tetracycline resistance gene and the kanamycin resistance gene were removed by confirming that it could not grow was obtained The obtained strain was applied to the LB agar medium containing 10% sucrose and 1 mM IPTG to remove the RSFRedIX plasmid to obtain ΔSC17(0), ΔbudABCΔadhEΔldhA P4071-pyc strain. This strain was designated as YDSP24 strain.

<7-3> Construction of pSTV28-yjjPB

PCR was performed in a conventional manner by using the genomic DNA of the *E. coli* W3110 strain (ATCC 27325) as the template, and the synthetic DNAs of SEQ ID NOS: 99 and 100 as the primers to obtain a DNA fragment containing the yjjPB genes. The obtained DNA fragment was inserted into the pSTV28 vector treated with BamHI and PstI using In Fusion HD Cloning Kit (Clontech). The obtained plasmid for expression of the *E. coli* yjjPB genes was designated as pSTV28-yjjPB.

<7-4> Construction of *P. ananatis* YDSP27 Strain and YDSP26 Strain pSTV28-yjjPB constructed by the aforementioned method was introduced into the *P. ananatis* YDSP24 strain, to thereby construct a strain that expresses yjjPB derived from *E. coli*, which was designated as YDSP27. Furthermore, pSTV28 was introduced into the *P. ananatis* YDSP24 strain, to thereby construct a vector control, which was designated as YDSP26.

Specifically, the YDSP24 strain was cultured overnight in the LB liquid medium. Then, the culture broth (100 μL) was inoculated into fresh LB liquid medium (4 mL), and shaking culture was performed at 34° C. for 3 hours. The cells were collected, washed 3 times with 10% glycerol, and used as competent cells. pSTV28-yjjPB or pSTV28 was introduced into the competent cells by electroporation. The electroporation was performed by using GENE PULSER II (BioRad) under the conditions of an electric field intensity of 20 kV/cm, capacitor capacity of 25 μF, and resistance of 200Ω. The cells were cultured for 2 hours in the SOC medium (20 g/L of Bacto tryptone, 5 g/L of yeast extract, 0.5 g/L of NaCl, 10 g/L of glucose), then applied to the LB agar medium containing 40 mg/L of chloramphenicol, and cultured for 16 hours. As a result, a transformant showing chloramphenicol resistance was obtained from each medium, and thus SC17(0)ΔbudABCΔadhEΔldhAp4071-pyc/pSTV28-yjjPB strain (YDSP27 strain), and SC17(0)ΔbudABCΔadhEΔldhAp4071-pyc/pSTV28 strain (YDSP26 strain) were obtained.

<7-5> Evaluation of Succinic Acid-Producing Ability Under Anaerobic Condition

Then, succinic acid-producing abilities of these strains were evaluated. These strains were each cultured overnight at 34° C. on an LBGM9 agar medium plate containing 25 mg/L of chloramphenicol. The obtained cells were washed three times with a 0.85% NaCl aqueous solution to prepare a cell suspension showing an OD600 of 100. This cell suspension (0.1 ml) was inoculated into 1.3 mL of a succinic acid production medium contained in a 1.5 ml-volume tube (Eppendorf tube), and shaking culture was performed at 34° for 48 hours on an Eppendorf tube shaker (Thermomixer Comfort, Eppendorf) at 1400 rpm. The composition of the succinic acid production medium is shown below.

Composition of succinic acid production medium:

Group A:

| Glucose | 20 g/L |
| --- | --- |
| MgSO$_4$•7H$_2$O | 1.0 g/L |

Group B:

| (NH$_4$)$_2$SO$_4$ | 1.0 g/L |
| --- | --- |
| KH$_2$PO$_4$ | 1.0 g/L |
| Yeast extract | 2.0 g/L |
| FeSO$_4$•7H$_2$O | 0.01 g/L |
| MnSO$_4$•5H$_2$O | 0.01 g/L |
| Biotin | 0.001 g/L |

(pH was not adjusted)

Group C:

| CaCO$_3$ | 50 g/L |
| --- | --- |

The components of the groups A and B were each sterilized in an autoclave at 115° C. for 10 minute, the component of Group C was sterilized with hot air at 180° C. for 3 hours, then they were mixed, and chloramphenicol was added to the mixture at 25 mg/L.

The results are shown in Table 10. As compared with the YDSP26 strain as the control, the succinic acid carbon yield increased in the YDSP27 strain, in which the yjjPB genes of *E. coli* were expressed. These results revealed that, by amplifying the yjjPB genes in *P. ananatis*, succinic acid carbon yield thereof is improved.

TABLE 10

Influence of yjjPB gene amplification in *P. ananatis* on succinic acid production under anaerobic condition

| | Succinic acid carbon yield (%) |
|---|---|
| SC17(0)ΔbudABCΔadhEΔldhAp4071-pyc/pSTV28 | 34.7 ± 2.22 |
| SC17(0)ΔbudABCΔadhEΔldhAp4071-pyc/pSTV28-yjjPB | 38.3 ± 2.36 |

<Example 8> Evaluation of effect of yjjPB Amplification on succinic Acid Production by *E. aerogenes* Under Anaerobic Condition <8-1> Construction of *E. aerogenes* ES06ΔsdhAΔyeeAΔynfMΔyjjPB

*E. aerogenes* ES06ΔsdhAΔyeeAΔynfMΔyjjPB strain deficient in the yjjPB genes was constructed from the *E. aerogenes* ES06ΔsdhAΔyeeAΔynfM strain by the λ-red method. Specifically, PCR was performed by using the primers shown as SEQ ID NO: 132 and 133, and pMW118-attL-Km$^r$-attR as the template to amplify a fragment having sequences of 50 bp complementary to an internal sequence of the N-terminus side of the yjjP gene or an internal sequence of the C-terminus side of the yjjB gene of *Enterobacter aerogenes* at the respective ends, and the kanamycin resistance gene between the attL and attR sequences of k phage. ES06ΔsdhAΔyeeAΔynfM/RSFRedIX strain obtained by introducing RSFRedIX into the ES06ΔsdhAΔyeeAΔynfM strain by electroporation was cultured overnight in the LB liquid medium, the culture broth (1 mL) was inoculated into the LB liquid medium (100 mL) containing IPTG at a final concentration of 1 mM and 25 mg/L of chloramphenicol, and shaking culture was performed at 34° C. for 3 hours. The cells were collected, then washed 3 times with 10% glycerol, and used as competent cells. The amplified PCR fragment was purified by using Wizard PCR Prep (Promega), and introduced into the competent cells by electroporation. The electroporation was performed by using GENE PULSER II (BioRad) under the conditions of an electric field intensity of 20 kV/cm, capacitor capacity of 25 μF, and resistance of 200Ω. By selection on the LB agar medium containing 40 mg/L of kanamycin, ES06ΔsdhAΔyeeAΔynfMΔyjjPB::Km/RSFRedIX strain was obtained. This strain was purified on the LB agar medium containing 25 mg/L of chloramphenicol and 10 mM arabinose to obtain a plurality of single colonies. Then, they were applied to the LB agar medium containing 40 μg/mL of kanamycin, and cultured overnight at 34° C. A strain confirmed to be a strain in which the kanamycin resistance gene was removed by confirming that it could not grow was obtained. The obtained strain was applied to the LB agar medium containing 10% sucrose and 1 mM IPTG to remove the RSFRedIX plasmid to obtain ES06ΔsdhAΔyeeAΔynfMΔyjjPB strain.

<8-2> Construction of *E. aerogenes* Strain for Evaluation

The pSTV28 vector or the pSTV28-AeyjjPB plasmid was introduced into the ES06ΔsdhAΔyeeAΔynfM strain and the ES06ΔsdhAΔyeeAΔynfMΔyjjPB strain by an electroporation, the resulting strains were subjected to selection on the LB agar medium containing 25 mg/L of chloramphenicol, and the selected strains were purified on the LBGM9 agar medium to obtain ES06ΔsdhAΔyeeAΔynfM/pSTV28 strain as a control strain, ES06ΔsdhAΔyeeAΔynfMΔyjjPB/pSTV28 strain as a yeB-deficient strain, ES06ΔsdhAΔyeeAΔynfM/pSTV28-AeyjjPB strain and ES06ΔsdhAΔyeeAΔynfMΔyjjPB/pSTV28-AeyjjPB strain as dicarboxylic acid efflux carrier gene-amplified strains.

<8-3> Evaluation of Succinic Acid-Producing Ability

Then, succinic acid-producing abilities of these strains were evaluated. These strains were each cultured overnight at 34° C. on an LBGM9 agar medium plate containing 25 mg/L of chloramphenicol. Then, the plate was put into AnaeroPack (Mitsubishi Gas Chemical, product number A-04), and culture was continued at 37° C. for 2 hours under an anaerobic condition, and the obtained cells were used as seed cells. The seed cells on one plate were once suspended in 0.7 ml of physiological saline for washing, and re-suspended in physiological saline at an OD of 100 at 620 nm. This cell suspension was put into a 1.5 ml-volume Eppendorf tube in a volume of 300 μl together with 900 μl of a succinic acid production medium (drug free), the tube was sealed with a stopper, and the cells were cultured at 34° C. for 24 hours with shaking at 1200 rpm on an Eppendorf tube shaker. The composition of the succinic acid production medium is shown below.

Composition of succinic acid production medium:

Group A:

| | |
|---|---|
| $(NH_4)_2SO_4$ | 1 g/L |
| $KH_2PO_4$ | 1 g/L |
| $FeSO_4 \cdot 7H_2O$ | 10 mg/L |
| $MnSO_4 \cdot 5H_2O$ | 10 mg/L |
| Yeast extract | 2 g/L |

(adjusted to pH 7.0 with KOH)

Group B:

| | |
|---|---|
| Glucose | 40 g/L |
| $MgSO_4 \cdot 7H_2O$ | 1 g/L |

The components of the groups A and B were each sterilized in an autoclave at 115° C. for 10 minute, and cooled, and then $CaCO_3$ defined in Japanese Pharmacopoeia, which was sterilized with hot air at 180° C. for 3 hours or longer, and left to cool, was added at 50 g/L.

The results are shown in Table 11. As compared with the ES06ΔsdhAΔyeeAΔynfM/pSTV28 strain as the control, the succinic acid yield increased in the ES06ΔsdhAΔyeeAΔynfM/pSTV28-AeyjjPB strain, in which the yjjPB genes of *E. aerogenes* were expressed. In the ES06ΔsdhAΔyeeAΔynfMΔyjjPB/pSTV28 strain deficient in the yjjPB genes, the succinic acid yield decreased by about 5% as compared with the control strain, but by introducing pSTV28-AeyjjPB into this strain, the succinic acid yield was recovered to a level equivalent to that of the ES06ΔsdhAΔyeeAΔynfM/pSTV28-AeyjjPB strain. These results revealed that amplification of the yjjPB genes improves yield of succinic acid in *E. aerogenes* even under an anaerobic condition.

TABLE 11

Influence of yjjPB gene amplification in *E. aerogenes* on succinic acid production under anaerobic condition

| | $OD_{620nm}$ | Consumed gluclose (g/L) | Succinate (g/L) | Fumarate (g/L) | Malate (g/L) | Acetate (g/L) | Succinate yield (%) |
|---|---|---|---|---|---|---|---|
| ES06ΔsdhAΔyeeAΔynfM/pSTV28 | 27 ± 0.87 | 11 ± 0.24 | 5.7 ± 0.15 | 0.63 ± 0.026 | 0.21 ± 0.029 | 0.72 ± 0.021 | 53 ± 0.95 |
| ES06ΔsdhAΔyeeAΔynfM/pSTV28-AeyjjPB | 29 ± 0.62 | 9.6 ± 0.20 | 5.8 ± 0.82 | 1.3 ± 0.018 | 0.34 ± 0.019 | 0.43 ± 0.040 | 60 ± 0.60 |
| ES06ΔsdhAΔyeeAΔynfMΔyjjPB/pSTV28 | 23 ± 1.6 | 9.1 ± 0.50 | 4.3 ± 0.061 | 0.60 ± 0.010 | N.D. | 0.56 ± 0.012 | 48 ± 2.1 |
| ES06ΔsdhAΔyeeAΔynfMΔyjjPB/pSTV28-AeyjjPB | 27 ± 1.8 | 93 ± 0.51 | 5.4 ± 0.30 | 1.3 ± 0.015 | 0.33 ± 0.034 | 0.42 ± 0.046 | 57 ± 2.6 |

INDUSTRIAL APPLICABILITY

According to the present invention, dicarboxylic acid-producing ability of bacteria can be improved, and dicarboxylic acids can be efficiently produced.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

EXPLANATION OF SEQUENCE LISTING

SEQ ID NO: 1: Nucleotide sequence of yeeA gene of *E. coli* MG1655
SEQ ID NO: 2: Amino acid sequence of YeeA protein of *E. coli* MG1655
SEQ ID NO: 3: Nucleotide sequence of yeeA gene of *Pantoea ananatis*
SEQ ID NO: 4: Amino acid sequence of YeeA protein of *Pantoea ananatis* AJ13355
SEQ ID NO: 5: Nucleotide sequence of yeeA gene of *Enterobacter aerogenes* AJ110637
SEQ ID NO: 6: Amino acid sequence of YeeA protein of *Enterobacter aerogenes* AJ110637
SEQ ID NO: 7: Nucleotide sequence of ynfM gene of *E. coli* MG1655
SEQ ID NO: 8: Amino acid sequence of YnfM protein of *E. coli* MG1655
SEQ ID NO: 9: Nucleotide sequence of ynfM gene of *Pantoea ananatis* AJ13355
SEQ ID NO: 10: Amino acid sequence of YnfM protein of *Pantoea ananatis* AJ13355
SEQ ID NO: 11: Nucleotide sequence of ynfM gene of *Enterobacter aerogenes* AJ110637
SEQ ID NO: 12: Amino acid sequence of YnfM protein of *Enterobacter aerogenes* AJ110637
SEQ ID NO: 13: Nucleotide sequence of ynfM gene of *Corynebacterium glutamicum* ATCC 13032
SEQ ID NO: 14: Amino acid sequence of YnfM protein of *Corynebacterium glutamicum* ATCC 13032
SEQ ID NO: 15: Nucleotide sequence of ynfM gene of *Corynebacterium glutamicum* ATCC 13869
SEQ ID NO: 16: Amino acid sequence of YnfM protein of *Corynebacterium glutamicum* ATCC 13869
SEQ ID NO: 17: Nucleotide sequence of yjjP gene of *E. coli* MG1655
SEQ ID NO: 18: Amino acid sequence of YjjP protein of *E. coli* MG1655
SEQ ID NO: 19: Nucleotide sequence of yjjP gene of *Enterobacter aerogenes* AJ110637
SEQ ID NO: 20: Amino acid sequence of YjjP protein of *Enterobacter aerogenes* AJ110637
SEQ ID NO: 21: Nucleotide sequence of yjjB gene of *E. coli* MG1655
SEQ ID NO: 22: Amino acid sequence of YjjB protein of *E. coli* MG1655
SEQ ID NO: 23: Nucleotide sequence of yjjB gene of *Enterobacter aerogenes* AJ110637
SEQ ID NO: 24: Amino acid sequence of YjjB protein of *Enterobacter aerogenes* AJ110637
SEQ ID NOS: 25 to 48: Primers
SEQ ID NO: 49: Nucleotide sequence of CAD gene of *Aspergillus terreus* optimized for codon usage of *E. coli*
SEQ ID NO: 50: Nucleotide sequence of pckA gene of *Actinobacillus succinogenes* 130Z
SEQ ID NO: 51: Amino acid sequence of PckA protein of *Actinobacillus succinogenes* 130Z
SEQ ID NOS: 52 to 66: Primers
SEQ ID NO: 67: Nucleotide sequence of Ptac1000 promoter
SEQ ID NOS: 68 to 100: Primers
SEQ ID NO: 101: Nucleotide sequence of ldhA gene of *Pantoea ananatis* AJ13355
SEQ ID NO: 102: Amino acid sequence of LdhA protein of *Pantoea ananatis* AJ13355
SEQ ID NO: 103: Nucleotide sequence of adhE gene of *Pantoea ananatis* AJ13355
SEQ ID NO: 104: Amino acid sequence of AdhE protein of *Pantoea ananatis* AJ13355
SEQ ID NO: 105: Nucleotide sequence of budB gene of *Pantoea ananatis* AJ13355
SEQ ID NO: 106: Amino acid sequence of BudB protein of *Pantoea ananatis* AJ13355
SEQ ID NO: 107: Nucleotide sequence of budA gene of *Pantoea ananatis* AJ13355
SEQ ID NO: 108: Amino acid sequence of BudA protein of *Pantoea ananatis* AJ13355
SEQ ID NO: 109: Nucleotide sequence of budC gene of *Pantoea ananatis* AJ13355
SEQ ID NO: 110: Amino acid sequence of BudC protein of *Pantoea ananatis* AJ13355
SEQ ID NO: 111: Nucleotide sequence of sdhA gene of *Pantoea ananatis* AJ13355
SEQ ID NO: 112: Amino acid sequence of SdhA protein of *Pantoea ananatis* AJ13355
SEQ ID NO: 113: Nucleotide sequence of mdh gene of *Pantoea ananatis* AJ13355
SEQ ID NO: 114: Amino acid sequence of Mdh protein of *Pantoea ananatis* AJ13355

SEQ ID NO: 115: Nucleotide sequence of mqo1 gene of *Pantoea ananatis* AJ13355
SEQ ID NO: 116: Amino acid sequence of Mqo1 protein of *Pantoea ananatis* AJ13355
SEQ ID NO: 117: Nucleotide sequence of mqo2 gene of *Pantoea ananatis* AJ13355
SEQ ID NO: 118: Amino acid sequence of Mqo2 protein of *Pantoea ananatis* AJ13355
SEQ ID NO: 119: Nucleotide sequence of sfcA gene of *Pantoea ananatis* AJ13355
SEQ ID NO: 120: Amino acid sequence of SfcA protein of *Pantoea ananatis* AJ13355
SEQ ID NO: 121: Nucleotide sequence of maeB gene of *Pantoea ananatis* AJ13355
SEQ ID NO: 122: Amino acid sequence of MaeB protein of *Pantoea ananatis* AJ13355
SEQ ID NO: 123: Nucleotide sequence of aceB gene of *Pantoea ananatis* AJ13355
SEQ ID NO: 124: Amino acid sequence of AceB protein of *Pantoea ananatis* AJ13355
SEQ ID NO: 125: Nucleotide sequence of aceA gene of *Pantoea ananatis* AJ13355
SEQ ID NO: 126: Amino acid sequence of AceA protein of *Pantoea ananatis* AJ13355
SEQ ID NO: 127: Nucleotide sequence of aceK gene of *Pantoea ananatis* AJ13355
SEQ ID NO: 128: Amino acid sequence of AceK protein of *Pantoea ananatis* AJ13355
SEQ ID NO: 129: Nucleotide sequence of sucA gene of *Pantoea ananatis* AJ13355
SEQ ID NO: 130: Amino acid sequence of SucA protein of *Pantoea ananatis* AJ13355
SEQ ID NO: 131: Amino acid sequence of CAD of *Aspergillus terreus*
SEQ ID NOS: 132 and 133: Primers

The invention claimed is:

1. A method for producing a dicarboxylic acid, the method comprising:
   culturing a bacterium having a dicarboxylic acid-producing ability in a medium to produce and accumulate the dicarboxylic acid in the medium; and
   collecting the dicarboxylic acid from the medium, wherein the bacterium has been modified to increase the expression of a gene selected from the group consisting of yeeA, ynfM, yjjP, yjjB, and combinations thereof as compared to that in the non-modified bacterium;
   wherein the expression of the gene(s) is increased by increasing the copy number of the gene(s) and/or modifying an expression control sequence of the gene(s);
   wherein the yeeA gene is a DNA selected from the group consisting of:
      (1A) a DNA encoding a protein comprising the amino acid sequence of SEQ ID NO: 2, 4, or 6,
      (1B) a DNA encoding a protein comprising the amino acid sequence of SEQ ID NO: 2, 4, or 6, but which includes substitution, deletion, insertion or addition of 1 to 10 amino acid residues, and wherein said protein has a dicarboxylic acid-secreting activity,
      (1C) a DNA encoding a protein comprising an amino acid sequence having an identity of 90% or more to the amino acid sequence of SEQ ID NO: 2, 4, or 6, and wherein said protein has a dicarboxylic acid-secreting activity,
      (1D) a DNA comprising the nucleotide sequence of SEQ ID NO: 1, 3, or 5, and
      (1E) a DNA that hybridizes under stringent conditions of 0.1×SSC, 0.1% SDS at 60° C. with the full-length complement of the polynucleotide of SEQ ID NO: 1, 3, or 5, and encoding a protein having a dicarboxylic acid-secreting activity;
   wherein the ynfM gene is a DNA selected from the group consisting of:
      (2A) a DNA encoding a protein comprising the amino acid sequence of SEQ ID NO: 8, 10, 12, 14, or 16,
      (2B) a DNA encoding a protein comprising the amino acid sequence of SEQ ID NO: 8, 10, 12, 14, or 16, but which includes substitution, deletion, insertion or addition of 1 to 10 amino acid residues, and wherein said protein has a dicarboxylic acid-secreting activity,
      (2C) a DNA encoding a protein comprising an amino acid sequence having an identity of 90% or more to the amino acid sequence of SEQ ID NO: 8, 10, 12, 14, or 16, and wherein said protein has a dicarboxylic acid-secreting activity,
      (2D) a DNA comprising the nucleotide sequence of SEQ ID NO: 7, 9, 11, 13, or 15, and
      (2E) a DNA that hybridizes under stringent conditions of 0.1×SSC, 0.1% SDS at 60° C. with the full-length complement of the polynucleotide of SEQ ID NO: 7, 9, 11, 13, or 15, and encoding a protein having a dicarboxylic acid-secreting activity;
   wherein the yjjP gene is a DNA selected from the group consisting of:
      (3A) a DNA encoding a protein comprising the amino acid sequence of SEQ ID NO: 18 or 20,
      (3B) a DNA encoding a protein comprising the amino acid sequence of SEQ ID NO: 18 or 20, but which includes substitution, deletion, insertion or addition of 1 to 10 amino acid residues, and wherein said protein has a dicarboxylic acid-secreting activity,
      (3C) a DNA encoding a protein comprising an amino acid sequence having an identity of 90% or more to the amino acid sequence of SEQ ID NO: 18 or 20, and wherein said protein has a dicarboxylic acid-secreting activity,
      (3D) a DNA comprising the nucleotide sequence of SEQ ID NO: 17 or 19, and
      (3E) a DNA that hybridizes under stringent conditions of 0.1×SSC, 0.1% SDS at 60° C. with the full-length complement of the polynucleotide of SEQ ID NO: 17 or 19, and encoding a protein having a dicarboxylic acid-secreting activity;
   wherein the yjjB gene is a DNA selected from the group consisting of:
      (4A) a DNA encoding a protein comprising the amino acid sequence of SEQ ID NO: 22 or 24,
      (4B) a DNA encoding a protein comprising the amino acid sequence of SEQ ID NO: 22 or 24, but which includes substitution, deletion, insertion or addition of 1 to 10 amino acid residues, and wherein said protein has a dicarboxylic acid-secreting activity,
      (4C) a DNA encoding a protein comprising an amino acid sequence having an identity of 90% or more to the amino acid sequence of SEQ ID NO: 22 or 24, and wherein said protein has a dicarboxylic acid-secreting activity,
      (4D) a DNA comprising the nucleotide sequence of SEQ ID NO: 21 or 23, and
      (4E) a DNA that hybridizes under stringent conditions of 1×SSC, 0.1% SDS at 60° C. with the full-length complement of the polynucleotide of SEQ ID NO: 21 or 23, and encoding a protein having a dicarboxylic acid-secreting activity;
   provided that the bacterium is a *Pantoea* bacterium, and *Enterobacter* bacterium, or a coryneform bacterium when the expression of the ynfM is increased.

2. The method according to claim 1, wherein the bacterium is a bacterium belonging to the family Enterobacteriaceae, or a coryneform bacterium.

3. The method according to claim 1, wherein the bacterium is a *Pantoea* bacterium or an *Enterobacter* bacterium.

4. The method according to claim 1, wherein the bacterium is *Pantoea ananatis* or *Enterobacter aerogenes*.

5. The method according to claim 1, wherein the bacterium is a *Corynebacterium* bacterium.

6. The method according to claim 1, wherein the bacterium is *Corynebacterium glutamicum*.

7. The method according to claim 1, wherein the dicarboxylic acid is selected from the group consisting of α-ketoglutaric acid, malic acid, fumaric acid, succinic acid, itaconic acid, and combinations thereof.

* * * * *

```
                        SEQUENCE LISTING

<160> NUMBER OF SEQ ID NOS: 133

<210> SEQ ID NO 1
<211> LENGTH: 1059
<212> TYPE: DNA
<213> ORGANISM: Escherichia coli

<400> SEQUENCE: 1
gtgcgtgccg ataagtcatt aagcccgttt gaaatccggg tataccgcca ttaccgcatt      60
gtgcatggta ctcgggtcgc gctggcattc ctgctcactt ttctcattat ccgcctgttt     120
actatcccgg aaagcacctg gccgctggtc accatggtgg tgattatggg gccaatctcg     180
ttctggggta acgttgtccc tcgcgccttt gagcgtattg gcggtacggt gttgggttcg     240
attttaggtc ttatcgctct gcaactggag ttaatctcgt taccgctgat gttagtctgg     300
tgcgcggcgg ccatgttcct ttgcggttgg ctggcgctgg caagaaaacc gtatcaaggt     360
ttattgattg gggtgacgct ggcaattgtt gtgggttccc cgacaggtga aattgatacg     420
gcgttatggc gaagcggcga tgtgatcctc ggctctttac tggcaatgtt gtttaccggt     480
atctggccac aacgggcgtt catccactgg cgcattcaac tggcgaaaag tctgaccgag     540
tataatcggg tctatcaatc tgcattctca ccgaacttac tcgaacgccc acgtctggaa     600
agccatctac aaaaactcct gaccgatgcc gtgaaaatgc gtggactgat tgcgcccgcc     660
agcaaagaaa cccgtattcc aaaatcgata tatgaaggta tccagaccat taaccgcaat     720
ctggtttgta tgctggagtt gcaaatcaat gcatactggg ccacgcgccc cagccatttc     780
gtgttattga acgcgcaaaa acttcgtgat acccagcaca tgatgcagca aatactgctg     840
agccttgttc atgcgctgta cgaaggtaat ccgcagccgg tttttgccaa tacggaaaaa     900
ttgaacgatg ctgtggaaga gctgcgtcag ttgctcaata accaccatga cctgaaggtt     960
gtggaaacac caatctatgg ttatgtgtgg ctgaacatgg aaacggcgca tcagcttgag    1020
ttgctatcga atctgatttg ccgggccttg cgcaaataa                           1059

<210> SEQ ID NO 2
<211> LENGTH: 352
<212> TYPE: PRT
<213> ORGANISM: Escherichia coli

<400> SEQUENCE: 2

Met Arg Ala Asp Lys Ser Leu Ser Pro Phe Glu Ile Arg Val Tyr Arg
1               5                   10                  15
```

His Tyr Arg Ile Val His Gly Thr Arg Val Ala Leu Ala Phe Leu Leu
            20                  25                  30

Thr Phe Leu Ile Ile Arg Leu Phe Thr Ile Pro Glu Ser Thr Trp Pro
        35                  40                  45

Leu Val Thr Met Val Val Ile Met Gly Pro Ile Ser Phe Trp Gly Asn
 50                  55                  60

Val Val Pro Arg Ala Phe Glu Arg Ile Gly Gly Thr Val Leu Gly Ser
 65                  70                  75                  80

Ile Leu Gly Leu Ile Ala Leu Gln Leu Glu Leu Ile Ser Leu Pro Leu
                85                  90                  95

Met Leu Val Trp Cys Ala Ala Met Phe Leu Cys Gly Trp Leu Ala
            100                 105                 110

Leu Gly Lys Lys Pro Tyr Gln Gly Leu Leu Ile Gly Val Thr Leu Ala
        115                 120                 125

Ile Val Val Gly Ser Pro Thr Gly Glu Ile Asp Thr Ala Leu Trp Arg
130                 135                 140

Ser Gly Asp Val Ile Leu Gly Ser Leu Leu Ala Met Leu Phe Thr Gly
145                 150                 155                 160

Ile Trp Pro Gln Arg Ala Phe Ile His Trp Arg Ile Gln Leu Ala Lys
                165                 170                 175

Ser Leu Thr Glu Tyr Asn Arg Val Tyr Gln Ser Ala Phe Ser Pro Asn
            180                 185                 190

Leu Leu Glu Arg Pro Arg Leu Glu Ser His Leu Gln Lys Leu Leu Thr
        195                 200                 205

Asp Ala Val Lys Met Arg Gly Leu Ile Ala Pro Ala Ser Lys Glu Thr
210                 215                 220

Arg Ile Pro Lys Ser Ile Tyr Glu Gly Ile Gln Thr Ile Asn Arg Asn
225                 230                 235                 240

Leu Val Cys Met Leu Glu Leu Gln Ile Asn Ala Tyr Trp Ala Thr Arg
                245                 250                 255

Pro Ser His Phe Val Leu Leu Asn Ala Gln Lys Leu Arg Asp Thr Gln
            260                 265                 270

His Met Met Gln Gln Ile Leu Leu Ser Leu Val His Ala Leu Tyr Glu
        275                 280                 285

Gly Asn Pro Gln Pro Val Phe Ala Asn Thr Glu Lys Leu Asn Asp Ala
290                 295                 300

Val Glu Glu Leu Arg Gln Leu Leu Asn Asn His His Asp Leu Lys Val
305                 310                 315                 320

Val Glu Thr Pro Ile Tyr Gly Tyr Val Trp Leu Asn Met Glu Thr Ala
                325                 330                 335

His Gln Leu Glu Leu Leu Ser Asn Leu Ile Cys Arg Ala Leu Arg Lys
            340                 345                 350

<210> SEQ ID NO 3
<211> LENGTH: 1056
<212> TYPE: DNA
<213> ORGANISM: Pantoea ananatis

<400> SEQUENCE: 3
ttgcgctctg ataagcccat ctctaatctg gaattctggt tatatcgcca ttaccgtagc    60
gtgcacggct tgcgcatcgc ggtggcgttt cttttttgcct ttttgtttgt gcggatgacc   120
ggcattcccg aaggcacctg gccgctgatt acgctggtgg tggtgatggg gccgatctcc   180
acgtggggca atgtgttttcc ccgcgccatt cagcgcattg gcggcacgat tgccgggtca   240

```
atttcgggat tgattgcgct caagctggag atgatttcgc taccgggcat gctggcctgg      300
tgcgcgctga tcatgtttat cagcggctat ctgaccctgg aaagcatcc  ctatatggcg      360 ctgttgattg cattacgct  ctgcgtagtg gtcggcgcgc caatgggga  tttcaccgtc      420 gccatgtggc gtggcggcga tgtgatttta ggctcgctgc tggcgctgat atttaccgct      480
gtctgggcac agcgcgccta cattcactgg cgtatccagc tttcggatac gctgggcgag      540
atggcaaaaa tctatcatgc aggttttttcc gctaacctgg tggaaaagcc gcgactgaat     600
aagccctttg gaagttgct  ctccagcgtc atcaaaatgc gcgcgctgtt ggagccgtcc      660
agcaaagaaa cgcgtattcc taaatcggta tttgaagcga ttcagaccat aaaccgtaat      720
atggtgtaca ccattgagat gcaaattaat gcctggtggg catcgaggga aagccatctg      780
attatgctga atgcgccgac gctgcgccgt actcagcaga tgacggaaaa cgcgctacga      840
acgttgtcgg agatggcggt gaaaggggaa acctatgaca tcatcgcggc caaccatgag      900
ttaacggaaa tcgtcaatga acttaagcag ttgatcgcca gcggcagtga ccgtctggag      960
gaaacgccaa tttatggcta tgtctggttg agtctggagc tggcgaagca actggagcgc     1020
atgacggact tactgcgtct ggcgctgcgt aaataa                               1056
```

<210> SEQ ID NO 4
<211> LENGTH: 351
<212> TYPE: PRT
<213> ORGANISM: Pantoea ananatis

<400> SEQUENCE: 4

```
Met Arg Ser Asp Lys Pro Ile Ser Asn Leu Glu Phe Trp Leu Tyr Arg
1               5                   10                  15

His Tyr Arg Ser Val His Gly Leu Arg Ile Ala Val Ala Phe Leu Phe
            20                  25                  30

Ala Phe Leu Phe Val Arg Met Thr Gly Ile Pro Glu Gly Thr Trp Pro
        35                  40                  45

Leu Ile Thr Leu Val Val Met Gly Pro Ile Ser Thr Trp Gly Asn
    50                  55                  60

Val Phe Pro Arg Ala Ile Gln Arg Ile Gly Gly Thr Ile Ala Gly Ser
65                  70                  75                  80

Ile Ser Gly Leu Ile Ala Leu Lys Leu Glu Met Ile Ser Leu Pro Gly
                85                  90                  95

Met Leu Ala Trp Cys Ala Leu Ile Met Phe Ile Ser Gly Tyr Leu Thr
            100                 105                 110

Leu Gly Lys His Pro Tyr Met Ala Leu Leu Ile Gly Ile Thr Leu Cys
        115                 120                 125

Val Val Val Gly Ala Pro Met Gly Asp Phe Thr Val Ala Met Trp Arg
    130                 135                 140

Gly Gly Asp Val Ile Leu Gly Ser Leu Leu Ala Leu Ile Phe Thr Ala
145                 150                 155                 160

Val Trp Ala Gln Arg Ala Tyr Ile His Trp Arg Ile Gln Leu Ser Asp
                165                 170                 175

Thr Leu Gly Glu Met Ala Lys Ile Tyr His Ala Gly Phe Ser Ala Asn
            180                 185                 190

Leu Val Glu Lys Pro Arg Leu Asn Lys Pro Phe Gly Lys Leu Leu Ser
        195                 200                 205

Ser Val Ile Lys Met Arg Ala Leu Leu Glu Pro Ser Ser Lys Glu Thr
    210                 215                 220
```

```
Arg Ile Pro Lys Ser Val Phe Glu Ala Ile Gln Thr Ile Asn Arg Asn
225                 230                 235                 240

Met Val Tyr Thr Ile Glu Met Gln Ile Asn Ala Trp Trp Ala Ser Arg
                245                 250                 255

Glu Ser His Leu Ile Met Leu Asn Ala Pro Thr Leu Arg Arg Thr Gln
            260                 265                 270

Gln Met Thr Glu Asn Ala Leu Arg Thr Leu Ser Glu Met Ala Val Lys
        275                 280                 285

Gly Glu Thr Tyr Asp Ile Ile Ala Ala Asn His Glu Leu Thr Glu Ile
    290                 295                 300

Val Asn Glu Leu Lys Gln Leu Ile Ala Ser Gly Ser Asp Arg Leu Glu
305                 310                 315                 320

Glu Thr Pro Ile Tyr Gly Tyr Val Trp Leu Ser Leu Glu Leu Ala Lys
                325                 330                 335

Gln Leu Glu Arg Met Thr Asp Leu Leu Arg Leu Ala Leu Arg Lys
            340                 345                 350

<210> SEQ ID NO 5
<211> LENGTH: 1107
<212> TYPE: DNA
<213> ORGANISM: Enterobacter aerogenes

<400> SEQUENCE: 5
atgaaaaaag cggctacaat tggccttttc tgtttgccgg agcaggccgt gcgcgctgat      60
aaatcactta agccatttga gatccgtctg tatcgtcatt accgaattgt gcacggtatc     120
cgcatcgcgc tggcttttgt cctgaccttc ctgctggtgc gtctgctgga cgtgccggag     180
ggcacctggc ctctgatcac cctggtggtg gtgatggggc tatctctttt ctggggcaat     240
gtggtgccgc gggccttcga acgtattggc ggcactatcc tcggttcggt gctggggctg     300
gtggcgctca aactcgaact tatctcactg ccaattatgg tgctgtggtg cgcggtggcg     360
atgttcctct cgcgctggct ggcgctcggc aaacggccct accaggcgtt gctgatcggc     420
attacgctgg cagtggtggt gggcgcgccg ccgggcgata tgaacaccgc gttgtggcga     480
agcggcgatg ttatctttgg ttcactgttg gcgatgctgt ttaccggtat ctggccgcag     540
cgggcgtttt tgcactggcg catccagatg gcgaattatg tcacaacgtt taatcggctg     600
tatcaggccg ttttttcgcc gaatctggtt gagcgcccgc ggctggaaaa acatcttcag     660
aaagcgctca atgacgtggt gaaaatgcgt gggttgataa ccccggccag caaagaaacg     720
catattcaga aagcaatctt cgaagccatc cagaccgtca gccgtaatct ggtatgcatg     780
ttggaactgc agatcaacgc ttactgggcc tctcgccagg ccattttgt gatgcttaac     840 gcccagactt tgcgcgaaac ccaacagatg acccagcaaa cgttgctgac catcgcccat     900
gccttgtatg agggaaaccc gcagccggta cgcgccaaca ccgagaaact caacgagatt     960
gtggtcgagt gcggcagct tatcaaagag catcaggacg ataatctgtc ggaaacgccg    1020
attcacggct atgtttggct gaccattgag ctggcgcgcc agcttgagct gctgtcgcac    1080
cttatttgcc gcgcgctgcg caaataa                                        1107

<210> SEQ ID NO 6
<211> LENGTH: 368
<212> TYPE: PRT
<213> ORGANISM: Enterobacter aerogenes

<400> SEQUENCE: 6

Met Lys Lys Ala Ala Thr Ile Gly Leu Phe Cys Leu Pro Glu Gln Ala
```

```
  1               5                  10                 15
Val Arg Ala Asp Lys Ser Leu Lys Pro Phe Glu Ile Arg Leu Tyr Arg
            20                  25                 30
His Tyr Arg Ile Val His Gly Ile Arg Ile Ala Leu Ala Phe Val Leu
            35                  40                 45
Thr Phe Leu Leu Val Arg Leu Leu Asp Val Pro Glu Gly Thr Trp Pro
            50                  55                 60
Leu Ile Thr Leu Val Val Met Gly Pro Ile Ser Phe Trp Gly Asn
 65                  70                  75                 80
Val Val Pro Arg Ala Phe Glu Arg Ile Gly Gly Thr Ile Leu Gly Ser
                 85                  90                 95
Val Leu Gly Leu Val Ala Leu Lys Leu Glu Leu Ile Ser Leu Pro Ile
                100                 105                110
Met Val Leu Trp Cys Ala Val Ala Met Phe Leu Cys Gly Trp Leu Ala
                115                 120                125
Leu Gly Lys Arg Pro Tyr Gln Ala Leu Leu Ile Gly Ile Thr Leu Ala
            130                 135                 140
Val Val Gly Ala Pro Pro Gly Asp Met Asn Thr Ala Leu Trp Arg
145                 150                 155                 160
Ser Gly Asp Val Ile Phe Gly Ser Leu Leu Ala Met Leu Phe Thr Gly
                165                 170                 175
Ile Trp Pro Gln Arg Ala Phe Leu His Trp Arg Ile Gln Met Ala Asn
            180                 185                 190
Tyr Val Thr Thr Phe Asn Arg Leu Tyr Gln Ala Gly Phe Ser Pro Asn
            195                 200                 205
Leu Val Glu Arg Pro Arg Leu Glu Lys His Leu Gln Lys Ala Leu Asn
210                 215                 220
Asp Val Val Lys Met Arg Gly Leu Ile Thr Pro Ala Ser Lys Glu Thr
225                 230                 235                 240
His Ile Gln Lys Ala Ile Phe Glu Ala Ile Gln Thr Val Ser Arg Asn
            245                 250                 255
Leu Val Cys Met Leu Glu Leu Gln Ile Asn Ala Tyr Trp Ala Ser Arg
            260                 265                 270
Gln Gly His Phe Val Met Leu Asn Ala Gln Thr Leu Arg Glu Thr Gln
            275                 280                 285
Gln Met Thr Gln Gln Thr Leu Leu Thr Ile Ala His Ala Leu Tyr Glu
            290                 295                 300
Gly Asn Pro Gln Pro Val Arg Ala Asn Thr Glu Lys Leu Asn Glu Ile
305                 310                 315                 320
Val Val Glu Leu Arg Gln Leu Ile Lys Glu His Gln Asp Asp Asn Leu
                325                 330                 335
Ser Glu Thr Pro Ile His Gly Tyr Val Trp Leu Thr Ile Glu Leu Ala
            340                 345                 350
Arg Gln Leu Glu Leu Leu Ser His Leu Ile Cys Arg Ala Leu Arg Lys
            355                 360                 365

<210> SEQ ID NO 7
<211> LENGTH: 1254
<212> TYPE: DNA
<213> ORGANISM: Escherichia coli

<400> SEQUENCE: 7
gtgagccgta ctacaactgt tgatggcgct ccggcaagcg acactgacaa gcaaagcatt      60
tctcagccaa atcaatttat taaacgcggt acgccgcaat ttatgcgcgt caccctggcg     120
```

```
ctgttctctg ccggactggc aacatttgca cttctctatt gtgtgcagcc tatccttccg      180
gtgctttcgc aggagtttgg cttaaccccc gcgaacagta gtatttcact gtccatttcc      240
acggcgatgt tggctattgg tttgctgttt actggcccgc tatccgatgc cattggtcgc      300
aaaccagtga tggtcacggc gctactgttg gcctccattt gtacgttact ttcgacaatg      360
atgaccagct ggcacggcat tttgattatg cgcgccttga ttgggctttc gttaagtggc      420
gtggcagctg ttggcatgac ttatcttagc gaggaaatcc atcccagttt cgtgccttt       480
tcaatggggt tgtatatcag cggcaactca attggcggca tgagcggacg cttaattagc      540
ggtgtcttca cggacttttt caactggcga attgctctgg cggcaatcgg ttgtttcgcg      600
ctggcctcgg cgttgatgtt ctggaaaatc ctccctgaat cacgccattt cgcccgact       660
tcgctgcgcc ctaagacgtt gtttatcaac tttgtctgc actggcgtga ccggggatta      720
ccgttattgt tcgcagaagg cttttgtgg atggggtcgt tcgtcacgct gtttaattac      780
atcggctatc ggttgatgct ctcccctgg catgtcagtc aggccgtggt tggcttatta      840
tcgctggctt atttgaccgg tacatggagc tcacccaaag ccggaaccat gaccacccgc      900
tatgggcgtg gtccagtgat gttgttttcg acggggggtta tgctgtttgg tttactgatg      960
accttattca gctcgctgtg gctgatcttt gccggaatgt tactcttctc agcaggattc     1020
ttcgcagccc actcagtagc cagcagctgg atcggccccc gcgcaaaacg cgctaaaggc     1080
caggcctcct cgctgtatct gttcagttac tatctggggt cgagtattgc cgggacgctg     1140
ggtggtgttt tctggcataa ctatggctgg aacggcgtcg gcgcatttat tgctctgatg     1200
ctggtcattg ctctgctggt cgggacgcgt ttgcatcgtc gtctgcacgc ctga          1254
```

<210> SEQ ID NO 8
<211> LENGTH: 417
<212> TYPE: PRT
<213> ORGANISM: Escherichia coli

<400> SEQUENCE: 8

```
Met Ser Arg Thr Thr Val Asp Gly Ala Pro Ala Ser Asp Thr Asp
1               5                   10                  15

Lys Gln Ser Ile Ser Gln Pro Asn Gln Phe Ile Lys Arg Gly Thr Pro
            20                  25                  30

Gln Phe Met Arg Val Thr Leu Ala Leu Phe Ser Ala Gly Leu Ala Thr
        35                  40                  45

Phe Ala Leu Leu Tyr Cys Val Gln Pro Ile Leu Pro Val Leu Ser Gln
    50                  55                  60

Glu Phe Gly Leu Thr Pro Ala Asn Ser Ser Ile Ser Leu Ser Ile Ser
65                  70                  75                  80

Thr Ala Met Leu Ala Ile Gly Leu Leu Phe Thr Gly Pro Leu Ser Asp
                85                  90                  95

Ala Ile Gly Arg Lys Pro Val Met Val Thr Ala Leu Leu Leu Ala Ser
            100                 105                 110

Ile Cys Thr Leu Leu Ser Thr Met Met Thr Ser Trp His Gly Ile Leu
        115                 120                 125

Ile Met Arg Ala Leu Ile Gly Leu Ser Leu Ser Gly Val Ala Ala Val
    130                 135                 140

Gly Met Thr Tyr Leu Ser Glu Glu Ile His Pro Ser Phe Val Ala Phe
145                 150                 155                 160

Ser Met Gly Leu Tyr Ile Ser Gly Asn Ser Ile Gly Gly Met Ser Gly
                165                 170                 175
```

Arg Leu Ile Ser Gly Val Phe Thr Asp Phe Phe Asn Trp Arg Ile Ala
            180                 185                 190

Leu Ala Ala Ile Gly Cys Phe Ala Leu Ala Ser Ala Leu Met Phe Trp
        195                 200                 205

Lys Ile Leu Pro Glu Ser Arg His Phe Arg Pro Thr Ser Leu Arg Pro
210                 215                 220

Lys Thr Leu Phe Ile Asn Phe Arg Leu His Trp Arg Asp Arg Gly Leu
225                 230                 235                 240

Pro Leu Leu Phe Ala Glu Gly Phe Leu Met Gly Ser Phe Val Thr
            245                 250                 255

Leu Phe Asn Tyr Ile Gly Tyr Arg Leu Met Leu Ser Pro Trp His Val
            260                 265                 270

Ser Gln Ala Val Val Gly Leu Leu Ser Leu Ala Tyr Leu Thr Gly Thr
        275                 280                 285

Trp Ser Ser Pro Lys Ala Gly Thr Met Thr Thr Arg Tyr Gly Arg Gly
    290                 295                 300

Pro Val Met Leu Phe Ser Thr Gly Val Met Leu Phe Gly Leu Leu Met
305                 310                 315                 320

Thr Leu Phe Ser Ser Leu Trp Leu Ile Phe Ala Gly Met Leu Leu Phe
            325                 330                 335

Ser Ala Gly Phe Phe Ala Ala His Ser Val Ala Ser Ser Trp Ile Gly
            340                 345                 350

Pro Arg Ala Lys Arg Ala Lys Gly Gln Ala Ser Ser Leu Tyr Leu Phe
        355                 360                 365

Ser Tyr Tyr Leu Gly Ser Ser Ile Ala Gly Thr Leu Gly Gly Val Phe
    370                 375                 380

Trp His Asn Tyr Gly Trp Asn Gly Val Gly Ala Phe Ile Ala Leu Met
385                 390                 395                 400

Leu Val Ile Ala Leu Leu Val Gly Thr Arg Leu His Arg Arg Leu His
            405                 410                 415

Ala

<210> SEQ ID NO 9
<211> LENGTH: 1248
<212> TYPE: DNA
<213> ORGANISM: Pantoea ananatis

<400> SEQUENCE: 9

```
gtgaatcgct cttcacctgc ggtgccgctg acagcgaca tgcctgcgca gtctgaggct      60
tcctcgtctg actggattgt gcgcggcacc cggccttta tgcgcgtcac gctcgccttg     120
ttttctgccg ggctggccac ctttgccctg ctgtattgcg tgcagcctat tctgccggtg    180
ctctctgcac agtttggcat ttctcccgcc gcgagcagta tttcgctttc catttccacc    240
gccatgatgg ccctgggatt actggtgaca ggcccgctgt ccgatgccat aggacggaag    300
tccgtgatgg taacggcgct catgctggcc gcaatctgta ccctgctctc tgccactatg    360
accagctggc acggcatttt actgatgcgg ggcttgatcg gcttatcgct gagcggtgtg    420
gccgcggtgg gcatgaccta tctgagtgaa gagattcatc ccagtgtggt ggcttttttcg    480 atggggctgt acatcagcgg aaactcgatt ggcggcatga gcggccgcct gataagcggt    540
gtattaaccg acttcttttc atggcgcata gccattgcgg ccattggctg ttttgccctc    600
gccgctgccc tgatgttctg gagaatctta ccggaatcgc gccatttccg tccggcctcg    660
ctgcgcccgc gtcatctgac cattaacttc cgtctgcact ggcgcgatgc gggattgccg    720
```

-continued

```
ctgctgtttg ctgaaggcct gctgctgatg ggcgcctttg tgacgctgtt caactatatc    780
ggctatcgcc tgctgggcgc gccgtggcat ttaagtcagg ctgtggtggg cttgctgtcg    840
gtggtttatc tgaccgggtc atggagttcc cctaaagccg gcgcgttaac cagccggttt    900
gggcgcggcc cggttatgtt tggctcgacc tttattatgc tgatgggggtt actgctgacg   960 gcatttaacg gtatcgtgct gatcttcatt ggtatgatgc tgtttacggc aggatttttc   1020
gctgcgcact ccgtggcgag cggctggatt ggcccacgcg ctcgtcgggc aaaaggtcag   1080
gcttcttcgc tctatctgtt cagctattac gtcggctcaa gcgtggcggg tacagctggc   1140 ggcttttttct ggcatcagtt tggctggggc ggcctgacac tgtttatctc cgctttactg   1200
ctgttagcgt tgtgggttgc ctggcagctg caccgccgca aactctag                1248
```

<210> SEQ ID NO 10
<211> LENGTH: 415
<212> TYPE: PRT
<213> ORGANISM: Pantoea ananatis

<400> SEQUENCE: 10

```
Met Asn Arg Ser Ser Pro Ala Val Pro Leu Asp Ser Asp Met Pro Ala
1               5                   10                  15

Gln Ser Glu Ala Ser Ser Ser Asp Trp Ile Val Arg Gly Thr Arg Pro
            20                  25                  30

Phe Met Arg Val Thr Leu Ala Leu Phe Ser Ala Gly Leu Ala Thr Phe
        35                  40                  45

Ala Leu Leu Tyr Cys Val Gln Pro Ile Leu Pro Val Leu Ser Ala Gln
    50                  55                  60

Phe Gly Ile Ser Pro Ala Ala Ser Ser Ile Ser Leu Ser Ile Ser Thr
65                  70                  75                  80

Ala Met Met Ala Leu Gly Leu Val Thr Gly Pro Leu Ser Asp Ala
                85                  90                  95

Ile Gly Arg Lys Ser Val Met Val Thr Ala Leu Met Leu Ala Ala Ile
            100                 105                 110

Cys Thr Leu Leu Ser Ala Thr Met Thr Ser Trp His Gly Ile Leu Leu
        115                 120                 125

Met Arg Gly Leu Ile Gly Leu Ser Leu Ser Gly Val Ala Ala Val Gly
    130                 135                 140

Met Thr Tyr Leu Ser Glu Glu Ile His Pro Ser Val Val Ala Phe Ser
145                 150                 155                 160

Met Gly Leu Tyr Ile Ser Gly Asn Ser Ile Gly Gly Met Ser Gly Arg
                165                 170                 175

Leu Ile Ser Gly Val Leu Thr Asp Phe Phe Ser Trp Arg Ile Ala Ile
            180                 185                 190

Ala Ala Ile Gly Cys Phe Ala Leu Ala Ala Ala Leu Met Phe Trp Arg
        195                 200                 205

Ile Leu Pro Glu Ser Arg His Phe Arg Pro Ala Ser Leu Arg Pro Arg
    210                 215                 220

His Leu Thr Ile Asn Phe Arg Leu His Trp Arg Asp Ala Gly Leu Pro
225                 230                 235                 240

Leu Leu Phe Ala Glu Gly Leu Leu Leu Met Gly Ala Phe Val Thr Leu
                245                 250                 255

Phe Asn Tyr Ile Gly Tyr Arg Leu Leu Gly Ala Pro Trp His Leu Ser
            260                 265                 270

Gln Ala Val Val Gly Leu Leu Ser Val Val Tyr Leu Thr Gly Ser Trp
```

|  |  | 275 |  |  | 280 |  |  | 285 |  |  |  |
|---|---|---|---|---|---|---|---|---|---|---|---|

Ser Ser Pro Lys Ala Gly Ala Leu Thr Ser Arg Phe Gly Arg Gly Pro
    290                 295                 300

Val Met Phe Gly Ser Thr Phe Ile Met Leu Met Gly Leu Leu Leu Thr
305                310                 315               320

Ala Phe Asn Gly Ile Val Leu Ile Phe Ile Gly Met Met Leu Phe Thr
                325                 330               335

Ala Gly Phe Phe Ala Ala His Ser Val Ala Ser Gly Trp Ile Gly Pro
            340                 345               350

Arg Ala Arg Arg Ala Lys Gly Gln Ala Ser Ser Leu Tyr Leu Phe Ser
        355                 360               365

Tyr Tyr Val Gly Ser Ser Val Ala Gly Thr Ala Gly Gly Phe Phe Trp
    370                 375               380

His Gln Phe Gly Trp Gly Gly Leu Thr Leu Phe Ile Ser Ala Leu Leu
385                390                 395               400

Leu Leu Ala Leu Trp Val Ala Trp Gln Leu His Arg Arg Lys Leu
            405                 410               415

<210> SEQ ID NO 11
<211> LENGTH: 1251
<212> TYPE: DNA
<213> ORGANISM: Enterobacter aerogenes

<400> SEQUENCE: 11

```
gtgagtaaca caacaaccgc tgacaccgcg ccggcgagcg atgtcaggga taaggtcgct      60
tcccagccaa atcaatttat taaacgcggc accccggcgt ttatccgcgt caccctggcg     120
ctatttccg ccggactggc caccttcgcc ctgctctatt gcgtgcagcc cattctgccg     180
gtgctgtcag gcgagttcgg cgtaagcccg gccagcagca gtatttcgtt atcgatttcc     240
accgcgatgc tcgccatcgg cctgctattt accggcccgc tgtcggatgc cattggccgt     300
aaaccggtaa tggtcaccgc cttactgttg gcggcgtgtt gctcattatt atcaacgatg     360
atgaccagct ggcacggtat tctgatcatg cgcgcgttga tcggcctgtc gctcagcggc     420
gtagccgccg tagggatgac ttatctcagc gaggagatcc acccaagcgt ggtggcgttt     480
tcaatggggc tttatatcag cggtaactcg ataggcggca tgagcggccg cctgctcacc     540
ggggtcttta ccgatttctt cggctggcgc gtggcgctgg cggtgataag cgccttcgcc     600
ctcgctgcgg caatcatgtt ctggcgtatt cttcccgagt cgcgccactt ccgccctatt     660
tcgttgaaac cgaaaacgct gctgattaac ttccatctgc actggcgcga tcgcggcctg     720
ccgctgttgt tcctcgaagg cttcctgctg atgggcgcat ttgtgaccct gtttaactat     780
attggctacc gtttgatgat gtcgccatgg tcgctgaatc aggcggtggt tggcctgctg     840
tcggttgctt acctgaccgg gacctggagt tcgccaaaag ccggcgcgct gacggtgcgt     900
tatggccgcg gtccagtaat gttgttcttt attgcggtga tgctgtttgg cctgctgatg     960
acgctattct cgccgctgtg gctgattttc atcggcatgc tgctgttctc cgccggcttt    1020
tttgccgcgc actcggtcgc cagcagttgg atcggaccac gggcgcgtcg cgcgcgcggc    1080
caggcatctt cgttatacct gttcagctac tatcttggct caagtattgc ggggacgctc    1140
ggtggggtct tctggcatca ttacggctgg aatggcgtcg gcggctttat cgccctgctg    1200
ttaatggccg cgctgctgac cggcgcctgt ttgcacaacc gcctgaaata a             1251
```

<210> SEQ ID NO 12
<211> LENGTH: 416

<212> TYPE: PRT
<213> ORGANISM: Enterobacter aerogenes

<400> SEQUENCE: 12

```
Met Ser Asn Thr Thr Thr Ala Asp Thr Ala Pro Ala Ser Asp Val Arg
1               5                   10                  15

Asp Lys Val Ala Ser Gln Pro Asn Gln Phe Ile Lys Arg Gly Thr Pro
            20                  25                  30

Ala Phe Ile Arg Val Thr Leu Ala Leu Phe Ser Ala Gly Leu Ala Thr
        35                  40                  45

Phe Ala Leu Leu Tyr Cys Val Gln Pro Ile Leu Pro Val Leu Ser Gly
    50                  55                  60

Glu Phe Gly Val Ser Pro Ala Ser Ser Ser Ile Ser Leu Ser Ile Ser
65                  70                  75                  80

Thr Ala Met Leu Ala Ile Gly Leu Leu Phe Thr Gly Pro Leu Ser Asp
                85                  90                  95

Ala Ile Gly Arg Lys Pro Val Met Val Thr Ala Leu Leu Leu Ala Ala
            100                 105                 110

Cys Cys Ser Leu Leu Ser Thr Met Met Thr Ser Trp His Gly Ile Leu
        115                 120                 125

Ile Met Arg Ala Leu Ile Gly Leu Ser Leu Ser Gly Val Ala Ala Val
    130                 135                 140

Gly Met Thr Tyr Leu Ser Glu Glu Ile His Pro Ser Val Ala Phe
145                 150                 155                 160

Ser Met Gly Leu Tyr Ile Ser Gly Asn Ser Ile Gly Gly Met Ser Gly
                165                 170                 175

Arg Leu Leu Thr Gly Val Phe Thr Asp Phe Phe Gly Trp Arg Val Ala
            180                 185                 190

Leu Ala Val Ile Ser Ala Phe Ala Leu Ala Ala Ile Met Phe Trp
        195                 200                 205

Arg Ile Leu Pro Glu Ser Arg His Phe Arg Pro Ile Ser Leu Lys Pro
    210                 215                 220

Lys Thr Leu Leu Ile Asn Phe His Leu His Trp Arg Asp Arg Gly Leu
225                 230                 235                 240

Pro Leu Leu Phe Leu Glu Gly Phe Leu Leu Met Gly Ala Phe Val Thr
                245                 250                 255

Leu Phe Asn Tyr Ile Gly Tyr Arg Leu Met Met Ser Pro Trp Ser Leu
            260                 265                 270

Asn Gln Ala Val Val Gly Leu Leu Ser Val Ala Tyr Leu Thr Gly Thr
        275                 280                 285

Trp Ser Ser Pro Lys Ala Gly Ala Leu Thr Val Arg Tyr Gly Arg Gly
    290                 295                 300

Pro Val Met Leu Phe Phe Ile Ala Val Met Leu Phe Gly Leu Leu Met
305                 310                 315                 320

Thr Leu Phe Ser Pro Leu Trp Leu Ile Phe Ile Gly Met Leu Leu Phe
                325                 330                 335

Ser Ala Gly Phe Phe Ala Ala His Ser Val Ala Ser Ser Trp Ile Gly
            340                 345                 350

Pro Arg Ala Arg Arg Ala Arg Gly Gln Ala Ser Ser Leu Tyr Leu Phe
        355                 360                 365

Ser Tyr Tyr Leu Gly Ser Ser Ile Ala Gly Thr Leu Gly Gly Val Phe
    370                 375                 380

Trp His His Tyr Gly Trp Asn Gly Val Gly Gly Phe Ile Ala Leu Leu
385                 390                 395                 400
```

Leu Met Ala Ala Leu Leu Thr Gly Ala Cys Leu His Asn Arg Leu Lys
            405                 410                 415

<210> SEQ ID NO 13
<211> LENGTH: 1251
<212> TYPE: DNA
<213> ORGANISM: Corynebacterium glutamicum

<400> SEQUENCE: 13

| | |
|---|---:|
| atgatgaact ccatgagcca agcaatagat agcaaggtcg aggcacacga aggccacgaa | 60 |
| ggttacaaag gcatcgagcg aggaacacgc aattacaagc gcgctgtgtt tgcgatgctg | 120 |
| gccgccggtc ttgctgcttt caatggtctt tattgcacgc aggcattgct tcccaccatg | 180 |
| acggaagagt tgggaattac gcccactgag tccgcgctga cggtgtcggc gacaactgga | 240 |
| atgttggcgc tgtgcattgt tccggcgtcg atactttcgg agaaatttgg ccgcggtcgg | 300 |
| gtgctgacaa tttcactcac gttggccatc atcgtgggat taattttgcc gcttgtcccc | 360 |
| aatatcactg ctctcatcct gctcagaggt ctccaaggtg cgctgcttgc tggcactccg | 420 |
| gcggtggcga tgacctggtt gtctgaggaa attcacccca aggatattgg catgcgatg | 480 |
| ggaatttaca tcgcgggaaa tactgtcggc gggctcactg gacgtatgat ccggcggga | 540 |
| ctacttgaag taactcattg gcaaaacgca ctgctgggaa gttctatcgc tgcgctaatc | 600 |
| ttcggcgtaa tcatggtggt gttgcttccc aagcagcgga aattccagcc gaagaatatc | 660 |
| aatctgggcc atgaggtttc tgcgatggct gctcattggc ggaatcctcg tttggctttg | 720 |
| ctctttggta ctgcatttt gggcatgggt acttttgtgt cgctgtacaa ctatttgggt | 780 |
| ttccgcatga ttgatcagtt tgggctgagt gaagtgctgg ttggtgcagt gttcatcatg | 840 |
| tatctggccg ggacctggag ttccacccag gcgggtgcgt tgaggagaa gattggcaat | 900 |
| ggacaaactg tcattttctt gagcctgatg atgatcgcct cgatggctct catgggcatt | 960 |
| aacaatttgt ggatcaccct catcgcgctt tttgtgttca cagcagcgtt tttcgcactg | 1020 |
| cattccagtg cttcgggatg gatcggaatc atcgcaacga aggatcgcgc ggaagcctcc | 1080 |
| agcatgtatt tgttctgtta ttacgtggga tcctcggtga ttggttgggt ttctggattc | 1140 |
| gcgtttacgc atttgccgtg gttggcgttc attggctggt tgattctgct tcttttttgga | 1200 |
| gtgctggcga tttgtgtgac gctggcaagg cttgcccgca acgccaatta a | 1251 |

<210> SEQ ID NO 14
<211> LENGTH: 416
<212> TYPE: PRT
<213> ORGANISM: Corynebacterium glutamicum

<400> SEQUENCE: 14

Met Met Asn Ser Met Ser Gln Ala Ile Asp Ser Lys Val Glu Ala His
1               5                  10                  15

Glu Gly His Glu Gly Tyr Lys Gly Ile Glu Arg Gly Thr Arg Asn Tyr
            20                  25                  30

Lys Arg Ala Val Phe Ala Met Leu Ala Ala Gly Leu Ala Ala Phe Asn
        35                  40                  45

Gly Leu Tyr Cys Thr Gln Ala Leu Leu Pro Thr Met Thr Glu Glu Leu
    50                  55                  60

Gly Ile Thr Pro Thr Glu Ser Ala Leu Thr Val Ser Ala Thr Thr Gly
65                  70                  75                  80

Met Leu Ala Leu Cys Ile Val Pro Ala Ser Ile Leu Ser Glu Lys Phe
                85                  90                  95

Gly Arg Gly Arg Val Leu Thr Ile Ser Leu Thr Leu Ala Ile Ile Val
            100                 105                 110

Gly Leu Ile Leu Pro Leu Val Pro Asn Ile Thr Ala Leu Ile Leu Leu
        115                 120                 125

Arg Gly Leu Gln Gly Ala Leu Leu Ala Gly Thr Pro Ala Val Ala Met
    130                 135                 140

Thr Trp Leu Ser Glu Glu Ile His Pro Lys Asp Ile Gly His Ala Met
145                 150                 155                 160

Gly Ile Tyr Ile Ala Gly Asn Thr Val Gly Leu Thr Gly Arg Met
                165                 170                 175

Ile Pro Ala Gly Leu Leu Glu Val Thr His Trp Gln Asn Ala Leu Leu
            180                 185                 190

Gly Ser Ser Ile Ala Ala Leu Ile Phe Gly Val Ile Met Val Val Leu
        195                 200                 205

Leu Pro Lys Gln Arg Lys Phe Gln Pro Lys Asn Ile Asn Leu Gly His
    210                 215                 220

Glu Val Ser Ala Met Ala Ala His Trp Arg Asn Pro Arg Leu Ala Leu
225                 230                 235                 240

Leu Phe Gly Thr Ala Phe Leu Gly Met Gly Thr Phe Val Ser Leu Tyr
                245                 250                 255

Asn Tyr Leu Gly Phe Arg Met Ile Asp Gln Phe Gly Leu Ser Glu Val
            260                 265                 270

Leu Val Gly Ala Val Phe Ile Met Tyr Leu Ala Gly Thr Trp Ser Ser
        275                 280                 285

Thr Gln Ala Gly Ala Leu Arg Glu Lys Ile Gly Asn Gly Gln Thr Val
    290                 295                 300

Ile Phe Leu Ser Leu Met Met Ile Ala Ser Met Ala Leu Met Gly Ile
305                 310                 315                 320

Asn Asn Leu Trp Ile Thr Leu Ile Ala Leu Phe Val Phe Thr Ala Ala
                325                 330                 335

Phe Phe Ala Leu His Ser Ser Ala Ser Gly Trp Ile Gly Ile Ile Ala
            340                 345                 350

Thr Lys Asp Arg Ala Glu Ala Ser Ser Met Tyr Leu Phe Cys Tyr Tyr
        355                 360                 365

Val Gly Ser Ser Val Ile Gly Trp Val Ser Gly Phe Ala Phe Thr His
    370                 375                 380

Leu Pro Trp Leu Ala Phe Ile Gly Trp Leu Ile Leu Leu Phe Gly
385                 390                 395                 400

Val Leu Ala Ile Cys Val Thr Leu Ala Arg Leu Ala Arg Asn Ala Asn
                405                 410                 415

<210> SEQ ID NO 15
<211> LENGTH: 1251
<212> TYPE: DNA
<213> ORGANISM: Corynebacterium glutamicum

<400> SEQUENCE: 15
atgatgaact ccatgagcca agcaatagat agcaaggtcg aggcacacga aggccacgaa     60
ggttacaaag gcatcgagcg aggaacacgc aattacaagc gcgctgtgtt tgcgatgctg    120
gccgccggtc ttgctgcttt caatggtctt tattgcacgc aggcattgct tcccaccatg    180
acggaagagt gggaattac gcccactgag tccgcgctga cggtgtcggc gacaactgga    240
atgttggcgc tgtgcattgt tccggcgtcg atactttcgg agaaatttgg ccgcggtcgg    300

-continued

```
gtgctgacaa tttcactcac gttggccatc atcgtgggat taattttgcc gcttgtcccc    360
aatatcactg ctctcatcct gctcagaggt ctccaaggtg cgctgcttgc tggcactccg    420
gcggtggcga tgacctggtt gtctgaggaa attcacccca aggatattgg gcatgcgatg    480
ggaatttaca tcgcgggaaa tactgtcggc gggctcactg gacgtatgat tccggcggga    540
ctacttgaag taactcattg gcaaaacgca ctgctgggaa gttctatcgc tgcgctaatc    600
ttcggcgtaa tcatggtggt gttgcttccc aagcagcgga aattccagcc gaagaatatc    660
aatctgggcc atgaggtttc tgcgatggct gctcattggc ggaatcctcg tttggctttg    720
ctctttggta ctgcattttt gggcatgggt acttttgtgt cgctgtacaa ctatttgggt    780
ttccgcatga ttgatcagtt tgggctgagt gaagtgctgg ttggtgcagt gttcatcatg    840
tatctggccg ggacctggag ttccacccag gcgggtgcgt tgagggagaa gattggcaat    900
ggacaaactg tcattttctt gagcctgatg atgatcgcct cgatggctct catgggcatt    960
aacaatttgt ggatcaccct catcgcgctt tttgtgttca cagcagcgtt tttcgcactg   1020
cattccagtg cttcgggatg gatcggaatc atcgcaacga aggatcgcgc ggaagcctcc   1080
agcatgtatt tgttctgtta ttacgtggga tcctcggtga ttggttgggt ttctggattc   1140
gcgtttacgc atttgccgtg gttggcgttc attggctggt tgattctgct tcttttttgga   1200
gtgctggcga tttgtgtgac gctggcaagg cttgcccgca acgccaatta a            1251
```

<210> SEQ ID NO 16
<211> LENGTH: 416
<212> TYPE: PRT
<213> ORGANISM: Corynebacterium glutamicum

<400> SEQUENCE: 16

```
Met Met Asn Ser Met Ser Gln Ala Ile Asp Ser Lys Val Glu Ala His
1               5                   10                  15
Glu Gly His Glu Gly Tyr Lys Gly Ile Glu Arg Gly Thr Arg Asn Tyr
                20                  25                  30
Lys Arg Ala Val Phe Ala Met Leu Ala Ala Gly Leu Ala Ala Phe Asn
            35                  40                  45
Gly Leu Tyr Cys Thr Gln Ala Leu Leu Pro Thr Met Thr Glu Glu Leu
        50                  55                  60
Gly Ile Thr Pro Thr Glu Ser Ala Leu Thr Val Ser Ala Thr Thr Gly
65                  70                  75                  80
Met Leu Ala Leu Cys Ile Val Pro Ala Ser Ile Leu Ser Glu Lys Phe
                85                  90                  95
Gly Arg Gly Arg Val Leu Thr Ile Ser Leu Thr Leu Ala Ile Ile Val
            100                 105                 110
Gly Leu Ile Leu Pro Leu Val Pro Asn Ile Thr Ala Leu Ile Leu Leu
        115                 120                 125
Arg Gly Leu Gln Gly Ala Leu Leu Ala Gly Thr Pro Ala Val Ala Met
    130                 135                 140
Thr Trp Leu Ser Glu Glu Ile His Pro Lys Asp Ile Gly His Ala Met
145                 150                 155                 160
Gly Ile Tyr Ile Ala Gly Asn Thr Val Gly Gly Leu Thr Gly Arg Met
                165                 170                 175
Ile Pro Ala Gly Leu Leu Glu Val Thr His Trp Gln Asn Ala Leu Leu
            180                 185                 190
Gly Ser Ser Ile Ala Ala Leu Ile Phe Gly Val Ile Met Val Val Leu
        195                 200                 205
```

| Leu | Pro | Lys | Gln | Arg | Lys | Phe | Gln | Pro | Lys | Asn | Ile | Asn | Leu | Gly | His |
|---|---|---|---|---|---|---|---|---|---|---|---|---|---|---|---|
| 210 | | | | 215 | | | | | 220 | | | | | | |

| Glu | Val | Ser | Ala | Met | Ala | Ala | His | Trp | Arg | Asn | Pro | Arg | Leu | Ala | Leu |
|---|---|---|---|---|---|---|---|---|---|---|---|---|---|---|---|
| 225 | | | | 230 | | | | 235 | | | | | 240 | | |

Leu Phe Gly Thr Ala Phe Leu Gly Met Gly Thr Phe Val Ser Leu Tyr
                        245                  250                  255

Asn Tyr Leu Gly Phe Arg Met Ile Asp Gln Phe Gly Leu Ser Glu Val
                 260                  265                  270

Leu Val Gly Ala Val Phe Ile Met Tyr Leu Ala Gly Thr Trp Ser Ser
               275                  280                  285

Thr Gln Ala Gly Ala Leu Arg Glu Lys Ile Gly Asn Gly Gln Thr Val
290                        295                  300

Ile Phe Leu Ser Leu Met Met Ile Ala Ser Met Ala Leu Met Gly Ile
305                  310                  315              320

Asn Asn Leu Trp Ile Thr Leu Ile Ala Leu Phe Val Phe Thr Ala Ala
               325                  330                  335

Phe Phe Ala Leu His Ser Ser Ala Ser Gly Trp Ile Gly Ile Ile Ala
                 340                  345                  350

Thr Lys Asp Arg Ala Glu Ala Ser Ser Met Tyr Leu Phe Cys Tyr Tyr
               355                  360                  365

Val Gly Ser Ser Val Ile Gly Trp Val Ser Gly Phe Ala Phe Thr His
         370                  375                  380

Leu Pro Trp Leu Ala Phe Ile Gly Trp Leu Ile Leu Leu Leu Phe Gly
385                       390                  395              400

Val Leu Ala Ile Cys Val Thr Leu Ala Arg Leu Ala Arg Asn Ala Asn
                 405                  410                  415

<210> SEQ ID NO 17
<211> LENGTH: 771
<212> TYPE: DNA
<213> ORGANISM: Escherichia coli

<400> SEQUENCE: 17

```
atgcaaactg agcaacagcg agccgtaaca cggctttgta tccagtgtgg attatttctt      60
ttgcaacatg gtgcggaaag cgcgttggtt gatgagcttt cctcacgact gggtcgggca     120
ctgggaatgg acagcgtcga aagttctatc tcttcgaacg ccatagtgct gacaactatt     180
aaagatgggc aatgcctgac atcgacacgt aaaaatcacg atcgcggcat taatatgcat     240
gtggtgactg aagtccagca cattgtgatt cttgcggagc atcatctgct ggattacaaa     300
ggcgtagaga aacgatttag ccaaattcag ccattacgtt acccaagatg gctggtagcc     360
ttaatggttg gcctttcttg cgcctgtttc tgtaaactca ataacggtgg ctgggatggt     420
gccgtcatca cctctttgc cagtacgacc gcgatgtata tccgccagct gctggcacaa     480
cgtcatcttc atccacagat caacttttgc cttaccgctt cgccgccac caccatttcc     540
ggattgcttt tgcaactccc cactttcagc aatacccca ccattgcgat ggccgccagc     600
gttctgctgc tagtgccggg ctttccgttg attaatgccg tcgccgatat gtttaaaggc     660
cacatcaata ccggactggc acgctgggcg atcgccagtc tgctgacact ggctacctgc     720
gtcggcgtag tgatggcact gacgatttgg gggctacgcg gatgggtgtg a            771
```

<210> SEQ ID NO 18
<211> LENGTH: 256
<212> TYPE: PRT
<213> ORGANISM: Escherichia coli

```
<400> SEQUENCE: 18

Met Gln Thr Glu Gln Gln Arg Ala Val Thr Arg Leu Cys Ile Gln Cys
1               5                   10                  15

Gly Leu Phe Leu Leu Gln His Gly Ala Glu Ser Ala Leu Val Asp Glu
            20                  25                  30

Leu Ser Ser Arg Leu Gly Arg Ala Leu Gly Met Asp Ser Val Glu Ser
        35                  40                  45

Ser Ile Ser Ser Asn Ala Ile Val Leu Thr Thr Ile Lys Asp Gly Gln
    50                  55                  60

Cys Leu Thr Ser Thr Arg Lys Asn His Asp Arg Gly Ile Asn Met His
65                  70                  75                  80

Val Val Thr Glu Val Gln His Ile Val Ile Leu Ala Glu His His Leu
                85                  90                  95

Leu Asp Tyr Lys Gly Val Glu Lys Arg Phe Ser Gln Ile Gln Pro Leu
            100                 105                 110

Arg Tyr Pro Arg Trp Leu Val Ala Leu Met Val Gly Leu Ser Cys Ala
        115                 120                 125

Cys Phe Cys Lys Leu Asn Asn Gly Gly Trp Asp Gly Ala Val Ile Thr
    130                 135                 140

Phe Phe Ala Ser Thr Thr Ala Met Tyr Ile Arg Gln Leu Leu Ala Gln
145                 150                 155                 160

Arg His Leu His Pro Gln Ile Asn Phe Cys Leu Thr Ala Phe Ala Ala
                165                 170                 175

Thr Thr Ile Ser Gly Leu Leu Leu Gln Leu Pro Thr Phe Ser Asn Thr
            180                 185                 190

Pro Thr Ile Ala Met Ala Ala Ser Val Leu Leu Val Pro Gly Phe
        195                 200                 205

Pro Leu Ile Asn Ala Val Ala Asp Met Phe Lys Gly His Ile Asn Thr
    210                 215                 220

Gly Leu Ala Arg Trp Ala Ile Ala Ser Leu Leu Thr Leu Ala Thr Cys
225                 230                 235                 240

Val Gly Val Val Met Ala Leu Thr Ile Trp Gly Leu Arg Gly Trp Val
                245                 250                 255

<210> SEQ ID NO 19
<211> LENGTH: 777
<212> TYPE: DNA
<213> ORGANISM: Enterobacter aerogenes

<400> SEQUENCE: 19
atgcaggcag ataaatcaga gcagcgcgcc gtcacccggt tgtgcatcca gtgtgccctt      60
tacttactcc agcacggtgc ggaaagcgcg ctggttgagg agctttctac ccgcctcggg     120
cgggcgttag gtatggatag cgttgaaagc gctatctcct ctaatgcgat cgtgctcacc     180
acgattaaag acggcgaatg tctcacctcc acgcgtaaaa acagcgatcg cggaattaac     240
atgcatgtgg tgacggaggt acagcatatt gtgatcatgg ccgaacataa gctgttggat     300
tacaaagacg tcgagaagcg cttctcgcag atcaaaccct acgctacccg cgctggcta      360 ctggtattaa tggtcggcct ctcctgcgcc tgcttttgta aattgaacaa cggcggttgg     420
gatggcgcgg tggttaccct cttcgccagt accgtcgcca tgtatattcg ccaactgcta     480
acccaccgtt ccatgcatcc gcagattaat ttctgcatta ctgcctttgt cgccaccacc     540
atttccgggc tgatgctgcg tctgccggca tttagcgaga cgccgactat cgccatggcc     600
gccagcgtgc tgttgctggt tcccggcttt ccgttaatta acgccgtggc cgatatgttc     660
```

```
aagggccata tcaataccgg gctggcccgc tgggcgatcg ccagcctgct gacgctggcg    720
acctgtatcg gggtggtaat ggcaatgacc atgtgggggc tacgcggatg ggcataa      777
```

<210> SEQ ID NO 20
<211> LENGTH: 258
<212> TYPE: PRT
<213> ORGANISM: Enterobacter aerogenes

<400> SEQUENCE: 20

```
Met Gln Ala Asp Lys Ser Glu Gln Arg Ala Val Thr Arg Leu Cys Ile
1               5                   10                  15
Gln Cys Ala Leu Tyr Leu Leu Gln His Gly Ala Glu Ser Ala Leu Val
            20                  25                  30
Glu Glu Leu Ser Thr Arg Leu Gly Arg Ala Leu Gly Met Asp Ser Val
        35                  40                  45
Glu Ser Ala Ile Ser Ser Asn Ala Ile Val Leu Thr Thr Ile Lys Asp
    50                  55                  60
Gly Glu Cys Leu Thr Ser Thr Arg Lys Asn Ser Asp Arg Gly Ile Asn
65                  70                  75                  80
Met His Val Val Thr Glu Val Gln His Ile Val Ile Met Ala Glu His
                85                  90                  95
Lys Leu Leu Asp Tyr Lys Asp Val Glu Lys Arg Phe Ser Gln Ile Lys
            100                 105                 110
Pro Leu Arg Tyr Pro Arg Trp Leu Leu Val Leu Met Val Gly Leu Ser
        115                 120                 125
Cys Ala Cys Phe Cys Lys Leu Asn Asn Gly Gly Trp Asp Gly Ala Val
    130                 135                 140
Val Thr Phe Phe Ala Ser Thr Val Ala Met Tyr Ile Arg Gln Leu Leu
145                 150                 155                 160
Thr His Arg Ser Met His Pro Gln Ile Asn Phe Cys Ile Thr Ala Phe
                165                 170                 175
Val Ala Thr Thr Ile Ser Gly Leu Met Leu Arg Leu Pro Ala Phe Ser
            180                 185                 190
Glu Thr Pro Thr Ile Ala Met Ala Ala Ser Val Leu Leu Val Pro
        195                 200                 205
Gly Phe Pro Leu Ile Asn Ala Val Ala Asp Met Phe Lys Gly His Ile
    210                 215                 220
Asn Thr Gly Leu Ala Arg Trp Ala Ile Ala Ser Leu Leu Thr Leu Ala
225                 230                 235                 240
Thr Cys Ile Gly Val Val Met Ala Met Thr Met Trp Gly Leu Arg Gly
                245                 250                 255
Trp Ala
```

<210> SEQ ID NO 21
<211> LENGTH: 474
<212> TYPE: DNA
<213> ORGANISM: Escherichia coli

<400> SEQUENCE: 21

```
atgggtgtga tcgaatttct gttagcgttg gcgcaggata tgatcctcgc cgccattcct    60
gcggtcggct ttgcgatggt gttcaacgtt cccgtgcggg cgttacgctg gtgtgcgctg   120
cttggctcga taggtcatgg ttcccgaatg atcttgatga ccagcgggtt gaatattgag   180
tggtcaacct ttatggcttc tatgctggtc ggtaccattg gtattcaatg gtcgcgctgg   240
```

```
tatctggcgc atccgaaagt gtttaccgtg gcggccgtta tccctatgtt cccgggcata    300
tcggcttata ccgcaatgat ttcggcggta aaaatcagcc agttaggtta cagcgaaccg    360
ttgatgatta ccctgttaac caactttctt acagcttcat cgattgttgg tgcgttatcc    420
atcggtcttt ccattcctgg attatggttg taccgcaagc gccctcgcgt ataa          474
```

<210> SEQ ID NO 22
<211> LENGTH: 157
<212> TYPE: PRT
<213> ORGANISM: Escherichia coli

<400> SEQUENCE: 22

```
Met Gly Val Ile Glu Phe Leu Leu Ala Leu Ala Gln Asp Met Ile Leu
1               5                   10                  15

Ala Ala Ile Pro Ala Val Gly Phe Ala Met Val Phe Asn Val Pro Val
            20                  25                  30

Arg Ala Leu Arg Trp Cys Ala Leu Leu Gly Ser Ile Gly His Gly Ser
        35                  40                  45

Arg Met Ile Leu Met Thr Ser Gly Leu Asn Ile Glu Trp Ser Thr Phe
    50                  55                  60

Met Ala Ser Met Leu Val Gly Thr Ile Gly Ile Gln Trp Ser Arg Trp
65                  70                  75                  80

Tyr Leu Ala His Pro Lys Val Phe Thr Val Ala Ala Val Ile Pro Met
                85                  90                  95

Phe Pro Gly Ile Ser Ala Tyr Thr Ala Met Ile Ser Ala Val Lys Ile
            100                 105                 110

Ser Gln Leu Gly Tyr Ser Glu Pro Leu Met Ile Thr Leu Leu Thr Asn
        115                 120                 125

Phe Leu Thr Ala Ser Ser Ile Val Gly Ala Leu Ser Ile Gly Leu Ser
    130                 135                 140

Ile Pro Gly Leu Trp Leu Tyr Arg Lys Arg Pro Arg Val
145                 150                 155
```

<210> SEQ ID NO 23
<211> LENGTH: 474
<212> TYPE: DNA
<213> ORGANISM: Enterobacter aerogenes

<400> SEQUENCE: 23

```
atgggcataa tctcttatct tttcgacctg gcgcaggata tggcgctggc ggccatccct     60
gctgtcggct ttgcgatggt gttcaacgtc ccacagcgcg cgctgcgctg gtgcgcgtta    120
ctgggcgcta tcggccacgg ctcgcggatg gtgatgatga gcgcaggctt caatatagaa    180
tgggccacct ttctcgccgc gttactggtc ggtagtatag gcattcagtg gtcgcgctgg    240
tatctggcgc acccgaagat atttaccgtc gccgcggtga tcccgatgtt ccctgggatt    300
tcggcttata cggcgatgat ctcggccgtc aaaatcagcc attttggtta ctccgaagag    360
atgatgatta tgctgttgag caactttta aaagcctcct ccatcgtcgg ggcgctctct    420
atcgggctgt ctattcccgg tctgtggctc tatcgcaaac gcccgcgcgt gtaa          474
```

<210> SEQ ID NO 24
<211> LENGTH: 157
<212> TYPE: PRT
<213> ORGANISM: Enterobacter aerogenes

<400> SEQUENCE: 24

```
Met Gly Ile Ile Ser Tyr Leu Phe Asp Leu Ala Gln Asp Met Ala Leu
```

```
1               5                   10                  15
Ala Ala Ile Pro Ala Val Gly Phe Ala Met Val Phe Asn Val Pro Gln
                20                  25                  30
Arg Ala Leu Arg Trp Cys Ala Leu Leu Gly Ala Ile Gly His Gly Ser
                35                  40                  45
Arg Met Val Met Met Ser Ala Gly Phe Asn Ile Glu Trp Ala Thr Phe
 50                  55                  60
Leu Ala Ala Leu Leu Val Gly Ser Ile Gly Ile Gln Trp Ser Arg Trp
 65                  70                  75                  80
Tyr Leu Ala His Pro Lys Ile Phe Thr Val Ala Ala Val Ile Pro Met
                85                  90                  95
Phe Pro Gly Ile Ser Ala Tyr Thr Ala Met Ile Ser Ala Val Lys Ile
                100                 105                 110
Ser His Phe Gly Tyr Ser Glu Glu Met Met Ile Met Leu Leu Ser Asn
                115                 120                 125
Phe Leu Lys Ala Ser Ser Ile Val Gly Ala Leu Ser Ile Gly Leu Ser
                130                 135                 140
Ile Pro Gly Leu Trp Leu Tyr Arg Lys Arg Pro Arg Val
145                 150                 155
```

<210> SEQ ID NO 25
<211> LENGTH: 29
<212> TYPE: DNA
<213> ORGANISM: Artificial Sequence
<220> FEATURE:
<223> OTHER INFORMATION: primer

<400> SEQUENCE: 25
tcactcatta ggcaccccag gctttacac                                29

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
tgtcctactc aggagagcgt tcaccgacaa                               30

<210> SEQ ID NO 27
<211> LENGTH: 80
<212> TYPE: DNA
<213> ORGANISM: Artificial Sequence
<220> FEATURE:
<223> OTHER INFORMATION: primer

<400> SEQUENCE: 27
gcatatgtat gacaccgtca aggttccga ctacatcggt gaccaggacg tgaagcctgc   60 tttttttatac taagttggca                                            80

<210> SEQ ID NO 28
<211> LENGTH: 80
<212> TYPE: DNA
<213> ORGANISM: Artificial Sequence
<220> FEATURE:
<223> OTHER INFORMATION: primer

<400> SEQUENCE: 28
tccagctcaa ggcactcaat acgctgtgta ttgaagtcag gtgagcggtc cgctcaagtt  60
agtataaaaa agctgaacga						80

<210> SEQ ID NO 29
<211> LENGTH: 40
<212> TYPE: DNA
<213> ORGANISM: Artificial Sequence
<220> FEATURE:
<223> OTHER INFORMATION: primer

<400> SEQUENCE: 29
gatcaagctt tttacccgcg gacagctatc ttgcgctctg						40

<210> SEQ ID NO 30
<211> LENGTH: 43
<212> TYPE: DNA
<213> ORGANISM: Artificial Sequence
<220> FEATURE:
<223> OTHER INFORMATION: primer

<400> SEQUENCE: 30
gatcggtacc accaccgggt ttcgcattaa gtcattgtct gag						43

<210> SEQ ID NO 31
<211> LENGTH: 39
<212> TYPE: DNA
<213> ORGANISM: Artificial Sequence
<220> FEATURE:
<223> OTHER INFORMATION: primer

<400> SEQUENCE: 31
gatcgaattc ataaggatcc cctgtgaatc gctcttcac						39

<210> SEQ ID NO 32
<211> LENGTH: 40
<212> TYPE: DNA
<213> ORGANISM: Artificial Sequence
<220> FEATURE:
<223> OTHER INFORMATION: primer

<400> SEQUENCE: 32
gatcctgcag cggggaaacg cgtgctttag gcaatcatac						40

<210> SEQ ID NO 33
<211> LENGTH: 80
<212> TYPE: DNA
<213> ORGANISM: Artificial Sequence
<220> FEATURE:
<223> OTHER INFORMATION: primer

<400> SEQUENCE: 33
aggcgctagc acttctactc aaaacccagc ttcccgcagg ttcagaactt tgaagcctgc						60 tttttttatac taagttggca						80

<210> SEQ ID NO 34
<211> LENGTH: 80
<212> TYPE: DNA
<213> ORGANISM: Artificial Sequence
<220> FEATURE:
<223> OTHER INFORMATION: primer

<400> SEQUENCE: 34
tcgccctgcg cgatatcttt tttcagtgtt tccagcatgc catccagcgc cgctcaagtt						60 agtataaaaa agctgaacga						80

<210> SEQ ID NO 35
<211> LENGTH: 80
<212> TYPE: DNA
<213> ORGANISM: Artificial Sequence
<220> FEATURE:
<223> OTHER INFORMATION: primer

<400> SEQUENCE: 35
cagctgtaaa tcttgcgctc atgatgagtg ttagcggaaa ggacaccacc tgaagcctgc     60 tttttttatac taagttggca                                                80

<210> SEQ ID NO 36
<211> LENGTH: 80
<212> TYPE: DNA
<213> ORGANISM: Artificial Sequence
<220> FEATURE:
<223> OTHER INFORMATION: primer

<400> SEQUENCE: 36
ttgcctatga cataggcggt ttcacggcct tcatcgttgg cagccactgg cgctcaagtt     60
agtataaaaa agctgaacga                                                 80

<210> SEQ ID NO 37
<211> LENGTH: 80
<212> TYPE: DNA
<213> ORGANISM: Artificial Sequence
<220> FEATURE:
<223> OTHER INFORMATION: primer

<400> SEQUENCE: 37
agtaaataac cccactttcc ggtcaggcgc cgccatttcc gtttattcgt tgaagcctgc     60 tttttttatac taagttggca                                                80

<210> SEQ ID NO 38
<211> LENGTH: 80
<212> TYPE: DNA
<213> ORGANISM: Artificial Sequence
<220> FEATURE:
<223> OTHER INFORMATION: primer

<400> SEQUENCE: 38
gttgagaacg ttgcgaaagg tccaaacagc acgacacgct taccatcaag cgctcaagtt     60
agtataaaaa agctgaacga                                                 80

<210> SEQ ID NO 39
<211> LENGTH: 80
<212> TYPE: DNA
<213> ORGANISM: Artificial Sequence
<220> FEATURE:
<223> OTHER INFORMATION: primer

<400> SEQUENCE: 39
ttgcaaccgg agcatgactg catggaactc gaatacgaaa gtaaacgccc tgaagcctgc     60 tttttttatac taagttggca                                                80

<210> SEQ ID NO 40
<211> LENGTH: 80
<212> TYPE: DNA
<213> ORGANISM: Artificial Sequence
<220> FEATURE:
<223> OTHER INFORMATION: primer

<400> SEQUENCE: 40

```
gtgtctttag atagaggtac ggcggtagtg gcggtattga ggcagccaga cgctcaagtt    60
agtataaaaa agctgaacga                                                80
```

<210> SEQ ID NO 41
<211> LENGTH: 80
<212> TYPE: DNA
<213> ORGANISM: Artificial Sequence
<220> FEATURE:
<223> OTHER INFORMATION: primer

<400> SEQUENCE: 41

```
atggatgacc aactgaagca aagtgcgctc gattttcacc agtatcccac tgaagcctgc    60
ttttttatac taagttggca                                                80
```

<210> SEQ ID NO 42
<211> LENGTH: 80
<212> TYPE: DNA
<213> ORGANISM: Artificial Sequence
<220> FEATURE:
<223> OTHER INFORMATION: primer

<400> SEQUENCE: 42

```
ttacagcggc tgggtttgtg cttctaccac cgccagcgcc accatattaa cgctcaagtt    60
agtataaaaa agctgaacga                                                80
```

<210> SEQ ID NO 43
<211> LENGTH: 80
<212> TYPE: DNA
<213> ORGANISM: Artificial Sequence
<220> FEATURE:
<223> OTHER INFORMATION: primer

<400> SEQUENCE: 43

```
atggaaagca aagtagttgt tccggcggaa ggtcagaaaa tcaccctgaa tgaagcctgc    60
ttttttatac taagttggca                                                80
```

<210> SEQ ID NO 44
<211> LENGTH: 80
<212> TYPE: DNA
<213> ORGANISM: Artificial Sequence
<220> FEATURE:
<223> OTHER INFORMATION: primer

<400> SEQUENCE: 44

```
cgataatcgc gtcaccaaac tctgagcatt tcagcagttt agcgccatcc cgctcaagtt    60
agtataaaaa agctgaacga                                                80
```

<210> SEQ ID NO 45
<211> LENGTH: 80
<212> TYPE: DNA
<213> ORGANISM: Artificial Sequence
<220> FEATURE:
<223> OTHER INFORMATION: primer

<400> SEQUENCE: 45

```
gcatatgtat gacaccgtca aaggttccga ctacatcggt gaccaggacg tgaagcctgc    60
ttttttatac taagttggca                                                80
```

<210> SEQ ID NO 46
<211> LENGTH: 80
<212> TYPE: DNA
<213> ORGANISM: Artificial Sequence

```
<220> FEATURE:
<223> OTHER INFORMATION: primer

<400> SEQUENCE: 46
tccagctcaa ggcactcaat acgctgtgta ttgaagtcag gtgagcggtc cgctcaagtt     60
agtataaaaa agctgaacga                                                  80

<210> SEQ ID NO 47
<211> LENGTH: 80
<212> TYPE: DNA
<213> ORGANISM: Artificial Sequence
<220> FEATURE:
<223> OTHER INFORMATION: primer

<400> SEQUENCE: 47 aacccttttag cgatgcggaa aagcagttgc ttactcccga cgccatcgct tgaagcctgc    60 tttttttatac taagttggca                                                 80

<210> SEQ ID NO 48
<211> LENGTH: 80
<212> TYPE: DNA
<213> ORGANISM: Artificial Sequence
<220> FEATURE:
<223> OTHER INFORMATION: primer

<400> SEQUENCE: 48
atctgtttga ttcatggccg ctggcaaaaa cggacggctg aatgcctgca cgctcaagtt     60
agtataaaaa agctgaacga                                                  80

<210> SEQ ID NO 49
<211> LENGTH: 1569
<212> TYPE: DNA
<213> ORGANISM: Artificial Sequence
<220> FEATURE:
<223> OTHER INFORMATION: CAD gene optimized for expression in E. coli

<400> SEQUENCE: 49
aagcttagat ctccctgttg acaattaatc atcggctcgt ataatgtgtg gaatcgtgag     60
cggataacaa tttcacacaa ggagactgcc atgaccaaac agagcgcgga tagcaacgcg    120
aaaagcggcg tgaccagcga aatttgccat tgggcgagca acctggcgac cgatgatatt    180
ccgagcgatg tgctggaacg cgcgaaatat ctgattctgg atggcattgc gtgcgcgtgg    240
gtgggcgcgc gcgtgccgtg gagcgaaaaa tatgtgcagg cgaccatgag ctttgaaccg    300
ccgggcgcgt gccgcgtgat tggctatggc cagaaactgg gcccggtggc ggcggcgatg    360
accaacagcg cgtttattca ggcgaccgaa ctggatgatt atcatagcga agcgccgctg    420
catagcgcga gcattgtgct gccggcgtg tttgcggcga gcgaagtgct ggcggaacag    480
ggcaaaacca ttagcggcat tgatgtgatt ctggcggcga ttgtgggctt tgaaagcggc    540
ccgcgcattg gcaaagcgat ttatggcagc gatctgctga caacggctg gcattgcggc    600 gcggtgtatg gcgcgccggc gggcgcgctg gcgaccggca aactgctggg cctgaccccg    660
gatagcatgg aagatgcgct gggcattgcg tgcacccagg cgtgcggcct gatgagcgcg    720
cagtatggcg gcatggtgaa acgcgtgcag catggctttg cggcgcgcaa cggcctgctg    780
ggcggcctgc tggcgcatgg cggctatgaa gcgatgaaag cgtgctggga acgcagctat    840
ggcggctttc tgaaaatgtt taccaaaggc aacggccgcg aaccgccgta taaagaagaa    900
gaagtggtgg cgggcctggg cagcttttgg catacccttta ccattcgcat taaactgtat    960
```

```
gcgtgctgcg gcctggtgca tggcccggtg gaagcgattg aaaacctgca gggccgctat    1020
ccggaactgc tgaaccgcgc gaacctgagc aacattcgcc atgtgcatgt gcagctgagc    1080
accgcgagca acagccattg cggctggatt ccggaagaac gcccgattag cagcattgcg    1140
ggccagatga gcgtggcgta tattctggcg gtgcagctgg tggatcagca gtgcctgctg    1200
agccagttta gcgaatttga tgataacctg gaacgcccgg aagtgtggga tctggcgcgc    1260
aaagtgacca gcagccagag cgaagaattt gatcaggatg gcaactgcct gagcgcgggc    1320
cgcgtgcgca ttgaatttaa cgatggcagc agcattaccg aaagcgtgga aaaaccgctg    1380
ggcgtgaaag aaccgatgcc gaacgaacgc attctgcata aatatcgcac cctggcgggc    1440
agcgtgaccg atgaaagccg cgtgaaagaa attgaagatc tggtgctggg cctggatcgc    1500
ctgaccgata ttagcccgct gctggaactg ctgaactgcc cggtgaaaag cccgctggtg    1560
taaggtacc                                                             1569

<210> SEQ ID NO 50
<211> LENGTH: 1617
<212> TYPE: DNA
<213> ORGANISM: Actinobacillus succinogenes

<400> SEQUENCE: 50
atgactgact taaacaaact cgttaaagaa cttaatgact tagggcttac cgatgttaag      60
gaaattgtgt ataacccgag ttatgaacaa cttttcgagg aagaaaccaa accgggtttg     120
gagggtttcg ataaagggac gttaaccacg cttggcgcgg ttgccgtcga tacggggatt     180
tttaccggtc gttcaccgaa agataaatat atcgtttgcg atgaaactac gaaagacacc     240
gtttggtgga cagcgaagc ggcgaaaaac gataacaaac cgatgacgca agaaacttgg      300
aaaagtttga gagaattagt ggcgaaacaa cttttccggta acgtttatt cgtggtagaa     360 ggttactgcg gcgccagtga aaaacaccgt atcggtgtgc gtatggttac tgaagtggca    420
tggcaggcgc atttttgtga aaaacatgttt atccgaccga ccgatgaaga gttgaaaaat    480
ttcaaagcgg attttaccgt gttaaacggt gctaaatgta ctaatccgaa ctggaaagaa    540
caaggtttga cagtgaaaaa cttttgtcgct ttcaatatta ccgaaggtat tcagcttatc    600
ggcggtactt ggtacggcgg tgaaatgaaa aaaggtatgt tctcaatgat gaactacttc    660
ctgccgttaa aaggtgtggc ttccatgcac tgttccgcca acgtaggtaa agacggtgac    720
gtggctattt tcttcggttt atccggtacg ggtaaaacaa cgctttcgac cgatcctaaa    780
cgccaattaa tcggtgatga cgaacacggt tgggatgaat ccggcgtatt taactttgaa    840
ggcggttgtt acgcgaaaac cattaactta tctcaagaaa acgaaccgga tatttacggc    900
gcaatccgtc gtgacgcatt attagaaaac gtcgtggttc gtgcagacgg ttccgttgac    960
tttgacgacg gttcaaaaac agaaaatacc cgtgtttcat atccgattta ccacatcgac   1020
aacatcgttc gtccggtatc gaaagccggt catgcaacca aagtgatttt cttaaccgcg   1080
gacgcattcg gcgtattgcc gccggtttca aaactgactc cggaacaaac cgaatactac   1140
ttcttatccg gctttactgc aaaattagcg ggtacggaac gcggcgtaac cgaaccgact   1200
ccgacattct cggcctgttt cggtgcggca ttccttaagcc tgcatccgat tcaatatgcg   1260
gacgtgttgg tcgaacgcat gaaagcctcc ggtgcggaag cttatttggt gaacaccggt   1320
tggaacggca cgggtaaacg tatttcaatc aaagatacccg cggtattat cgatgcgatt   1380 ttggacggtt caatcgaaaa agcggaaatg ggcgaattgc caatctttaa tttagcgatt   1440
cctaaagcat taccgggtgt tgatcctgct attttggatc cgcgcgatac ttacgcagac   1500
```

-continued

```
aaagcgcaat ggcaagttaa agcggaagat ttggcaaacc gtttcgtgaa aaactttgtg    1560
aaatatacgg cgaatccgga agcggctaaa ttagttggcg ccggtccaaa agcataa       1617
```

<210> SEQ ID NO 51
<211> LENGTH: 538
<212> TYPE: PRT
<213> ORGANISM: Actinobacillus succinogenes

<400> SEQUENCE: 51

```
Met Thr Asp Leu Asn Lys Leu Val Lys Glu Leu Asn Asp Leu Gly Leu
1               5                  10                  15

Thr Asp Val Lys Glu Ile Val Tyr Asn Pro Ser Tyr Glu Gln Leu Phe
            20                  25                  30

Glu Glu Glu Thr Lys Pro Gly Leu Glu Gly Phe Asp Lys Gly Thr Leu
        35                  40                  45

Thr Thr Leu Gly Ala Val Ala Val Asp Thr Gly Ile Phe Thr Gly Arg
    50                  55                  60

Ser Pro Lys Asp Lys Tyr Ile Val Cys Asp Glu Thr Thr Lys Asp Thr
65                  70                  75                  80

Val Trp Trp Asn Ser Glu Ala Ala Lys Asn Asp Asn Lys Pro Met Thr
                85                  90                  95

Gln Glu Thr Trp Lys Ser Leu Arg Glu Leu Val Ala Lys Gln Leu Ser
            100                 105                 110

Gly Lys Arg Leu Phe Val Val Glu Gly Tyr Cys Gly Ala Ser Glu Lys
        115                 120                 125

His Arg Ile Gly Val Arg Met Val Thr Glu Val Ala Trp Gln Ala His
    130                 135                 140

Phe Val Lys Asn Met Phe Ile Arg Pro Thr Asp Glu Glu Leu Lys Asn
145                 150                 155                 160

Phe Lys Ala Asp Phe Thr Val Leu Asn Gly Ala Lys Cys Thr Asn Pro
                165                 170                 175

Asn Trp Lys Glu Gln Gly Leu Asn Ser Glu Asn Phe Val Ala Phe Asn
            180                 185                 190

Ile Thr Glu Gly Ile Gln Leu Ile Gly Gly Thr Trp Tyr Gly Gly Glu
        195                 200                 205

Met Lys Lys Gly Met Phe Ser Met Met Asn Tyr Phe Leu Pro Leu Lys
    210                 215                 220

Gly Val Ala Ser Met His Cys Ser Ala Asn Val Gly Lys Asp Gly Asp
225                 230                 235                 240

Val Ala Ile Phe Phe Gly Leu Ser Gly Thr Gly Lys Thr Thr Leu Ser
                245                 250                 255

Thr Asp Pro Lys Arg Gln Leu Ile Gly Asp Asp Glu His Gly Trp Asp
            260                 265                 270

Glu Ser Gly Val Phe Asn Phe Glu Gly Gly Cys Tyr Ala Lys Thr Ile
        275                 280                 285

Asn Leu Ser Gln Glu Asn Glu Pro Asp Ile Tyr Gly Ala Ile Arg Arg
    290                 295                 300

Asp Ala Leu Leu Glu Asn Val Val Val Arg Ala Asp Gly Ser Val Asp
305                 310                 315                 320

Phe Asp Asp Gly Ser Lys Thr Glu Asn Thr Arg Val Ser Tyr Pro Ile
                325                 330                 335

Tyr His Ile Asp Asn Ile Val Arg Pro Val Ser Lys Ala Gly His Ala
            340                 345                 350
```

```
Thr Lys Val Ile Phe Leu Thr Ala Asp Ala Phe Gly Val Leu Pro Pro
            355                 360                 365

Val Ser Lys Leu Thr Pro Glu Gln Thr Glu Tyr Tyr Phe Leu Ser Gly
    370                 375                 380

Phe Thr Ala Lys Leu Ala Gly Thr Glu Arg Gly Val Thr Glu Pro Thr
385                 390                 395                 400

Pro Thr Phe Ser Ala Cys Phe Gly Ala Ala Phe Leu Ser Leu His Pro
                405                 410                 415

Ile Gln Tyr Ala Asp Val Leu Val Glu Arg Met Lys Ala Ser Gly Ala
            420                 425                 430

Glu Ala Tyr Leu Val Asn Thr Gly Trp Asn Gly Thr Gly Lys Arg Ile
        435                 440                 445

Ser Ile Lys Asp Thr Arg Gly Ile Ile Asp Ala Ile Leu Asp Gly Ser
    450                 455                 460

Ile Glu Lys Ala Glu Met Gly Glu Leu Pro Ile Phe Asn Leu Ala Ile
465                 470                 475                 480

Pro Lys Ala Leu Pro Gly Val Asp Pro Ala Ile Leu Asp Pro Arg Asp
                485                 490                 495

Thr Tyr Ala Asp Lys Ala Gln Trp Gln Val Lys Ala Glu Asp Leu Ala
            500                 505                 510

Asn Arg Phe Val Lys Asn Phe Val Lys Tyr Thr Ala Asn Pro Glu Ala
        515                 520                 525

Ala Lys Leu Val Gly Ala Gly Pro Lys Ala
    530                 535

<210> SEQ ID NO 52
<211> LENGTH: 52
<212> TYPE: DNA
<213> ORGANISM: Artificial Sequence
<220> FEATURE:
<223> OTHER INFORMATION: primer

<400> SEQUENCE: 52
cggataacaa tttcacacaa ggagactgcc atgactgact taaacaaact cg              52

<210> SEQ ID NO 53
<211> LENGTH: 91
<212> TYPE: DNA
<213> ORGANISM: Artificial Sequence
<220> FEATURE:
<223> OTHER INFORMATION: primer

<400> SEQUENCE: 53
tatcactgcg aagatctatc acggcatatc cttgttctga ttcagggtga tagcattgtt      60
atctcagcct tattttcag attttattcg g                                      91

<210> SEQ ID NO 54
<211> LENGTH: 89
<212> TYPE: DNA
<213> ORGANISM: Artificial Sequence
<220> FEATURE:
<223> OTHER INFORMATION: primer

<400> SEQUENCE: 54
acgtaacctg tagtttcatc taagcttgat agcgttatca caaaaggag atggaaaacc       60 tgaagcctgc ttttttatac taagttggc                                        89

<210> SEQ ID NO 55
<211> LENGTH: 52
```

```
<212> TYPE: DNA
<213> ORGANISM: Artificial Sequence
<220> FEATURE:
<223> OTHER INFORMATION: primer

<400> SEQUENCE: 55
cgagtttgtt taagtcagtc atggcagtct ccttgtgtga aattgttatc cg      52

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
gtcgattagc ttatgtagac cg                                      22

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
tggagttcat tgacggttgg g                                       21

<210> SEQ ID NO 58
<211> LENGTH: 80
<212> TYPE: DNA
<213> ORGANISM: Artificial Sequence
<220> FEATURE:
<223> OTHER INFORMATION: primer

<400> SEQUENCE: 58
gatccgtctg tatcgtcatt accgaattgt gcacggtatc cgcatcgcgc tgaagcctgc      60 tttttttatac taagttggca                                                80

<210> SEQ ID NO 59
<211> LENGTH: 80
<212> TYPE: DNA
<213> ORGANISM: Artificial Sequence
<220> FEATURE:
<223> OTHER INFORMATION: primer

<400> SEQUENCE: 59
gccagctcaa tggtcagcca aacatagccg tgaatcggcg tttccgacag cgctcaagtt      60
agtataaaaa agctgaacga                                                 80

<210> SEQ ID NO 60
<211> LENGTH: 80
<212> TYPE: DNA
<213> ORGANISM: Artificial Sequence
<220> FEATURE:
<223> OTHER INFORMATION: primer

<400> SEQUENCE: 60
taaggtcgct tcccagccaa atcaatttat taaacgcggc accccggcgt tgaagcctgc      60 tttttttatac taagttggca                                                80

<210> SEQ ID NO 61
<211> LENGTH: 80
<212> TYPE: DNA
```

<213> ORGANISM: Artificial Sequence
<220> FEATURE:
<223> OTHER INFORMATION: primer

<400> SEQUENCE: 61
acttgagcca agatagtagc tgaacaggta taacgaagat gcctggccgc cgctcaagtt    60
agtataaaaa agctgaacga                                                80

<210> SEQ ID NO 62
<211> LENGTH: 80
<212> TYPE: DNA
<213> ORGANISM: Artificial Sequence
<220> FEATURE:
<223> OTHER INFORMATION: primer

<400> SEQUENCE: 62
ggacagacct gtgcgctgct ctctaaagtt ttccctaccc gttcccatac tgaagcctgc    60 tttttttatac taagttggca                                               80

<210> SEQ ID NO 63
<211> LENGTH: 80
<212> TYPE: DNA
<213> ORGANISM: Artificial Sequence
<220> FEATURE:
<223> OTHER INFORMATION: primer

<400> SEQUENCE: 63
actctggcag atacagggaa tggcacagcc agttttcatc atcacgttcc cgctcaagtt    60
agtataaaaa agctgaacga                                                80

<210> SEQ ID NO 64
<211> LENGTH: 36
<212> TYPE: DNA
<213> ORGANISM: Artificial Sequence
<220> FEATURE:
<223> OTHER INFORMATION: primer

<400> SEQUENCE: 64
ggccagtgcc aagctcgcgc caataatggc aacctg                              36

<210> SEQ ID NO 65
<211> LENGTH: 35
<212> TYPE: DNA
<213> ORGANISM: Artificial Sequence
<220> FEATURE:
<223> OTHER INFORMATION: primer

<400> SEQUENCE: 65
cggtacccgg ggatcaattc gtgaagacat aacgc                               35

<210> SEQ ID NO 66
<211> LENGTH: 35
<212> TYPE: DNA
<213> ORGANISM: Artificial Sequence
<220> FEATURE:
<223> OTHER INFORMATION: primer

<400> SEQUENCE: 66
cggtacccgg ggatctggga cgttgaacac catcg                               35

<210> SEQ ID NO 67
<211> LENGTH: 80
<212> TYPE: DNA
<213> ORGANISM: Artificial Sequence -continued
<220> FEATURE:
<223> OTHER INFORMATION: Ptac1000 promoter

<400> SEQUENCE: 67
ctccccatcc ccctgttggc aattaatcat cggctcgtat aatgtgtgga attgtgagcg    60
gataacaatt tcacacagga                                               80

<210> SEQ ID NO 68
<211> LENGTH: 35
<212> TYPE: DNA
<213> ORGANISM: Artificial Sequence
<220> FEATURE:
<223> OTHER INFORMATION: primer

<400> SEQUENCE: 68
ggccagtgcc aagctccccc tgtggcaaat taatc                              35

<210> SEQ ID NO 69
<211> LENGTH: 35
<212> TYPE: DNA
<213> ORGANISM: Artificial Sequence
<220> FEATURE:
<223> OTHER INFORMATION: primer

<400> SEQUENCE: 69
tgcccatccg cgtagtcctg tgtgaaattg ttatc                              35

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
ctacgcggat gggcataatc                                               20

<210> SEQ ID NO 71
<211> LENGTH: 38
<212> TYPE: DNA
<213> ORGANISM: Artificial Sequence
<220> FEATURE:
<223> OTHER INFORMATION: primer

<400> SEQUENCE: 71
ccaagcttgc atgccatttg cgcctgcaac gtaggttg                           38

<210> SEQ ID NO 72
<211> LENGTH: 38
<212> TYPE: DNA
<213> ORGANISM: Artificial Sequence
<220> FEATURE:
<223> OTHER INFORMATION: primer

<400> SEQUENCE: 72
catggagttc atcataacag gaatgttcct ttcgaaaa                           38

<210> SEQ ID NO 73
<211> LENGTH: 23
<212> TYPE: DNA
<213> ORGANISM: Artificial Sequence
<220> FEATURE:
<223> OTHER INFORMATION: primer

<400> SEQUENCE: 73
atgatgaact ccatgagcca agc                                               23

<210> SEQ ID NO 74
<211> LENGTH: 37
<212> TYPE: DNA
<213> ORGANISM: Artificial Sequence
<220> FEATURE:
<223> OTHER INFORMATION: primer

<400> SEQUENCE: 74
cggtacccgg ggatcggtct actagctttt ctgtgcc                                37

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
tcctcccaca cggctcagtc                                                   20

<210> SEQ ID NO 76
<211> LENGTH: 42
<212> TYPE: DNA
<213> ORGANISM: Artificial Sequence
<220> FEATURE:
<223> OTHER INFORMATION: primer

<400> SEQUENCE: 76
tacttgtagt tccttgtctg aaattcttcc taacctttac gc                          42

<210> SEQ ID NO 77
<211> LENGTH: 42
<212> TYPE: DNA
<213> ORGANISM: Artificial Sequence
<220> FEATURE:
<223> OTHER INFORMATION: primer

<400> SEQUENCE: 77
gcgtaaaggt taggaagaat ttcagacaag gaactacaag ta                          42

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
ggcagcgaca catgcaccac                                                   20

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
ctggatccta cgtattatcc tgctg                                             25

<210> SEQ ID NO 80
<211> LENGTH: 24
<212> TYPE: DNA
<213> ORGANISM: Artificial Sequence

```
<220> FEATURE:
<223> OTHER INFORMATION: primer

<400> SEQUENCE: 80
gcggatccag gctgcgtggt caag                                          24

<210> SEQ ID NO 81
<211> LENGTH: 77
<212> TYPE: DNA
<213> ORGANISM: Artificial Sequence
<220> FEATURE:
<223> OTHER INFORMATION: primer

<400> SEQUENCE: 81
tcaccattat gttaacacgg cttaacagtt aacctacgag gcatccgtga agcctgcttt   60
tttatactaa gttggca                                                  77

<210> SEQ ID NO 82
<211> LENGTH: 65
<212> TYPE: DNA
<213> ORGANISM: Artificial Sequence
<220> FEATURE:
<223> OTHER INFORMATION: primer

<400> SEQUENCE: 82
gcagtctggc gccgtagcgc cagacatttt tccggcgctc aagttagtat aaaaaagctg   60
aacga                                                               65

<210> SEQ ID NO 83
<211> LENGTH: 22
<212> TYPE: DNA
<213> ORGANISM: Artificial Sequence
<220> FEATURE:
<223> OTHER INFORMATION: primer

<400> SEQUENCE: 83
ataacgtaga tggcgcagtt cc                                            22

<210> SEQ ID NO 84
<211> LENGTH: 23
<212> TYPE: DNA
<213> ORGANISM: Artificial Sequence
<220> FEATURE:
<223> OTHER INFORMATION: primer

<400> SEQUENCE: 84
aggatctcag cctacctcat gcg                                           23

<210> SEQ ID NO 85
<211> LENGTH: 45
<212> TYPE: DNA
<213> ORGANISM: Artificial Sequence
<220> FEATURE:
<223> OTHER INFORMATION: primer

<400> SEQUENCE: 85
atggcggccg cttatttgat ttcaattttg tcccactccc tgcct                   45

<210> SEQ ID NO 86
<211> LENGTH: 41
<212> TYPE: DNA
<213> ORGANISM: Artificial Sequence
<220> FEATURE:
<223> OTHER INFORMATION: primer
```

```
<400> SEQUENCE: 86
atggcggccg cttatgacaa cttgacggct acatcattca c                    41

<210> SEQ ID NO 87
<211> LENGTH: 80
<212> TYPE: DNA
<213> ORGANISM: Artificial Sequence
<220> FEATURE:
<223> OTHER INFORMATION: primer

<400> SEQUENCE: 87
ggattcaggc ttgtttacta aaaaaagttt aacttcctca ggagagcaca tgaagcctgc    60 tttttttatac taagttggca                                              80

<210> SEQ ID NO 88
<211> LENGTH: 80
<212> TYPE: DNA
<213> ORGANISM: Artificial Sequence
<220> FEATURE:
<223> OTHER INFORMATION: primer

<400> SEQUENCE: 88
acgggccaga caagggtttt cggcagcccg ttcatcgggc gcggagcgga cgctcaagtt    60
agtataaaaa agctgaacga                                               80

<210> SEQ ID NO 89
<211> LENGTH: 25
<212> TYPE: DNA
<213> ORGANISM: Artificial Sequence
<220> FEATURE:
<223> OTHER INFORMATION: primer

<400> SEQUENCE: 89
cgctgcttta ttcccgtaaa tcgtg                                         25

<210> SEQ ID NO 90
<211> LENGTH: 27
<212> TYPE: DNA
<213> ORGANISM: Artificial Sequence
<220> FEATURE:
<223> OTHER INFORMATION: primer

<400> SEQUENCE: 90
cagcagtgtt taacgaagcg ataaacc                                       27

<210> SEQ ID NO 91
<211> LENGTH: 25
<212> TYPE: DNA
<213> ORGANISM: Artificial Sequence
<220> FEATURE:
<223> OTHER INFORMATION: primer

<400> SEQUENCE: 91
gtgtcgactc acacatcttc aacgc                                         25

<210> SEQ ID NO 92
<211> LENGTH: 80
<212> TYPE: DNA
<213> ORGANISM: Artificial Sequence
<220> FEATURE:
<223> OTHER INFORMATION: primer

<400> SEQUENCE: 92
ggttaaggac ggccgcacag gctgagcgga ccgtcctgac gagaatggac ttaggaaacg    60
```
acgacgatca agtcgccacc 80

<210> SEQ ID NO 93
<211> LENGTH: 80
<212> TYPE: DNA
<213> ORGANISM: Artificial Sequence
<220> FEATURE:
<223> OTHER INFORMATION: primer

<400> SEQUENCE: 93
aattccatga atttccagca gttagctgca tgtttccttc actttaagtc tgaagcctgc 60 tttttatac taagttggca 80

<210> SEQ ID NO 94
<211> LENGTH: 80
<212> TYPE: DNA
<213> ORGANISM: Artificial Sequence
<220> FEATURE:
<223> OTHER INFORMATION: primer

<400> SEQUENCE: 94
accaagatct ttttgaatgc tggaagcgtt gaagatgtgt gagtcgacac ggcagtctcc 60
ttgtgtgaaa ttgttatccg 80

<210> SEQ ID NO 95
<211> LENGTH: 80
<212> TYPE: DNA
<213> ORGANISM: Artificial Sequence
<220> FEATURE:
<223> OTHER INFORMATION: primer

<400> SEQUENCE: 95
agcaacagaa aacgttattc ttgttacatt ccctttcag gagcacaacg tgaagcctgc 60 tttttatac taagttggca 80

<210> SEQ ID NO 96
<211> LENGTH: 77
<212> TYPE: DNA
<213> ORGANISM: Artificial Sequence
<220> FEATURE:
<223> OTHER INFORMATION: primer

<400> SEQUENCE: 96
gtaactgcgc acgctaacgg gttcaggccg gataacaccg gccggatacg ttaggaaacg 60
acgacgatca agtcgcc 77

<210> SEQ ID NO 97
<211> LENGTH: 25
<212> TYPE: DNA
<213> ORGANISM: Artificial Sequence
<220> FEATURE:
<223> OTHER INFORMATION: primer

<400> SEQUENCE: 97
gtccggaagg tgaaggtttc accgc 25

<210> SEQ ID NO 98
<211> LENGTH: 23
<212> TYPE: DNA
<213> ORGANISM: Artificial Sequence
<220> FEATURE:
<223> OTHER INFORMATION: primer

<400> SEQUENCE: 98
gtgccagtta gttaacggcc gcc        23

<210> SEQ ID NO 99
<211> LENGTH: 34
<212> TYPE: DNA
<213> ORGANISM: Artificial Sequence
<220> FEATURE:
<223> OTHER INFORMATION: primer

<400> SEQUENCE: 99
ccaagcttgc atgcccatta aaaaacgtgc ccgg        34

<210> SEQ ID NO 100
<211> LENGTH: 36
<212> TYPE: DNA
<213> ORGANISM: Artificial Sequence
<220> FEATURE:
<223> OTHER INFORMATION: primer

<400> SEQUENCE: 100
cggtacccgg ggatcacgtc cggggtcaaa actctg        36

<210> SEQ ID NO 101
<211> LENGTH: 993
<212> TYPE: DNA
<213> ORGANISM: Pantoea ananatis

<400> SEQUENCE: 101
atgaaaatcg ccgtatacag tactaaacac tatgaccaga agtaccttga acaggtcaac        60
caacagtatg gtttcgaact ggtcttttt gatttttac tcagcgaaag cacggcgaag        120
acagcagtag actgcgatgc ggtatgtatc tttgtgaatg atgacggcag ccgcccggtg        180
ctcgaagagc tggcggggct gggcgtccgc tacattgccc tgcgctgtgc gggatttaac        240
aatgtcgatc tcgacgcggc agccgaactg gggcttcagg tcgtccgcgt gcctgcctac        300
tccccggagg ccgttgccga gcatgcggtg gggctgatga tgacgctgaa ccgccggatt        360
catcgcgctt accagcgcac ccgcgacgcc aatttttcgc tggacggcct gaccggtttt        420
aacatgcata caaaaacggc cggtatcatt ggcaccggca aaatcggcat cgccacgctg        480
cgcatattaa aagggttcgg aatgcgttta ctggcgtttg atccttatcc cagcgagcag        540
gctttagcgc tcggcgcgga atatgtcgat ctgaaaaccc tgtttgccga gtcgcacgtc        600
atcagtctgc actgtccact gacggcggag aaccatcatt tactcaacgc acaggctttt        660
tcgcagatgc gtgacggcgt catgatcatt aacaccagtc ggggcggatt aattgattct        720
caggctgcga ttgatgcgtt gaagcagcaa aaaataggtg cgctgggcat ggacgtttat        780
gaaaacgagc gagatctgtt ctttgaagac aaatctaatg atgtgattca ggatgatgta        840
ttccgccgcc tgtcagcctg tcataacgtg ctgtttaccg gtcatcaggc gtttctcacc        900
gccgaagccc tgacggcaat tcagacaccc acgctgaaaa acctcagcca gctaaaccgc        960
ggcgaaacct gtcagaatcg gattaccgcc tga        993

<210> SEQ ID NO 102
<211> LENGTH: 330
<212> TYPE: PRT
<213> ORGANISM: Pantoea ananatis

<400> SEQUENCE: 102

Met Lys Ile Ala Val Tyr Ser Thr Lys His Tyr Asp Gln Lys Tyr Leu

```
              1               5                  10                 15
          Glu Gln Val Asn Gln Gln Tyr Gly Phe Glu Leu Val Phe Phe Asp Phe
                          20                 25                 30
          Leu Leu Ser Glu Ser Thr Ala Lys Thr Ala Val Asp Cys Asp Ala Val
                          35                 40                 45
          Cys Ile Phe Val Asn Asp Asp Gly Ser Arg Pro Val Leu Glu Glu Leu
                          50                 55                 60
          Ala Gly Leu Gly Val Arg Tyr Ile Ala Leu Arg Cys Ala Gly Phe Asn
           65                 70                 75                 80
          Asn Val Asp Leu Asp Ala Ala Glu Leu Gly Leu Gln Val Arg
                          85                 90                 95
          Val Pro Ala Tyr Ser Pro Glu Ala Val Ala Glu His Ala Val Gly Leu
                         100                105                110
          Met Met Thr Leu Asn Arg Arg Ile His Arg Ala Tyr Gln Arg Thr Arg
                         115                120                125
          Asp Ala Asn Phe Ser Leu Asp Gly Leu Thr Gly Phe Asn Met His Asn
                         130                135                140
          Lys Thr Ala Gly Ile Ile Gly Thr Gly Lys Ile Gly Ile Ala Thr Leu
          145                150                155                160
          Arg Ile Leu Lys Gly Phe Gly Met Arg Leu Leu Ala Phe Asp Pro Tyr
                         165                170                175
          Pro Ser Glu Gln Ala Leu Ala Leu Gly Ala Glu Tyr Val Asp Leu Lys
                         180                185                190
          Thr Leu Phe Ala Glu Ser His Val Ile Ser Leu His Cys Pro Leu Thr
                         195                200                205
          Ala Glu Asn His His Leu Leu Asn Ala Gln Ala Phe Ser Gln Met Arg
                         210                215                220
          Asp Gly Val Met Ile Ile Asn Thr Ser Arg Gly Gly Leu Ile Asp Ser
          225                230                235                240
          Gln Ala Ala Ile Asp Ala Leu Lys Gln Gln Lys Ile Gly Ala Leu Gly
                         245                250                255
          Met Asp Val Tyr Glu Asn Glu Arg Asp Leu Phe Phe Glu Asp Lys Ser
                         260                265                270
          Asn Asp Val Ile Gln Asp Val Phe Arg Arg Leu Ser Ala Cys His
                         275                280                285
          Asn Val Leu Phe Thr Gly His Gln Ala Phe Leu Thr Ala Glu Ala Leu
                         290                295                300
          Thr Ala Ile Ser Asp Thr Thr Leu Glu Asn Leu Ser Gln Leu Asn Arg
          305                310                315                320
          Gly Glu Thr Cys Gln Asn Arg Ile Thr Ala
                         325                330

<210> SEQ ID NO 103
<211> LENGTH: 2688
<212> TYPE: DNA
<213> ORGANISM: Pantoea ananatis

<400> SEQUENCE: 103
atggccgtta ctaatgtcgc tgaactcaat gcactggttg aacgtgtaaa aaaagcccag      60
caagaattcg ccaatttttc tcaacaacag gtcgatgcca tcttccgcgc agccgcactg     120
gccgccgcgg atgcccgaat tccactcgct aaaatggcgg tggcggaatc gggcatgggc     180
attgttgaag acaaagtcat taaaaatcac ttcgcttctg aatacatcta caacgcctat     240
aaggatgaga aaacctgcgg cgtactggac accgatgata cgtttggcac catcaccatc     300
```

```
gctgaaccca tcggcctgat ttgcggtatt gtccccacca ctaaccctac ctcgaccgca      360
atttttaagg cacttatcag ccttaaaacc cgcaacggga ttatcttctc cccccatcct      420
cgagccaaag atgcgacgaa caaagcggcg gatattgtcc tgcaggcagc gattgccgct      480
ggcgcgccca aagacattat aggctggatt gatgcacctt ctgtggaact gtccaatcag      540
ttgatgcacc atcctgatat taacctgatt ctggcgacgg gtggcccgg catggtcaaa       600 gccgcctaca gctcaggtaa gccggcgatt ggcgtggggg ccggtaacac gcccgttgtc      660
atcgatgaaa cagctgatgt taaacgcgcc gttgcctcca tcctgatgtc aaaaacgttt      720
gataacggtg tgatctgtgc ctctgaacag tcggttatcg tggtggatgc cgtctacgac      780
gccgtgcgcg agcgcttcgc cagccatggt ggctatttgc ttcagggaca ggagctgagt      840
gcggtacaaa atatcattct aaaaaacggt gggcttaacg ccgccattgt gggccagcct      900
gcggtgaaga ttgcggagat ggccggcatc agcgtacctg gtgaaaccaa atcctgatt      960 ggcgaagttg aacgggtcga tgaatcagaa cctttcgctc atgaaaaact gtcgccgaca     1020
ctggcgatgt accgtgctaa agattatcag gatgccgtca gcaaagcgga gaaactggtg     1080
gcgatgggcg gtattggtca tacgtcatgc ctgtataccg accaggacaa tcagacagcg     1140
cgcgtgcact attttggcga caagatgaaa acagcccgca ttctgatcaa cacgccagct     1200
tctcagggcg gtattggtga tttatataac ttcaaactcg ccccttctct gacactgggt     1260
tgtggttcct ggggcggtaa ctccatttct gaaaacgtgg ggcccaaaca tctcatcaac     1320
aagaaaaccg tcgctaagcg agctgaaaat atgttgtggc ataaacttcc gaagtccatt     1380
tactttcgtc gcggctcttt acccattgcg cttgaagaga tcgccactga cggtgccaaa     1440
cgcgcgtttg tggtgactga ccgcttcctg tttaacaacg ttatgccga tcaggtcacc      1500 cgcgttttaa atctcacgg catcgaaacc gaagttttct ttgaggttga agcggatccc      1560
accttaagca tcgtgcgtaa aggtgcagaa cagatgaaca gctttaagcc agacgtgatc     1620
atcgccctgg gcggcggttc gccgatggat gcagccaaaa tcatgtgggt catgtatgag     1680
catccagaaa cccatttga agagctggca ctgcggttta tggatattcg caaacgtatc      1740
tataagttcc ctaaaatggg cgtgaaagcg cgcatggtgg ccattacgac aacctcaggc     1800
acaggttcag aagtgacgcc ttttgccgtg gtaacggatg acgcgaccgg acagaaatac     1860
ccgctggccg attatgcgct gacgccggat atggctatcg ttgatgccaa cctggtcatg     1920
gatatgccac gttcactttg tgccttcggc ggtctggatg cggtgacgca cgcgctggaa     1980
gcctatgtgt ccgttctggc caatgaatac tccgatggtc aggccctgca ggcgcttaag     2040
ctgcttaaag agaacttacc ggcgagttat gcagaaggtg caaaaaatcc ggttgcccgt     2100
gaacgtgtac ataatgccgc caccatcgcc ggtatcgcct ttgctaacgc cttcctcggg     2160
gtttgtcact caatggcgca taagcttggc tctgagttcc atattcctca tggactggct     2220
aactcgctgc tgatttccaa cgttattcgc tataacgcca atgacaaccc tactaagcaa     2280
accgcattca gccagtacga tcgtccccag gcgcgtcgtc gttatgctga aattgcggat     2340
catcttggtc tcaccgcgac gggcgaccgc actgcccaga aaattgagaa gctgctggta     2400
tggctggatg agatcaaaac ggaactgggt attccggcat cgattcgtga agccggtgtg     2460
caggaggcag acttcctggc gaaagtcgat aaactggcgg atgatgcctt tgatgaccag     2520
tgtactggcg cgaatccacg ttatccgctg attgccgaac tcaaacagct gatgctggac     2580
agctactacg gacgcaaatt tgtcgagccg ttcgccagtg ccgccgaggc tgcccaggct     2640
```
cagcctgtca gtgacagcaa agcggcgaag aaagctaaaa aagcctaa              2688

<210> SEQ ID NO 104
<211> LENGTH: 895
<212> TYPE: PRT
<213> ORGANISM: Pantoea ananatis

<400> SEQUENCE: 104

Met Ala Val Thr Asn Val Ala Glu Leu Asn Ala Leu Val Glu Arg Val
1               5                   10                  15

Lys Lys Ala Gln Gln Glu Phe Ala Asn Phe Ser Gln Gln Val Asp
            20                  25                  30

Ala Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Asp Thr Asp Thr Phe Gly
                85                  90                  95

Thr Ile Thr Ile Ala Glu Pro Ile Gly Leu Ile Cys Gly Ile Val Pro
            100                 105                 110

Thr Thr Asn Pro Thr Ser Thr Ala Ile Phe Lys Ala Leu Ile Ser Leu
        115                 120                 125

Lys Thr Arg Asn Gly Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160

Gly Ala Pro Lys Asp Ile Ile Gly Trp Ile Asp Ala Pro Ser Val Glu
                165                 170                 175

Leu Ser Asn Gln Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Val Lys Arg Ala Val Ala Ser Ile Leu Met Ser Lys Thr Phe
225                 230                 235                 240

Asp Asn Gly Val Ile Cys Ala Ser Glu Gln Ser Val Ile Val Val Asp
                245                 250                 255

Ala Val Tyr Asp Ala Val Arg Glu Arg Phe Ala Ser His Gly Gly Tyr
            260                 265                 270

Leu Leu Gln Gly Gln Glu Leu Ser Ala Val Gln Asn Ile Ile Leu Lys
        275                 280                 285

Asn Gly Gly Leu Asn Ala Ala Ile Val Gly Gln Pro Ala Val Lys Ile
    290                 295                 300

Ala Glu Met Ala Gly Ile Ser Val Pro Gly Glu Thr Lys Ile Leu Ile
305                 310                 315                 320

Gly Glu Val Glu Arg Val Asp Glu Ser Glu Pro Phe Ala His Glu Lys
                325                 330                 335

Leu Ser Pro Thr Leu Ala Met Tyr Arg Ala Lys Asp Tyr Gln Asp Ala
            340                 345                 350

Val Ser Lys Ala Glu Lys Leu Val Ala Met Gly Gly Ile Gly His Thr
        355                 360                 365

```
Ser Cys Leu Tyr Thr Asp Gln Asp Asn Gln Thr Ala Arg Val His Tyr
    370                 375                 380

Phe Gly Asp Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
                420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Glu Glu Ile Ala Thr Asp Gly Ala Lys
465                 470                 475                 480

Arg Ala Phe Val Val Thr Asp Arg Phe Leu Phe Asn Asn Gly Tyr Ala
                485                 490                 495

Asp Gln Val Thr Arg Val Leu Lys Ser His Gly Ile Glu Thr Glu Val
                500                 505                 510

Phe Phe Glu Val Glu Ala Asp Pro Thr Leu Ser Ile Val Arg Lys Gly
        515                 520                 525

Ala Glu Gln Met Asn Ser Phe Lys Pro Asp Val Ile Ala Leu Gly
    530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Arg Met
                580                 585                 590

Val Ala Ile Thr Thr Thr Ser Gly Thr Gly Ser Glu Val Thr Pro Phe
        595                 600                 605

Ala Val Val Thr Asp Asp Ala Thr Gly Gln Lys Tyr Pro Leu Ala Asp
    610                 615                 620

Tyr Ala Leu Thr Pro Asp Met Ala Ile Val Asp Ala Asn Leu Val Met
625                 630                 635                 640

Asp Met Pro Arg Ser Leu Cys Ala Phe Gly Gly Leu Asp Ala Val Thr
                645                 650                 655

His Ala Leu Glu Ala Tyr Val Ser Val Leu Ala Asn Glu Tyr Ser Asp
                660                 665                 670

Gly Gln Ala Leu Gln Ala Leu Lys Leu Leu Lys Glu Asn Leu Pro Ala
        675                 680                 685

Ser Tyr Ala Glu Gly Ala Lys Asn Pro Val Ala Arg Glu Arg Val His
    690                 695                 700

Asn Ala Ala Thr Ile Ala Gly Ile Ala Phe Ala Asn Ala Phe Leu Gly
705                 710                 715                 720

Val Cys His Ser Met Ala His Lys Leu Gly Ser Glu Phe His Ile Pro
                725                 730                 735

His Gly Leu Ala Asn Ser Leu Leu Ile Ser Asn Val Ile Arg Tyr Asn
                740                 745                 750

Ala Asn Asp Asn Pro Thr Lys Gln Thr Ala Phe Ser Gln Tyr Asp Arg
        755                 760                 765

Pro Gln Ala Arg Arg Tyr Ala Glu Ile Ala Asp His Leu Gly Leu
    770                 775                 780

Thr Ala Thr Gly Asp Arg Thr Ala Gln Lys Ile Glu Lys Leu Leu Val
```

```
                785               790              795              800
Trp Leu Asp Glu Ile Lys Thr Glu Leu Gly Ile Pro Ala Ser Ile Arg
                    805              810              815

Glu Ala Gly Val Gln Glu Ala Asp Phe Leu Ala Lys Val Asp Lys Leu
                820               825              830

Ala Asp Asp Ala Phe Asp Gln Cys Thr Gly Ala Asn Pro Arg Tyr
                835           840               845

Pro Leu Ile Ala Glu Leu Lys Gln Leu Met Leu Asp Ser Tyr Tyr Gly
    850              855              860

Arg Lys Phe Val Glu Pro Phe Ala Ser Ala Ala Glu Ala Ala Gln Ala
865              870              875              880

Gln Pro Val Ser Asp Ser Lys Ala Ala Lys Ala Lys Lys Ala
                    885              890              895
```

<210> SEQ ID NO 105
<211> LENGTH: 1680
<212> TYPE: DNA
<213> ORGANISM: Pantoea ananatis

<400> SEQUENCE: 105

| | | | |
|---|---|---|---|
| atgaaaacta tctctgatac gacactctgg cactgcggtg cagacctggt tgtcgcgcaa | 60 |
| cttgaagcgc aaggcgtcag ccatgtgttt ggcatccctg cgcaaaaat tgataaggta | 120 |
| tttgattccc tactcgattc ttccattcag acgatccccg tgcggcatga ggcgaatgcc | 180 |
| gcctttatgg ccgcggcagt aggccgtctg acgggtaacg ctggcgtggc gctggtcaca | 240 |
| tccgggccgg gctgctcaaa cctggtgacc ggtatggcta ccgcaaccag tgagggcgac | 300 |
| ccggtggtgg ctattggggg cgcggtcaaa cgctccgaca cgccaagca ggttcaccag | 360 |
| agtcttgata ccgtatccat gttccgcccg gtgacaaaat atgcggttga agtcaccgac | 420 |
| tcgtcggcac tggcggaatg tgtatcaaac gcgtttcgtc acgctgaaca cggtcgcggc | 480 |
| ggcggtgcgt ttgtcagcct gccacaggat atcgttgatc agccggtcac gggtaaggtg | 540 |
| ctgagccatc acggccgcat cacgctgggt gcggcaccgg atgtgatgat tgatgcggtc | 600 |
| agtcgcgaga tcgcccacgc aaaaaatccc gtgatcttgc tgggcctgat ggcaagccag | 660 |
| cctgagaata gcgaagccat tcacgatctg ttaaaccgca gccatatccc ggtaaccagc | 720 |
| acgtatcagg cggcgggtgc cgttcgccag gagcactttt cccgttttgc cggtcgcgtg | 780 |
| ggactttttca caatcaggc aggcgacaag ctgctgcaac aggccgacct gattattacc | 840 |
| atcggctaca gcccggttga gtatgaacct gccatgtgga cagcgggaa tgccacctta | 900 |
| atccacattg acgttgtgcc agcggaaacg gacaaccgct atttgccaga tgcggagctg | 960 |
| gtcggcaaca tcgccgccac gctgcgtaaa ctggcacaaa aggtcagcca gccgttacag | 1020 |
| ctcagcaagg aggctgccag tatccttgag gaccgtcagc agcagcggca gttacttgca | 1080 |
| ttacagggcg cgagcctgaa tcagtttgct cttcatccgc tgcgcatcgt gcgtgcgatg | 1140 |
| caggacatta tcaacagcga cgtcagcctc accgttgata tgggcagctt ccatatctgg | 1200 |
| attgcccgct atctctacag cttccgcgca cgccaaatca tgatttctaa cgggcagcaa | 1260 |
| accatgggcg tggccttgcc ctgggcgatt ggtgcctggc tggtcgatcc acagcgtaaa | 1320 |
| gtcgtctcgg tttcaggaga tggcggcttc atgcagtcaa gcatggagct ggaaaccgcc | 1380 |
| gtcaggctca cgccaacat tttacacatt gtctgggtcg ataatgctta caacatggtg | 1440 |
| gcgatgcagg aagagaaaaa atatcagcgt gtttcaggcg tgaactttgg gcccattgat | 1500 |
| tttaaagcct atgcggaagc attcggtgcg gcgggattcg cggtgaacag tgcctccgaa | 1560 |

-continued

```
ctggaaccca cgctgcgcaa agcgatggat gttcaggggc ctgctgttgt ggcagtgcca   1620
gtggattacg ccgataacca cttgctgatg gggcagcttc atctcagcca gttactttaa   1680
```

<210> SEQ ID NO 106
<211> LENGTH: 559
<212> TYPE: PRT
<213> ORGANISM: Pantoea ananatis

<400> SEQUENCE: 106

```
Met Lys Thr Ile Ser Asp Thr Thr Leu Trp His Cys Gly Ala Asp Leu
1               5                  10                  15

Val Val Ala Gln Leu Glu Ala Gln Gly Val Ser His Val Phe Gly Ile
            20                  25                  30

Pro Gly Ala Lys Ile Asp Lys Val Phe Asp Ser Leu Leu Asp Ser Ser
        35                  40                  45

Ile Gln Thr Ile Pro Val Arg His Glu Ala Asn Ala Ala Phe Met Ala
    50                  55                  60

Ala Ala Val Gly Arg Leu Thr Gly Asn Ala Gly Val Ala Leu Val Thr
65                  70                  75                  80

Ser Gly Pro Gly Cys Ser Asn Leu Val Thr Gly Met Ala Thr Ala Thr
                85                  90                  95

Ser Glu Gly Asp Pro Val Val Ala Ile Gly Gly Ala Val Lys Arg Ser
            100                 105                 110

Asp Ser Ala Lys Gln Val His Gln Ser Leu Asp Thr Val Ser Met Phe
        115                 120                 125

Arg Pro Val Thr Lys Tyr Ala Val Glu Val Thr Asp Ser Ser Ala Leu
    130                 135                 140

Ala Glu Cys Val Ser Asn Ala Phe Arg His Ala Glu His Gly Arg Gly
145                 150                 155                 160

Gly Gly Ala Phe Val Ser Leu Pro Gln Asp Ile Val Asp Gln Pro Val
                165                 170                 175

Thr Gly Lys Val Leu Ser His His Gly Arg Ile Thr Leu Gly Ala Ala
            180                 185                 190

Pro Asp Val Met Ile Asp Ala Val Ser Arg Glu Ile Ala His Ala Lys
        195                 200                 205

Asn Pro Val Ile Leu Leu Gly Leu Met Ala Ser Gln Pro Glu Asn Ser
    210                 215                 220

Glu Ala Ile His Asp Leu Leu Asn Arg Ser His Ile Pro Val Thr Ser
225                 230                 235                 240

Thr Tyr Gln Ala Ala Gly Ala Val Arg Gln Glu His Phe Ser Arg Phe
                245                 250                 255

Ala Gly Arg Val Gly Leu Phe Asn Asn Gln Ala Gly Asp Lys Leu Leu
            260                 265                 270

Gln Gln Ala Asp Leu Ile Ile Thr Ile Gly Tyr Ser Pro Val Glu Tyr
        275                 280                 285

Glu Pro Ala Met Trp Asn Ser Gly Asn Ala Thr Leu Ile His Ile Asp
    290                 295                 300

Val Val Pro Ala Glu Thr Asp Asn Arg Tyr Leu Pro Asp Ala Glu Leu
305                 310                 315                 320

Val Gly Asn Ile Ala Ala Thr Leu Arg Lys Leu Ala Gln Lys Val Ser
                325                 330                 335

Gln Pro Leu Gln Leu Ser Lys Glu Ala Ala Ser Ile Leu Glu Asp Arg
            340                 345                 350
```

```
Gln Gln Gln Arg Gln Leu Leu Ala Leu Gln Gly Ala Ser Leu Asn Gln
            355                 360                 365

Phe Ala Leu His Pro Leu Arg Ile Val Arg Ala Met Gln Asp Ile Ile
        370                 375                 380

Asn Ser Asp Val Ser Leu Thr Val Asp Met Gly Ser Phe His Ile Trp
385                 390                 395                 400

Ile Ala Arg Tyr Leu Tyr Ser Phe Arg Ala Arg Gln Ile Met Ile Ser
                405                 410                 415

Asn Gly Gln Gln Thr Met Gly Val Ala Leu Pro Trp Ala Ile Gly Ala
            420                 425                 430

Trp Leu Val Asp Pro Gln Arg Lys Val Val Ser Val Ser Gly Asp Gly
        435                 440                 445

Gly Phe Met Gln Ser Ser Met Glu Leu Glu Thr Ala Val Arg Leu Asn
    450                 455                 460

Ala Asn Ile Leu His Ile Val Trp Val Asp Asn Ala Tyr Asn Met Val
465                 470                 475                 480

Ala Met Gln Glu Glu Lys Lys Tyr Gln Arg Val Ser Gly Val Asn Phe
                485                 490                 495

Gly Pro Ile Asp Phe Lys Ala Tyr Ala Glu Ala Phe Gly Ala Ala Gly
            500                 505                 510

Phe Ala Val Asn Ser Ala Ser Glu Leu Glu Pro Thr Leu Arg Lys Ala
        515                 520                 525

Met Asp Val Gln Gly Pro Ala Val Val Ala Val Pro Val Asp Tyr Ala
    530                 535                 540

Asp Asn His Leu Leu Met Gly Gln Leu His Leu Ser Gln Leu Leu
545                 550                 555
```

<210> SEQ ID NO 107
<211> LENGTH: 783
<212> TYPE: DNA
<213> ORGANISM: Pantoea ananatis

<400> SEQUENCE: 107

```
atgagcaatt ttgtaactga ttgttcctgc gaggatcaac taaaagatac cgtccaaaag      60
ctgcgaaaaa acatgccaga agtgttatg tatcaaacct ctttgatgag tgcgctgctg     120
agtggtgttt atgacggtga accaggatt gctgacttac tgcgcaaagg tgactttggt     180
ctgggaacct tcaatcagct ggatggtgaa ctcattgcgt tcgacagcaa tgtgtatcag     240
ctgcgcgccg atggcagtgc ccggcctgct gatcctgacc agaaaacgcc atttgcggta     300
atgaccttt tcaaccccca gcataaacac gtttttgaac gcgcggttca gcgcgatgcg     360
ctgcaccagc ttatcgacag cgaaatcacc tccgacaacc agttttgtgc actgcgtgta     420
agcggacatt tttcatccgt ccagacgcgt accgttccgt gccagtgccg gccttaccga     480
tcgatgcctg aagttctggg aaaccagccc atatttgaat tcacgcatcg ccatggcgag     540
cttattggct tccgcacgcc gcagtacatg cagggtatca acgtcgcagg atatcacgaa     600
catttcatca cagacgacag aaccggcggt gggcatatcc tggattatgt gctggagcag     660
ggcacgctga cttttggtgc catcagcaag ctggtgatcg atttacctga aaacgccgac     720
tttcttaatg ccaacctgac gccggaaaac ctggatgatg ccatccgttc tgtcgaaagc     780
taa                                                                   783
```

<210> SEQ ID NO 108
<211> LENGTH: 260
<212> TYPE: PRT

<213> ORGANISM: Pantoea ananatis

<400> SEQUENCE: 108

```
Met Ser Asn Phe Val Thr Asp Cys Ser Cys Glu Asp Gln Leu Lys Asp
1               5                   10                  15

Thr Val Gln Lys Leu Arg Lys Asn Met Pro Glu Ser Val Met Tyr Gln
            20                  25                  30

Thr Ser Leu Met Ser Ala Leu Leu Ser Gly Val Tyr Asp Gly Glu Thr
        35                  40                  45

Arg Ile Ala Asp Leu Leu Arg Lys Gly Asp Phe Gly Leu Gly Thr Phe
    50                  55                  60

Asn Gln Leu Asp Gly Glu Leu Ile Ala Phe Asp Ser Asn Val Tyr Gln
65                  70                  75                  80

Leu Arg Ala Asp Gly Ser Ala Arg Pro Ala Asp Pro Asp Gln Lys Thr
                85                  90                  95

Pro Phe Ala Val Met Thr Phe Phe Gln Pro Gln His Lys His Val Phe
            100                 105                 110

Glu Arg Ala Val Gln Arg Asp Ala Leu His Gln Leu Ile Asp Ser Glu
        115                 120                 125

Ile Thr Ser Asp Asn Gln Phe Cys Ala Leu Arg Val Ser Gly His Phe
    130                 135                 140

Ser Ser Val Gln Thr Arg Thr Val Pro Cys Gln Cys Arg Pro Tyr Arg
145                 150                 155                 160

Ser Met Pro Glu Val Leu Gly Asn Gln Pro Ile Phe Glu Phe Thr His
                165                 170                 175

Arg His Gly Glu Leu Ile Gly Phe Arg Thr Pro Gln Tyr Met Gln Gly
            180                 185                 190

Ile Asn Val Ala Gly Tyr His Glu His Phe Ile Thr Asp Asp Arg Thr
        195                 200                 205

Gly Gly Gly His Ile Leu Asp Tyr Val Leu Glu Gln Gly Thr Leu Thr
    210                 215                 220

Phe Gly Ala Ile Ser Lys Leu Val Ile Asp Leu Pro Glu Asn Ala Asp
225                 230                 235                 240

Phe Leu Asn Ala Asn Leu Thr Pro Glu Asn Leu Asp Asp Ala Ile Arg
                245                 250                 255

Ser Val Glu Ser
            260
```

<210> SEQ ID NO 109
<211> LENGTH: 768
<212> TYPE: DNA
<213> ORGANISM: Pantoea ananatis

<400> SEQUENCE: 109

```
atgcgggttg cgcttgtgac aggtgcgggt cagggcattg gtgaggcgat agccttacgt    60
ctggcaaaag acggatttgc cgtggccgtg gctgattaca atattgaaac cgcgtcgcag   120
gttgcggaaa agatcaagaa agatggcggc cgtgcgctgg ccatcaaggt ggatgtaaca   180
aaacgggatc aggtatttca tgccgttgaa gaagcgcgca gcgtatttgg gtgattttaac   240 gtcattgtga ataacgcagg tgtcgcgccc tcaacgccca ttgatgaaat caccgaagag   300
gtcatcaaca aggtttacga cgttaatgtc aaaggcgtga tctggggcat gcaggcagca   360
ataaaagcgt tcgcgtctga aggtcatggc ggaaaaatta ttaacgcctg ttctcaggcc   420
gggcatgtcg gcaatcccga gctggcagtt tacagctcaa gcaagtttgc tgttcggggc   480
```

```
ctgacacaaa ctgccgcacg ggatctggca ccggcgggga tcaccgtgaa tggcttttgt     540
cctggtattg ttaaaacacc gatgtgggcg gagatcgaca ggcagatttc cgaagcggca     600
ggcaaacccg tgggttatgg tactcaggag tttgcgaaaa gaatcacgct tggtcggtta     660
tcagaacccg aagatgtcgc agcctgtgtc gcctttcttg ccggcccgga ttctgattac     720
atcaccggac agtcgttact ggtagacggt ggcatggtgt ttagctaa                 768
```

<210> SEQ ID NO 110
<211> LENGTH: 255
<212> TYPE: PRT
<213> ORGANISM: Pantoea ananatis

<400> SEQUENCE: 110

```
Met Arg Val Ala Leu Val Thr Gly Ala Gly Gln Gly Ile Gly Glu Ala
1               5                   10                  15

Ile Ala Leu Arg Leu Ala Lys Asp Gly Phe Ala Val Ala Val Ala Asp
                20                  25                  30

Tyr Asn Ile Glu Thr Ala Ser Gln Val Ala Glu Lys Ile Lys Lys Asp
            35                  40                  45

Gly Gly Arg Ala Leu Ala Ile Lys Val Asp Val Thr Lys Arg Asp Gln
        50                  55                  60

Val Phe His Ala Val Glu Glu Ala Arg Ser Val Leu Gly Asp Phe Asn
65                  70                  75                  80

Val Ile Val Asn Asn Ala Gly Val Ala Pro Ser Thr Pro Ile Asp Glu
                85                  90                  95

Ile Thr Glu Glu Val Ile Asn Lys Val Tyr Asp Val Asn Val Lys Gly
            100                 105                 110

Val Ile Trp Gly Met Gln Ala Ala Ile Lys Ala Phe Ala Ser Glu Gly
        115                 120                 125

His Gly Gly Lys Ile Ile Asn Ala Cys Ser Gln Ala Gly His Val Gly
    130                 135                 140

Asn Pro Glu Leu Ala Val Tyr Ser Ser Ser Lys Phe Ala Val Arg Gly
145                 150                 155                 160

Leu Thr Gln Thr Ala Ala Arg Asp Leu Ala Pro Ala Gly Ile Thr Val
                165                 170                 175

Asn Gly Phe Cys Pro Gly Ile Val Lys Thr Pro Met Trp Ala Glu Ile
            180                 185                 190

Asp Arg Gln Ile Ser Glu Ala Ala Gly Lys Pro Val Gly Tyr Gly Thr
        195                 200                 205

Gln Glu Phe Ala Lys Arg Ile Thr Leu Gly Arg Leu Ser Glu Pro Glu
    210                 215                 220

Asp Val Ala Ala Cys Val Ala Phe Leu Ala Gly Pro Asp Ser Asp Tyr
225                 230                 235                 240

Ile Thr Gly Gln Ser Leu Leu Val Asp Gly Gly Met Val Phe Ser
                245                 250                 255
```

<210> SEQ ID NO 111
<211> LENGTH: 1767
<212> TYPE: DNA
<213> ORGANISM: Pantoea ananatis

<400> SEQUENCE: 111

```
atgagtttac cagtaagaga atttgatgcc gtggtgatcg cgcaggcgg cgcgggtatg      60 cgcgcggcgt tgcaaatctc ccagtcgggc cagacctgtg ccctgttgtc caaagtcttc    120 ccgaccgtt cccatacggt ctccgcgcag ggcggaatca ccgttgcgct gggtaacacc    180
```

-continued

```
catgacgata actgggaatg gcatatgtat gacaccgtca aaggttccga ctacatcggt       240
gaccaggacg cgatcgaata catgtgtcac gtcggtccgg aagcgattct ggaactggag       300
cacatgggct tgcccttctc ccgtcttgat gacggccgcg tttatcagcg tccgtttggt       360
ggtcagtcga aaaacttcgg cggtgagcag gcggcgcgta ctgccgcagc ggccgaccgt       420
accggccacg cactgctgca tacgctgtat cagcagaacc tgaaaaataa aaccactatc       480
ttctccgaat ggtatgcact ggatctggtc aaaaatgacg acggtgccat cgtaggctgt       540
acggcaatct gcatggaaac cggcgaaacg gtttacttca aagccaaggc caccattctg       600
gcgacgggcg tgcaggacg tatttatcag tccacgacga acgcccacat caataccggc       660
gacggtgttg gcatggcgct gcgcgcgggc gtgcctgtgc aggatatgga aatgtggcag       720
ttccacccaa ccggtatcgc cggtgctggt gtactggtca ccgaaggctg tcgtggtgaa       780
ggcggttatc tgctgaacaa acacggtgag cgtttcatgg agcgctatgc gcctaacgcc       840
aaagaccttg ccggtcgtga cgttgtggcc cgttcgatga tggtggagat ccgtgaaggt       900
cgtggttgcg acggtccatg gggcccgcac atcaagctga aactcgatca cctgggtgcg       960
gaagtgctgg aatcgcgcct gccgggcatc cttgagctgt cccgtacctt tgctcacgtt      1020
gacccgatta aagagccgat tccggttatc ccaacctgtc actacatgat gggcggcgtg      1080
ccaaccaaag tcaccggtca ggcgctgcgt gtgaatgagc agggcgaaga tgaagtgatt      1140
cctggcctgt tcgcggtggg tgaaatcgcc tgcgtatcgg tacacggggc gaaccgtctg      1200
ggtggcaact cgctgctgga cctggtggtc ttcggtcgcg cggctggcgt gcatctgctt      1260
gaatgtctgg aagagcaggg tgaactgcgt gaagccagcc aggaaaacat tgatgccgcg      1320
atggcgcgtt tcaaccgctg ggaaaataac accacgggtg aagatccggt tgaaatccgc      1380
aaggcgttgc aacgctgcat gcagaacaac ttctcggtat tccgtgaagg cgatgcgatg      1440
cgtgaagggc ttgctgaact gaaagagatc cgtgagcgtc tgaagtccgc gcgcctggat      1500
gaccgctcac ctgacttcaa tacacagcgt attgagtgcc ttgagctgga taacctgatg      1560
gaaaccgctt atgccaccgc agtggcggcc aactaccgca ctgagagccg tggcgcacac      1620
agtcgcttcg actatccgga acgtgatgat gccaactggc tgtgccatag cctctatgtt      1680
ccgcaaacgg aaagcatgac gcgccgtgag gtgaacatgc aaccgaaact gcgtgcggcc      1740
ttcccgccga aagcgcgtac ctactaa                                          1767
```

<210> SEQ ID NO 112
<211> LENGTH: 588
<212> TYPE: PRT
<213> ORGANISM: Pantoea ananatis

<400> SEQUENCE: 112

```
Met Ser Leu Pro Val Arg Glu Phe Asp Ala Val Val Ile Gly Ala Gly
1               5                   10                  15

Gly Ala Gly Met Arg Ala Ala Leu Gln Ile Ser Gln Ser Gly Gln Thr
            20                  25                  30

Cys Ala Leu Leu Ser Lys Val Phe Pro Thr Arg Ser His Thr Val Ser
        35                  40                  45

Ala Gln Gly Gly Ile Thr Val Ala Leu Gly Asn Thr His Asp Asp Asn
    50                  55                  60

Trp Glu Trp His Met Tyr Asp Thr Val Lys Gly Ser Asp Tyr Ile Gly
65                  70                  75                  80

Asp Gln Asp Ala Ile Glu Tyr Met Cys His Val Gly Pro Glu Ala Ile
```

-continued

```
                85                  90                  95
Leu Glu Leu Glu His Met Gly Leu Pro Phe Ser Arg Leu Asp Asp Gly
            100                 105                 110

Arg Val Tyr Gln Arg Pro Phe Gly Gly Gln Ser Lys Asn Phe Gly Gly
            115                 120                 125

Glu Gln Ala Ala Arg Thr Ala Ala Ala Asp Arg Thr Gly His Ala
        130                 135                 140

Leu Leu His Thr Leu Tyr Gln Gln Asn Leu Lys Asn Lys Thr Thr Ile
145                 150                 155                 160

Phe Ser Glu Trp Tyr Ala Leu Asp Leu Val Lys Asn Asp Gly Ala
                165                 170                 175

Ile Val Gly Cys Thr Ala Ile Cys Met Glu Thr Gly Glu Thr Val Tyr
            180                 185                 190

Phe Lys Ala Lys Ala Thr Ile Leu Ala Thr Gly Gly Ala Gly Arg Ile
        195                 200                 205

Tyr Gln Ser Thr Thr Asn Ala His Ile Asn Thr Gly Asp Gly Val Gly
        210                 215                 220

Met Ala Leu Arg Ala Gly Val Pro Val Gln Asp Met Glu Met Trp Gln
225                 230                 235                 240

Phe His Pro Thr Gly Ile Ala Gly Ala Gly Val Leu Val Thr Glu Gly
                245                 250                 255

Cys Arg Gly Glu Gly Gly Tyr Leu Leu Asn Lys His Gly Glu Arg Phe
            260                 265                 270

Met Glu Arg Tyr Ala Pro Asn Ala Lys Asp Leu Ala Gly Arg Asp Val
        275                 280                 285

Val Ala Arg Ser Met Met Val Glu Ile Arg Glu Gly Arg Gly Cys Asp
        290                 295                 300

Gly Pro Trp Gly Pro His Ile Lys Leu Lys Leu Asp His Leu Gly Ala
305                 310                 315                 320

Glu Val Leu Glu Ser Arg Leu Pro Gly Ile Leu Glu Leu Ser Arg Thr
                325                 330                 335

Phe Ala His Val Asp Pro Ile Lys Glu Pro Ile Pro Val Ile Pro Thr
            340                 345                 350

Cys His Tyr Met Met Gly Gly Val Pro Thr Lys Val Thr Gly Gln Ala
        355                 360                 365

Leu Arg Val Asn Glu Gln Gly Glu Asp Glu Val Ile Pro Gly Leu Phe
        370                 375                 380

Ala Val Gly Glu Ile Ala Cys Val Ser Val His Gly Ala Asn Arg Leu
385                 390                 395                 400

Gly Gly Asn Ser Leu Leu Asp Leu Val Val Phe Gly Arg Ala Ala Gly
                405                 410                 415

Val His Leu Leu Glu Cys Leu Glu Glu Gln Gly Glu Leu Arg Glu Ala
            420                 425                 430

Ser Gln Glu Asn Ile Asp Ala Ala Met Ala Arg Phe Asn Arg Trp Glu
        435                 440                 445

Asn Asn Thr Thr Gly Glu Asp Pro Val Glu Ile Arg Lys Ala Leu Gln
        450                 455                 460

Arg Cys Met Gln Asn Asn Phe Ser Val Phe Arg Glu Gly Asp Ala Met
465                 470                 475                 480

Arg Glu Gly Leu Ala Glu Leu Lys Glu Ile Arg Glu Arg Leu Lys Ser
                485                 490                 495

Ala Arg Leu Asp Asp Arg Ser Pro Asp Phe Asn Thr Gln Arg Ile Glu
            500                 505                 510
```

```
Cys Leu Glu Leu Asp Asn Leu Met Glu Thr Ala Tyr Ala Thr Ala Val
            515                 520                 525

Ala Ala Asn Tyr Arg Thr Glu Ser Arg Gly Ala His Ser Arg Phe Asp
        530                 535                 540

Tyr Pro Glu Arg Asp Asp Ala Asn Trp Leu Cys His Ser Leu Tyr Val
545                 550                 555                 560

Pro Gln Thr Glu Ser Met Thr Arg Arg Glu Val Asn Met Gln Pro Lys
                565                 570                 575

Leu Arg Ala Ala Phe Pro Pro Lys Ala Arg Thr Tyr
            580                 585

<210> SEQ ID NO 113
<211> LENGTH: 939
<212> TYPE: DNA
<213> ORGANISM: Pantoea ananatis

<400> SEQUENCE: 113
atgaaagttg ccgtactcgg tgccgctggt ggcataggcc aggcgctagc acttctactc     60
aaaacccagc ttcccgcagg ttcagaactt tctctctacg acatcgcgcc cgtcacgcct    120
ggcgtcgcgg tcgatctcag ccacattcct accgcagtta cgttaaggg ttttagtggg    180 gaagatgcca ccccggcttt aaaaggtgcg gatgtcgtgc tcatctctgc tggggtagcg    240
cgtaagcctg gtatggatcg ggccgatttg tttaacgtca atgccggcat cgtgcgtaat    300
ttgattgagc aggttgctac gacagcgccg aaagcgttaa ttggggtgat caccaatccg    360
gttaacacta cggtggcgat tgcggccgag gtcctgaaga acacggtgt ttatgacaag    420 aatcgactgt ttggcgtgac aacgctggac attattcgcg ccaatacctt tgtcgctgag    480
ctgaaaggca aacagcctgg cgaggtgaac gtgcccgtgg tggggggaca ctcaggcgtc    540
actattctgc cattactgtc ccaggttgcg ggcgtcagct ttagcgatca ggaagtggct    600
gacctcacca aacgtattca aaacgccggt acagaagtgg tggaagcgaa ggccggtggg    660
gggtcagcaa cgttatccat ggggcaggcc gccgcccgtt tcggtttatc gctggtacgt    720
gccttaaacg gcgaagcgaa cgttgtggag tgtgcctacg tggaaggcga tggcgagcat    780
gcccgcttct ctctcagcc cctgctgtta ggtaaaaacg gcgtggcgga cgtaagcct    840 gttggtgccc ttagcccgtt cgaacagcag gcgctggatg gcatgctgga aacactgaaa    900
aaagatatcg cgcagggcga agcttttgtg aagcaataa                           939

<210> SEQ ID NO 114
<211> LENGTH: 312
<212> TYPE: PRT
<213> ORGANISM: Pantoea ananatis

<400> SEQUENCE: 114

Met Lys Val Ala Val Leu Gly Ala Ala Gly Gly Ile Gly Gln Ala Leu
1               5                   10                  15

Ala Leu Leu Leu Lys Thr Gln Leu Pro Ala Gly Ser Glu Leu Ser Leu
            20                  25                  30

Tyr Asp Ile Ala Pro Val Thr Pro Gly Val Ala Val Asp Leu Ser His
        35                  40                  45

Ile Pro Thr Ala Val Asn Val Lys Gly Phe Ser Gly Glu Asp Ala Thr
    50                  55                  60

Pro Ala Leu Lys Gly Ala Asp Val Val Leu Ile Ser Ala Gly Val Ala
65                  70                  75                  80
```

```
Arg Lys Pro Gly Met Asp Arg Ala Asp Leu Phe Asn Val Asn Ala Gly
                 85                  90                  95
Ile Val Arg Asn Leu Ile Glu Gln Val Ala Thr Thr Ala Pro Lys Ala
            100                 105                 110
Leu Ile Gly Val Ile Thr Asn Pro Val Asn Thr Thr Val Ala Ile Ala
            115                 120                 125
Ala Glu Val Leu Lys Lys His Gly Val Tyr Asp Lys Asn Arg Leu Phe
        130                 135                 140
Gly Val Thr Thr Leu Asp Ile Ile Arg Ala Asn Thr Phe Val Ala Glu
145                 150                 155                 160
Leu Lys Gly Lys Gln Pro Gly Glu Val Asn Val Pro Val Val Gly Gly
                165                 170                 175
His Ser Gly Val Thr Ile Leu Pro Leu Leu Ser Gln Val Ala Gly Val
            180                 185                 190
Ser Phe Ser Asp Gln Glu Val Ala Asp Leu Thr Lys Arg Ile Gln Asn
        195                 200                 205
Ala Gly Thr Glu Val Val Glu Ala Lys Ala Gly Gly Ser Ala Thr
        210                 215                 220
Leu Ser Met Gly Gln Ala Ala Ala Arg Phe Gly Leu Ser Leu Val Arg
225                 230                 235                 240
Ala Leu Asn Gly Glu Ala Asn Val Val Glu Cys Ala Tyr Val Glu Gly
                245                 250                 255
Asp Gly Glu His Ala Arg Phe Phe Ser Gln Pro Leu Leu Gly Lys
            260                 265                 270
Asn Gly Val Ala Glu Arg Lys Pro Val Gly Ala Leu Ser Pro Phe Glu
            275                 280                 285
Gln Gln Ala Leu Asp Gly Met Leu Glu Thr Leu Lys Lys Asp Ile Ala
        290                 295                 300
Gly Glu Ala Phe Val Lys Gln
305                 310

<210> SEQ ID NO 115
<211> LENGTH: 1614
<212> TYPE: DNA
<213> ORGANISM: Pantoea ananatis

<400> SEQUENCE: 115
atgtgcaaat cagctgtaaa tcttgcgctc atgatgagtg ttagcggaaa ggacaccacc      60
agggcgcagg agcgtaaaga cgttgatgta ctgcttattg gcgcaggcgt catgagtgct     120
acgttaggaa cctggcttca ggatctggaa cctgactggt ccatcgaaat ggtggagcgg     180
ctgggacacg tagcggaaga gtcttcaaat ggctggaaca acgcgggtac aggccatgcg     240
gcgctggccg agttgaacta tacgcctcag cgagccgatg cagtatcga tatcgccaaa     300 gccgttgcga ttaacgagtc attccaaatt tctcgccagt tctgggctta tcacgttcag     360
aaaggcaacc tgcatacgcc gaaaagcttt attcacagca ctccgcacat gagctttgtc     420
tggggcgatg ataatgtcgc gttcctgcgc aagcgcttta ctgccttaca gaaaagcacg     480
ctgttccgcg gcatggctta ctctgaagat ccgcaacaaa tcgcacagtg gattccgctg     540
gtcatgaaag ccgtgcgtc gaatcagaaa gtggcagcaa cctggacaga catgggtacc     600
gacgtcgatt tcggtgaagt aacgcgccag ctgattgctt cactggagca aaaagccaac     660
ttccgtttac ggatgcatca ggaagtgcgc gagattaccc gccttaatga tggccgctgg     720
caggtgacgc tcgtctgcat gaaagagggt acacgccgca cgttgacggc tggaaagatc     780
```

-continued

```
tttattggcg cgggcggtgc ggcgctgccg ctgctgcaga aggccggcat tccggaagcc    840
aacggctatg cgggcttccc ggttggcggt tccttcctgg tcaccgagaa tccagacgtc    900
gtgaaacagc acatggcgaa agtctatggc aaagccagcg tgggcgcgcc accgatgtcc    960
gtgccccatg tcgatacgcg tgtgctgaac ggcaagcagg tgctgctgtt tggtcccttt   1020
gcgaccttct cgaccaaatt cctgaagcag ggctcgctgc tggatatgtt tgcctcactc   1080
aacagcacca acgtaatgcc catgatcaag gtcggactga aaagctttga tctggtgaaa   1140
tacctgatgg atcaggtgct gcaaagtgac cgcgatcgta tggatgcact gcgtgcttat   1200
gtgccacagg cgaaacagga agactggcgc tggtgacgg ccgggcagcg cgtgcaaatc    1260
atcaagaaag atgagaaaga aggcgcagtg ctgcgtttag cacggaagt ggtgtcgtcc    1320 gaagacggct ctgtctcagc gctgctgggt gcctcgccag gtgcctcgac cgccgcgccg   1380
attatgctgg agctgctgca taaggtctat ccggagcaga tggcgtcgcc ggagtggcaa   1440
aataaaatcc gtgccgtggt gccgtcctgg ggcgtaagc tgaatggcga tgtggcgctg    1500
actgaaaaag tactggcaga aaccagccgt atcctgcagc tcaaatacac gccggttacg   1560
ccagtggctg ccaacgatga aggccgtgaa accgcctatg tcataggcaa ataa         1614
```

<210> SEQ ID NO 116
<211> LENGTH: 537
<212> TYPE: PRT
<213> ORGANISM: Pantoea ananatis

<400> SEQUENCE: 116

```
Met Cys Lys Ser Ala Val Asn Leu Ala Leu Met Met Ser Val Ser Gly
1               5                   10                  15

Lys Asp Thr Thr Arg Ala Gln Glu Arg Lys Asp Val Asp Val Leu Leu
                20                  25                  30

Ile Gly Ala Gly Val Met Ser Ala Thr Leu Gly Thr Trp Leu Gln Asp
            35                  40                  45

Leu Glu Pro Asp Trp Ser Ile Glu Met Val Glu Arg Leu Gly His Val
        50                  55                  60

Ala Glu Glu Ser Ser Asn Gly Trp Asn Asn Ala Gly Thr Gly His Ala
65                  70                  75                  80

Ala Leu Ala Glu Leu Asn Tyr Thr Pro Gln Arg Ala Asp Gly Ser Ile
                85                  90                  95

Asp Ile Ala Lys Ala Val Ala Ile Asn Glu Ser Phe Gln Ile Ser Arg
            100                 105                 110

Gln Phe Trp Ala Tyr His Val Gln Lys Gly Asn Leu His Thr Pro Lys
        115                 120                 125

Ser Phe Ile His Ser Thr Pro His Met Ser Phe Val Trp Gly Asp Asp
    130                 135                 140

Asn Val Ala Phe Leu Arg Lys Arg Phe Thr Ala Leu Gln Lys Ser Thr
145                 150                 155                 160

Leu Phe Arg Gly Met Ala Tyr Ser Glu Asp Pro Gln Gln Ile Ala Gln
                165                 170                 175

Trp Ile Pro Leu Val Met Lys Gly Arg Ala Ser Asn Gln Lys Val Ala
            180                 185                 190

Ala Thr Trp Thr Asp Met Gly Thr Asp Val Asp Phe Gly Glu Val Thr
        195                 200                 205

Arg Gln Leu Ile Ala Ser Leu Glu Gln Lys Ala Asn Phe Arg Leu Arg
    210                 215                 220

Met His Gln Glu Val Arg Glu Ile Thr Arg Leu Asn Asp Gly Arg Trp
```

```
                225                 230                 235                 240
        Gln Val Thr Leu Val Cys Met Lys Glu Gly Thr Arg Arg Thr Leu Thr
                            245                 250                 255
        Ala Gly Lys Ile Phe Ile Gly Ala Gly Gly Ala Ala Leu Pro Leu Leu
                            260                 265                 270
        Gln Lys Ala Gly Ile Pro Glu Ala Asn Gly Tyr Ala Gly Phe Pro Val
                            275                 280                 285
        Gly Gly Ser Phe Leu Val Thr Glu Asn Pro Asp Val Val Lys Gln His
                    290                 295                 300
        Met Ala Lys Val Tyr Gly Lys Ala Ser Val Gly Ala Pro Pro Met Ser
        305                 310                 315                 320
        Val Pro His Val Asp Thr Arg Val Leu Asn Gly Lys Gln Val Leu Leu
                            325                 330                 335
        Phe Gly Pro Phe Ala Thr Phe Ser Thr Lys Phe Leu Lys Gln Gly Ser
                            340                 345                 350
        Leu Leu Asp Met Phe Ala Ser Leu Asn Ser Thr Asn Val Met Pro Met
                            355                 360                 365
        Ile Lys Val Gly Leu Lys Ser Phe Asp Leu Val Lys Tyr Leu Met Asp
                    370                 375                 380
        Gln Val Leu Gln Ser Asp Arg Asp Arg Met Asp Ala Leu Arg Ala Tyr
        385                 390                 395                 400
        Val Pro Gln Ala Lys Gln Glu Asp Trp Arg Leu Val Thr Ala Gly Gln
                            405                 410                 415
        Arg Val Gln Ile Ile Lys Lys Asp Glu Lys Glu Gly Ala Val Leu Arg
                            420                 425                 430
        Leu Gly Thr Glu Val Val Ser Ser Glu Asp Gly Ser Val Ser Ala Leu
                            435                 440                 445
        Leu Gly Ala Ser Pro Gly Ala Ser Thr Ala Ala Pro Ile Met Leu Glu
                    450                 455                 460
        Leu Leu His Lys Val Tyr Pro Glu Gln Met Ala Ser Pro Glu Trp Gln
        465                 470                 475                 480
        Asn Lys Ile Arg Ala Val Val Pro Ser Trp Gly Arg Lys Leu Asn Gly
                            485                 490                 495
        Asp Val Ala Leu Thr Glu Lys Val Leu Ala Glu Thr Ser Arg Ile Leu
                            500                 505                 510
        Gln Leu Lys Tyr Thr Pro Val Thr Pro Val Ala Ala Asn Asp Glu Gly
                            515                 520                 525
        Arg Glu Thr Ala Tyr Val Ile Gly Lys
                    530                 535

<210> SEQ ID NO 117
<211> LENGTH: 1650
<212> TYPE: DNA
<213> ORGANISM: Pantoea ananatis

<400> SEQUENCE: 117
atgattaaat caactaaatt tgtacctgca ctgtcgcttg cagcgttact cgtttcttca      60
gtgacccacg ctgaaaattc accagaaaaa acagatgttc tgctgattgg cggcggtatc    120
atgagcgcct ctctgggcac cctgctggaa gagctgcaac cgggctggaa acagatcatg    180
gttgagaaac ttgatggcgt agcgctggaa tcctctaacg gctggaacaa cgccggtacc    240
ggccactcag ccaacatgga actgaactac acgccagagc gtgcagacgg ttctattgac    300
gtgaccaaag cgctggaaat caacgaagcc ttcatgattt ctcgtcagtt ctggagctct    360
```

```
caggttaaag acggcgtgtt aaataatccg cgttcgttca ttaactcaac gccgcacatg    420
agctttgtct ggggcgataa cgttgattat ctgacgaaac gctatgccgc actgcagaaa    480
actgtgctgt tccagggcat gaagttctca accgatcaca agcagatcgc gcagtgggcg    540
ccgctggtta tggaaggtcg cgatccacaa caaaaagtgg ctgctacctg gacgccagta    600
ggaaccgacg ttaactatgg tgaaatcacc cgtcagttaa ttggcagcct gaagaagaac    660
gataatttcc gcctggaaac ctcttcggaa gtgaccgatt ttaaacgtaa cagtgataat    720
tcctggcacg ttaccattaa agacgccaaa aatggcggcg aacgtaccgt agacgcgaaa    780
tacgtcttta tcggtgcagg tggcggtgcg cttaaactgc tgcaaaaaac cggtattccg    840
gaagccgaca attacgcagg tttcccggta gggggatcct tcctggtgac agagaatagc    900
gcgattgccg atcgccatct ggcaaaagtg tatggtcagg cttccgtggg tgcgccaccg    960
atgtcggttc cgcatctgga tacccgttac cttgatggta agcgtgtcgt gctgtttgga    1020
cctttcgcaa cgttctcaac caagttcctg aaaaatggtt cgttgtttga tttactgagc    1080
acaacgacca cccacaactt tatgccgatg acccacgtag gcatggataa ctttgacctg    1140
gtcaaatacc tgatcggtca ggttatgttg agcgatgatg accgttttgc cgcgctgaaa    1200
gagtactatc ctgaagcgaa gaagaagac tggaaactga ttcaggccgg tcagcgcgtg    1260
cagatcatca aaaggatgc ggataaaggc ggcgtgctga aactgggtac ggaaattgtg    1320
accgatcagc agaaaaccgt tgccgcattg ctgggtgcat cgcctggcgc atccacggct    1380
gcacctatcg caatcaatgt gatgcagaaa ctgttccctg aacaattcaa gtcagcagaa    1440
tggcaggaaa aaatccgtaa aatcgttcct gcttacggcc aaaaactgaa cgacaaccct    1500
gcgctcacac agcaggtctg ggatgaaacg gcagcaacgc tgcagctgac caagccgccg    1560
gttattcaga tgggcaatca gccaactgaa gcgcccgctg ctaacagcga aaagccccca    1620
gcctcggcga agcacgatat ggcgctgtaa                                     1650

<210> SEQ ID NO 118
<211> LENGTH: 549
<212> TYPE: PRT
<213> ORGANISM: Pantoea ananatis

<400> SEQUENCE: 118

Met Ile Lys Ser Thr Lys Phe Val Pro Ala Leu Ser Leu Ala Ala Leu
1               5                   10                  15

Leu Val Ser Ser Val Thr His Ala Glu Asn Ser Pro Glu Lys Thr Asp
                20                  25                  30

Val Leu Leu Ile Gly Gly Gly Ile Met Ser Ala Ser Leu Gly Thr Leu
            35                  40                  45

Leu Glu Glu Leu Gln Pro Gly Trp Lys Gln Ile Met Val Glu Lys Leu
        50                  55                  60

Asp Gly Val Ala Leu Glu Ser Ser Asn Gly Trp Asn Ala Gly Thr
65                  70                  75                  80

Gly His Ser Ala Asn Met Glu Leu Asn Tyr Thr Pro Glu Arg Ala Asp
                85                  90                  95

Gly Ser Ile Asp Val Thr Lys Ala Leu Glu Ile Asn Glu Ala Phe Met
            100                 105                 110

Ile Ser Arg Gln Phe Trp Ser Ser Gln Val Lys Asp Gly Val Leu Asn
        115                 120                 125

Asn Pro Arg Ser Phe Ile Asn Ser Thr Pro His Met Ser Phe Val Trp
    130                 135                 140
```

```
Gly Asp Asn Val Asp Tyr Leu Thr Lys Arg Tyr Ala Ala Leu Gln Lys
145                 150                 155                 160

Thr Val Leu Phe Gln Gly Met Lys Phe Ser Thr Asp His Lys Gln Ile
                165                 170                 175

Ala Gln Trp Ala Pro Leu Val Met Glu Gly Arg Asp Pro Gln Gln Lys
            180                 185                 190

Val Ala Ala Thr Trp Thr Pro Val Gly Thr Asp Val Asn Tyr Gly Glu
        195                 200                 205

Ile Thr Arg Gln Leu Ile Gly Ser Leu Lys Lys Asn Asp Asn Phe Arg
    210                 215                 220

Leu Glu Thr Ser Ser Glu Val Thr Asp Phe Lys Arg Asn Ser Asp Asn
225                 230                 235                 240

Ser Trp His Val Thr Ile Lys Asp Ala Lys Asn Gly Gly Glu Arg Thr
                245                 250                 255

Val Asp Ala Lys Tyr Val Phe Ile Gly Ala Gly Gly Ala Leu Lys
                260                 265                 270

Leu Leu Gln Lys Thr Gly Ile Pro Glu Ala Asp Asn Tyr Ala Gly Phe
            275                 280                 285

Pro Val Gly Gly Ser Phe Leu Val Thr Glu Asn Ser Ala Ile Ala Asp
        290                 295                 300

Arg His Leu Ala Lys Val Tyr Gly Gln Ala Ser Val Gly Ala Pro Pro
305                 310                 315                 320

Met Ser Val Pro His Leu Asp Thr Arg Tyr Leu Asp Gly Lys Arg Val
                325                 330                 335

Val Leu Phe Gly Pro Phe Ala Thr Phe Ser Thr Lys Phe Leu Lys Asn
            340                 345                 350

Gly Ser Leu Phe Asp Leu Leu Ser Thr Thr Thr His Asn Phe Met
            355                 360                 365

Pro Met Thr His Val Gly Met Asp Asn Phe Asp Leu Val Lys Tyr Leu
    370                 375                 380

Ile Gly Gln Val Met Leu Ser Asp Asp Arg Phe Ala Ala Leu Lys
385                 390                 395                 400

Glu Tyr Tyr Pro Glu Ala Lys Lys Glu Asp Trp Lys Leu Ile Gln Ala
            405                 410                 415

Gly Gln Arg Val Gln Ile Ile Lys Lys Asp Ala Asp Lys Gly Gly Val
            420                 425                 430

Leu Lys Leu Gly Thr Glu Ile Val Thr Asp Gln Gln Lys Thr Val Ala
        435                 440                 445

Ala Leu Leu Gly Ala Ser Pro Gly Ala Ser Thr Ala Ala Pro Ile Ala
    450                 455                 460

Ile Asn Val Met Gln Lys Leu Phe Pro Glu Gln Phe Lys Ser Ala Glu
465                 470                 475                 480

Trp Gln Glu Lys Ile Arg Lys Ile Val Pro Ala Tyr Gly Gln Lys Leu
                485                 490                 495

Asn Asp Asn Pro Ala Leu Thr Gln Gln Val Trp Asp Glu Thr Ala Ala
            500                 505                 510

Thr Leu Gln Leu Thr Lys Pro Pro Val Ile Gln Met Gly Asn Gln Pro
            515                 520                 525

Thr Glu Ala Pro Ala Ala Asn Ser Glu Lys Ala Pro Ala Ser Ala Lys
            530                 535                 540

His Asp Met Ala Leu
545
```

<210> SEQ ID NO 119
<211> LENGTH: 1698
<212> TYPE: DNA
<213> ORGANISM: Pantoea ananatis

<400> SEQUENCE: 119

```
atggaactcg aatacgaaag taaacgcccg ctatatattc cttatgctgg ccctatattg      60
ctggaatttc cgctgctgaa taaaggcagt gccttcagca tcgaagagcg caatgaattt     120
aacctcaatg gcttactgcc agaagcggta gaatccatcg aagagcaggc aaaacgcgca     180
tggcgtcagt ttcaggactt caaaaacaac aacgataaac atgtctacct gcgcaacatt     240
caggatacca acgaaacgct gttttatcgt ctgctggaca accatctcga agagatgatg     300
ccgattattt acacgccaac cgtcggtgcc gcctgcgaac acttctcaga aatttatcgc     360
cgcgcgcgtg gcgtgttcat ctcctatccc aaccgtgcgc atcgaagaa catgctgcaa     420
aacgccacca acaaaatgt gaaagtgatt gtggtcactg acggtgagcg catccttggc     480
ctgggcgatc agggcatcgg tggcatgggc attccaatcg gtaagctgtc cctgtacacc     540
gcctgtggcg gcatcagccc cgcttatacc ctgccggtgg tgctggatgt gggcaccaat     600
aaccagcagc tgcttaacga tccgctgtac atgggctggc gccatccccg tatcacgggt     660
gaagaatatg acgagtttgt aaacgagttt attcaggccg tgaaacgccg ctggccaaaa     720
gtgctgttgc agttcgaaga ttttgcacag aaaaacgcca tgccactgct ggagcgctat     780
cgtgacgaag tgtgctgctt caatgatgac attcaggta ccgctgcggt caccgttggc     840
accctgattg ccgcgagccg tgcagcaggc agccgcctgt gcgagcagaa ggttgtcttc     900
ctgggcgcag gttcagccgg ttgtggtatt gccgaacaga tcatcgcaca gatgaaatcg     960
gaaggtctga gcgacgacga agcccgtcgt cgcgtcatga tggtggatcg ctttggtttg    1020
ctgaccgaca aactgcctaa cctgctcgat ttccagagca gctggtgca gaaaagcgac    1080
aacctgaaag actgggatac ctcaaatgat gcgatctcac tgctggacgt ggtgcgtaac    1140
gcacagccag acatcttaat cggtgtgtca ggtcagcctg ggctgttcac agaagagatc    1200
atccgtgaga tgcacaagca ctgcaaacgt ccaatcgtga tgccgctttc taacccaacg    1260
tctcgcgttg aggccacgcc ggcagacatt attgcctgga ccgatggtgc cgccctggtc    1320
gctaccggta gtccgttctc accggtttcg tggaacggta agacctaccc tatcgcgcag    1380
tgtaataact cctacatctt ccctggcatt ggcctgggcg taattgcgtc tggcgcatcg    1440
cgtgtcaccg ataccatgct gatgacggcc agccgtgctc ttgcggattg ttcaccgctg    1500
gtgaacgatg tgaaggccc ggttctgcct gaaattaaag atattcaggg cgtgtcgaag    1560
attatcgcga tggaagtggg caaagctgcc cagctcgcag gcgtcgcggt ggtgacttca    1620
gaagatgtgc tctcacagtc tatcgccaat aatttctggc tgcctcaata ccgccactac    1680
cgccgtacct ctatctaa                                                 1698
```

<210> SEQ ID NO 120
<211> LENGTH: 565
<212> TYPE: PRT
<213> ORGANISM: Pantoea ananatis

<400> SEQUENCE: 120

Met Glu Leu Glu Tyr Glu Ser Lys Arg Pro Leu Tyr Ile Pro Tyr Ala
1               5                   10                  15

Gly Pro Ile Leu Leu Glu Phe Pro Leu Leu Asn Lys Gly Ser Ala Phe
            20                  25                  30

```
Ser Ile Glu Glu Arg Asn Glu Phe Asn Leu Asn Gly Leu Leu Pro Glu
         35                  40                  45
Ala Val Glu Ser Ile Glu Glu Gln Ala Lys Arg Ala Trp Arg Gln Phe
 50                  55                  60
Gln Asp Phe Lys Asn Asn Asn Asp Lys His Val Tyr Leu Arg Asn Ile
 65                  70                  75                  80
Gln Asp Thr Asn Glu Thr Leu Phe Tyr Arg Leu Leu Asp Asn His Leu
                 85                  90                  95
Glu Glu Met Met Pro Ile Ile Tyr Thr Pro Thr Val Gly Ala Ala Cys
            100                 105                 110
Glu His Phe Ser Glu Ile Tyr Arg Arg Ala Arg Gly Val Phe Ile Ser
            115                 120                 125
Tyr Pro Asn Arg Ala His Ile Glu Asp Met Leu Gln Asn Ala Thr Lys
        130                 135                 140
Gln Asn Val Lys Val Ile Val Val Thr Asp Gly Glu Arg Ile Leu Gly
145                 150                 155                 160
Leu Gly Asp Gln Gly Ile Gly Gly Met Gly Ile Pro Ile Gly Lys Leu
                165                 170                 175
Ser Leu Tyr Thr Ala Cys Gly Gly Ile Ser Pro Ala Tyr Thr Leu Pro
            180                 185                 190
Val Val Leu Asp Val Gly Thr Asn Asn Gln Gln Leu Leu Asn Asp Pro
        195                 200                 205
Leu Tyr Met Gly Trp Arg His Pro Arg Ile Thr Gly Glu Glu Tyr Asp
    210                 215                 220
Glu Phe Val Asn Glu Phe Ile Gln Ala Val Lys Arg Arg Trp Pro Lys
225                 230                 235                 240
Val Leu Leu Gln Phe Glu Asp Phe Ala Gln Lys Asn Ala Met Pro Leu
                245                 250                 255
Leu Glu Arg Tyr Arg Asp Glu Val Cys Cys Phe Asn Asp Asp Ile Gln
            260                 265                 270
Gly Thr Ala Ala Val Thr Val Gly Thr Leu Ile Ala Ala Ser Arg Ala
        275                 280                 285
Ala Gly Ser Arg Leu Cys Glu Gln Lys Val Val Phe Leu Gly Ala Gly
    290                 295                 300
Ser Ala Gly Cys Gly Ile Ala Glu Gln Ile Ile Ala Gln Met Lys Ser
305                 310                 315                 320
Glu Gly Leu Ser Asp Asp Glu Ala Arg Arg Arg Val Met Met Val Asp
                325                 330                 335
Arg Phe Gly Leu Leu Thr Asp Lys Leu Pro Asn Leu Leu Asp Phe Gln
            340                 345                 350
Ser Lys Leu Val Gln Lys Ser Asp Asn Leu Lys Asp Trp Asp Thr Ser
        355                 360                 365
Asn Asp Ala Ile Ser Leu Leu Asp Val Val Arg Asn Ala Gln Pro Asp
    370                 375                 380
Ile Leu Ile Gly Val Ser Gly Gln Pro Gly Leu Phe Thr Glu Glu Ile
385                 390                 395                 400
Ile Arg Glu Met His Lys His Cys Lys Arg Pro Ile Val Met Pro Leu
                405                 410                 415
Ser Asn Pro Thr Ser Arg Val Glu Ala Thr Pro Ala Asp Ile Ile Ala
            420                 425                 430
Trp Thr Asp Gly Ala Ala Leu Val Ala Thr Gly Ser Pro Phe Ser Pro
        435                 440                 445
Val Ser Trp Asn Gly Lys Thr Tyr Pro Ile Ala Gln Cys Asn Asn Ser
```

```
                450             455             460
Tyr Ile Phe Pro Gly Ile Gly Leu Gly Val Ile Ala Ser Gly Ala Ser
465                 470                 475                 480

Arg Val Thr Asp Thr Met Leu Met Thr Ala Ser Arg Ala Leu Ala Asp
                485                 490                 495

Cys Ser Pro Leu Val Asn Asp Gly Glu Gly Pro Val Leu Pro Glu Ile
            500                 505                 510

Lys Asp Ile Gln Gly Val Ser Lys Ile Ile Ala Met Glu Val Gly Lys
        515                 520                 525

Ala Ala Gln Leu Ala Gly Val Ala Val Val Thr Ser Glu Asp Val Leu
    530                 535                 540

Ser Gln Ser Ile Ala Asn Asn Phe Trp Leu Pro Gln Tyr Arg His Tyr
545                 550                 555                 560

Arg Arg Thr Ser Ile
                565

<210> SEQ ID NO 121
<211> LENGTH: 2280
<212> TYPE: DNA
<213> ORGANISM: Pantoea ananatis

<400> SEQUENCE: 121
atggatgacc aactgaagca aagtgcgctc gattttcacc agtatcccac tcccggcaag    60
attcaggtct cgcccactaa accgctggcc actcagcgcg atctggccct ggcctattca   120
cccggcgtcg ccgcaccctg cttagaaatt gccgccgatc ccctggccgc cataaatac    180 actgcacgcg gtaatctggt ggcggttatt tctaacggca cggcggtgct gggcctgggc   240
aacattggtg cgctggccgg taagccggtg atggaaggca agggcgtttt atttaagaag   300
tttgccggta ttgacgtctt tgatattgag gtcgatgagc acgatcccga taagctgatc   360
gagattgtcg cggcgctgga acccaccttc ggcggtatca acctggaaga tatcaaagcg   420
ccagagtgtt tctacattga gcagcagcta cggcaacgca tgaaaatccc ggtgttccac   480
gacgatcagc acggcacggc gattatctgc acgcgcggcg gtgttaaacg gttgcgtatt   540
atcaagaagg cgatttccga cgtgcggctg gtggtctccg cgcgggcgc tcggcgatt    600 gcctgcatga atctgctggt cgcgttgggt ttgcagaagc acaatattca ggtgtgcgat   660 tcaaagggc tgatctaccg tgggcgcgag cccaatatgg cggagaccaa ggccgactat   720
gcggttgagg atcagggaaa acgtacgctg gccgaggtta ttgagggcgc cgacattttt   780
ctgggctgct ctggcccgga tgtcctgacg cctgacatgg tcaaaaccat ggccagcgat   840
ccgctgattc tggcgctggc gaatccgcag ccagaaattc tgccgccgct cgctaaggcc   900
gtgcggcccg acgccattat ctgcaccggc cgttctgact atcctaatca ggtgaataac   960
gtcctgtgct ttccgtttat ctttcgggga gcgctggatg ttggcgcaac ggccatcaat  1020
gaagagatga gctggcggc ggtgcacgcg atagccgagc tggcgcaggc ggagcagagc  1080
gatgtggtgg cttcggccta tagcgatcag gacctgagct ttgccccgga atatctgatc  1140 cccaaacct tcgatccccg gttaattgtg cagatcgccc cggcggtggc gaaggcggcg  1200
atggattccg tgtggcgac ccggcccatt agcgacttcg acgcctatcg cgaacagctc  1260
acggaattcg tctataaaac caatctgttt atgaaaccga ttttctctca ggcgcgcaaa  1320
gcgccgaagc gcgtggtgct ggcagagggg gaagaggttc gggtgctgca tgcgacgcag  1380
gaattagtgt cgttggggct ggcaaaacct gttttgatag gccgcccgaa cgttatcgcg  1440
```

-continued

```
atgcgccttg aaaagcaggg gctgaagatc gaagccggaa aggatttcga atcgtcaac    1500 aacgaatccg atccccgttt taaagcatac tggaacgagt attaccagat gatgaagcgg   1560
cgcggcgtaa cgcccgagca ggcacagcgc gcggtgatcg gtaatccgac gctcattggg   1620
gccatcatgg tctatcgcgg tgaagcggat gcgctcatct gcggcaccat cggggattac   1680
aacgagcact acgagattgt ggagaaagtg ctgggcctgc gttccgatgt gaaagtggca   1740
ggggccatga atgccttgct gctgccgcac ggcaacacct ttattgcgga tacctacgta   1800
aatgaagatc ccacacccga gcagttagcg gacatcacgt taatggcggc cgaaaccgtg   1860
cggcgatttg gtattgaacc gcgggttgcc ctgctgtcgc actccagctt tggcacctca   1920
aattctcctg gcgctcgaaa aatgcgtgac gtactggcgc tggtgcagca gcgcgcacct   1980
gagctggaaa ttgacggcga gatgcacggc gatgcggcac tggtagagag cattcgtcgg   2040
gagatcatgc ccgacagccc gctgaaaggc agcgccaacc tgttgattat gcccaacgtg   2100
gaggcggcac gaatcagcta aacctgctg cgcgtctcgc acgctgacgg cgtgacggtg    2160
gggccggtgc tgatggggat gaccaaaccc gtgcacgtac tcacccgcat cgcctccgtg   2220
cggcgcatcg ttaatatggg ggcgctggcg gtggtagaag cacaaaccca gccgctgtaa   2280
```

<210> SEQ ID NO 122
<211> LENGTH: 759
<212> TYPE: PRT
<213> ORGANISM: Pantoea ananatis

<400> SEQUENCE: 122

```
Met Asp Asp Gln Leu Lys Gln Ser Ala Leu Asp Phe His Gln Tyr Pro
1               5                   10                  15

Thr Pro Gly Lys Ile Gln Val Ser Pro Thr Lys Pro Leu Ala Thr Gln
            20                  25                  30

Arg Asp Leu Ala Leu Ala Tyr Ser Pro Gly Val Ala Ala Pro Cys Leu
        35                  40                  45

Glu Ile Ala Ala Asp Pro Leu Ala Ala His Lys Tyr Thr Ala Arg Gly
    50                  55                  60

Asn Leu Val Ala Val Ile Ser Asn Gly Thr Ala Val Leu Gly Leu Gly
65                  70                  75                  80

Asn Ile Gly Ala Leu Ala Gly Lys Pro Val Met Glu Gly Lys Gly Val
                85                  90                  95

Leu Phe Lys Lys Phe Ala Gly Ile Asp Val Phe Asp Ile Glu Val Asp
            100                 105                 110

Glu His Asp Pro Asp Lys Leu Ile Glu Ile Val Ala Ala Leu Glu Pro
        115                 120                 125

Thr Phe Gly Gly Ile Asn Leu Glu Asp Ile Lys Ala Pro Glu Cys Phe
    130                 135                 140

Tyr Ile Glu Gln Gln Leu Arg Gln Arg Met Lys Ile Pro Val Phe His
145                 150                 155                 160

Asp Asp Gln His Gly Thr Ala Ile Ile Cys Thr Ala Ala Val Leu Asn
                165                 170                 175

Gly Leu Arg Ile Ile Lys Lys Ala Ile Ser Asp Val Arg Leu Val Val
            180                 185                 190

Ser Gly Ala Gly Ala Ser Ala Ile Ala Cys Met Asn Leu Leu Val Ala
        195                 200                 205

Leu Gly Leu Gln Lys His Asn Ile Gln Val Cys Asp Ser Lys Gly Leu
    210                 215                 220

Ile Tyr Arg Gly Arg Glu Pro Asn Met Ala Glu Thr Lys Ala Asp Tyr
```

-continued

```
            225                 230                 235                 240

Ala Val Glu Asp Gln Gly Lys Arg Thr Leu Ala Glu Val Ile Glu Gly
                245                 250                 255

Ala Asp Ile Phe Leu Gly Cys Ser Gly Pro Asp Val Leu Thr Pro Asp
                260                 265                 270

Met Val Lys Thr Met Ala Ser Asp Pro Leu Ile Leu Ala Leu Ala Asn
                275                 280                 285

Pro Gln Pro Glu Ile Leu Pro Pro Leu Ala Lys Ala Val Arg Pro Asp
                290                 295                 300

Ala Ile Ile Cys Thr Gly Arg Ser Asp Tyr Pro Asn Gln Val Asn Asn
305                 310                 315                 320

Val Leu Cys Phe Pro Phe Ile Phe Arg Gly Ala Leu Asp Val Gly Ala
                325                 330                 335

Thr Ala Ile Asn Glu Glu Met Lys Leu Ala Ala Val His Ala Ile Ala
                340                 345                 350

Glu Leu Ala Gln Ala Glu Gln Ser Asp Val Val Ala Ser Ala Tyr Ser
                355                 360                 365

Asp Gln Asp Leu Ser Phe Gly Pro Glu Tyr Leu Ile Pro Lys Pro Phe
                370                 375                 380

Asp Pro Arg Leu Ile Val Gln Ile Ala Pro Ala Val Ala Lys Ala Ala
385                 390                 395                 400

Met Asp Ser Gly Val Ala Thr Arg Pro Ile Ser Asp Phe Asp Ala Tyr
                405                 410                 415

Arg Glu Gln Leu Thr Glu Phe Val Tyr Lys Thr Asn Leu Phe Met Lys
                420                 425                 430

Pro Ile Phe Ser Gln Ala Arg Lys Ala Pro Lys Arg Val Val Leu Ala
                435                 440                 445

Glu Gly Glu Glu Val Arg Val Leu His Ala Thr Gln Glu Leu Val Ser
                450                 455                 460

Leu Gly Leu Ala Lys Pro Val Leu Ile Gly Arg Pro Asn Val Ile Ala
465                 470                 475                 480

Met Arg Leu Glu Lys Gln Gly Leu Lys Ile Glu Ala Gly Lys Asp Phe
                485                 490                 495

Glu Ile Val Asn Asn Glu Ser Asp Pro Arg Phe Lys Ala Tyr Trp Asn
                500                 505                 510

Glu Tyr Tyr Gln Met Met Lys Arg Arg Gly Val Thr Pro Glu Gln Ala
                515                 520                 525

Gln Arg Ala Val Ile Gly Asn Pro Thr Leu Ile Gly Ala Ile Met Val
                530                 535                 540

Tyr Arg Gly Glu Ala Asp Ala Leu Ile Cys Gly Thr Ile Gly Asp Tyr
545                 550                 555                 560

Asn Glu His Tyr Glu Ile Val Glu Lys Val Leu Gly Leu Arg Ser Asp
                565                 570                 575

Val Lys Val Ala Gly Ala Met Asn Ala Leu Leu Leu Pro His Gly Asn
                580                 585                 590

Thr Phe Ile Ala Asp Thr Tyr Val Asn Glu Asp Pro Thr Pro Glu Gln
                595                 600                 605

Leu Ala Asp Ile Thr Leu Met Ala Ala Glu Thr Val Arg Arg Phe Gly
                610                 615                 620

Ile Glu Pro Arg Val Ala Leu Leu Ser His Ser Ser Phe Gly Thr Ser
625                 630                 635                 640

Asn Ser Pro Gly Ala Arg Lys Met Arg Asp Val Leu Ala Leu Val Gln
                645                 650                 655
```

```
Gln Arg Ala Pro Glu Leu Glu Ile Asp Gly Glu Met His Gly Asp Ala
             660                 665                 670

Ala Leu Val Glu Ser Ile Arg Arg Glu Ile Met Pro Asp Ser Pro Leu
         675                 680                 685

Lys Gly Ser Ala Asn Leu Leu Ile Met Pro Asn Val Glu Ala Ala Arg
     690                 695                 700

Ile Ser Tyr Asn Leu Leu Arg Val Ser His Ala Asp Gly Val Thr Val
705                 710                 715                 720

Gly Pro Val Leu Met Gly Met Thr Lys Pro Val His Val Leu Thr Arg
                 725                 730                 735

Ile Ala Ser Val Arg Arg Ile Val Asn Met Val Ala Leu Ala Val Val
             740                 745                 750

Glu Ala Gln Thr Gln Pro Leu
         755

<210> SEQ ID NO 123
<211> LENGTH: 1599
<212> TYPE: DNA
<213> ORGANISM: Pantoea ananatis

<400> SEQUENCE: 123
atgacagact cggttatcaa cagtgaatta cttttcagta aacccttag cgatgcggaa       60
aagcagttgc ttactcccga cgccatcgct tttctgcagg aactggtgac gcgttttgca     120
ccccagcgtg agagattgtt agccgcacgt caggtccggc aaaaagagta cgattccggc     180
gggttacctg actttgatat ggaaacggtt ccataagag agcgagcgtg gacgatccgt      240
ggtattccgg ccgatttaca ggatcgtcgc gttgagatca ccgtccgcc cgatcgcaaa     300
atggtgatta cgccttgaa tgctaacgta aaggtgttta tggccgactt tgaggactcg     360
ctggcacctt gctgggaaaa actcattgac ggacagcaaa ccttacggga agccgtggcg     420
ggaacgctgc gctataccag cgagaacgga aaaatctatc agctacgggc cgatcctgcg     480
gtattgatgt gccgggtacg tggactgcat ctgtctgaaa acatgttag ctggcagggc      540
aatgcgattc ccgtggtct gttcgatttt gctctctact tttttcataa cgcggaagcc     600
ttactggcaa aaggcagtgg cccctatttt tatctgccta aaactgagag ctggcaggaa     660
gttgcgtggt ggcgggatat ctttagcttt gccgaggatc gttttgatct ggctcgcggc     720
accataaaag ccaccgtatt gatcgaaacg ctaccggcgg tattccagat gaacgagatc     780
ctgtggaatc tgcgggatca tatcgtgggg ctgaactgcg gccgctggga ttatatttc     840
agctatatca aaacgctgcg cgaacatgcc gatcggattc tgcccgaccg gcagtctgta     900
accatggctc agccctttct ggatgcttac tcacgactgc tgatccaaac ctgccatcgc     960
cgcggtgctt ttgccatggg cggcatgtca gcactgatac ccagcaagga cagcgcgcgc    1020
aatgaatggg tgctgcagcg cgtcactgaa gataaacagc gtgaagccaa caacggacat    1080
gacggtacct ggatagcgca tcccggcctg cagacactg cgatgtcagt cttcaaccag     1140
gtactgggtg aacgccccaa tcagctcaac attctgcggc aggatgacag cccgataacg    1200
gcagagcagc ttctggcacc ttgcgaaggc gatcgaacgg aagcgggcat gcgcgccaat    1260
attcgggtgg cgttgcagta tctggaagcc tggattagcg gcaatggctg tgtccccatc    1320
gatggcctga tggaagatgc cgcaactgca gaaattgccc ggacttcaat ctggcaatgg    1380
atccgccatc agaaatctct gctcgatgga cagccggtca cggccgcgct cttccagcag    1440
ctgctgaacg atgagctgca aacgctacag atgcatctgg gcgataagac attcagttca    1500
```

```
ggtcgttatg aggaagcggc gcgcctgatg gcgcagatca caactcagga cgaactggtt    1560
tcctttctga ctctgccagg ctaccgcctg cttccctga                            1599
```

<210> SEQ ID NO 124
<211> LENGTH: 532
<212> TYPE: PRT
<213> ORGANISM: Pantoea ananatis

<400> SEQUENCE: 124

```
Met Thr Asp Ser Val Ile Asn Ser Glu Leu Leu Phe Ser Lys Pro Phe
1               5                   10                  15

Ser Asp Ala Glu Lys Gln Leu Leu Thr Pro Asp Ala Ile Ala Phe Leu
            20                  25                  30

Gln Glu Leu Val Thr Arg Phe Ala Pro Gln Arg Glu Arg Leu Leu Ala
        35                  40                  45

Ala Arg Gln Val Arg Gln Lys Glu Tyr Asp Ser Gly Gly Leu Pro Asp
    50                  55                  60

Phe Asp Met Glu Thr Val Ser Ile Arg Glu Arg Ala Trp Thr Ile Arg
65                  70                  75                  80

Gly Ile Pro Ala Asp Leu Gln Asp Arg Arg Val Glu Ile Thr Gly Pro
                85                  90                  95

Pro Asp Arg Lys Met Val Ile Asn Ala Leu Asn Ala Asn Val Lys Val
            100                 105                 110

Phe Met Ala Asp Phe Glu Asp Ser Leu Ala Pro Cys Trp Glu Lys Leu
        115                 120                 125

Ile Asp Gly Gln Gln Thr Leu Arg Glu Ala Val Ala Gly Thr Leu Arg
    130                 135                 140

Tyr Thr Ser Glu Asn Gly Lys Ile Tyr Gln Leu Arg Ala Asp Pro Ala
145                 150                 155                 160

Val Leu Met Cys Arg Val Arg Gly Leu His Leu Ser Glu Lys His Val
                165                 170                 175

Ser Trp Gln Gly Asn Ala Ile Pro Gly Gly Leu Phe Asp Phe Ala Leu
            180                 185                 190

Tyr Phe Phe His Asn Ala Glu Ala Leu Leu Ala Lys Gly Ser Gly Pro
        195                 200                 205

Tyr Phe Tyr Leu Pro Lys Thr Glu Ser Trp Gln Glu Val Ala Trp Trp
    210                 215                 220

Arg Asp Ile Phe Ser Phe Ala Glu Asp Arg Phe Asp Leu Ala Arg Gly
225                 230                 235                 240

Thr Ile Lys Ala Thr Val Leu Ile Glu Thr Leu Pro Ala Val Phe Gln
                245                 250                 255

Met Asn Glu Ile Leu Trp Asn Leu Arg Asp His Ile Val Gly Leu Asn
            260                 265                 270

Cys Gly Arg Trp Asp Tyr Ile Phe Ser Tyr Ile Lys Thr Leu Arg Glu
        275                 280                 285

His Ala Asp Arg Ile Leu Pro Asp Arg Gln Ser Val Thr Met Ala Gln
    290                 295                 300

Pro Phe Leu Asp Ala Tyr Ser Arg Leu Leu Ile Gln Thr Cys His Arg
305                 310                 315                 320

Arg Gly Ala Phe Ala Met Gly Gly Met Ser Ala Leu Ile Pro Ser Lys
                325                 330                 335

Asp Ser Ala Arg Asn Glu Trp Val Leu Gln Arg Val Thr Glu Asp Lys
            340                 345                 350
```

Gln Arg Glu Ala Asn Asn Gly His Asp Gly Thr Trp Ile Ala His Pro
            355                 360                 365

Gly Leu Ala Asp Thr Ala Met Ser Val Phe Asn Gln Val Leu Gly Glu
        370                 375                 380

Arg Pro Asn Gln Leu Asn Ile Leu Arg Gln Asp Asp Ser Pro Ile Thr
385                 390                 395                 400

Ala Glu Gln Leu Leu Ala Pro Cys Glu Gly Asp Arg Thr Glu Ala Gly
                405                 410                 415

Met Arg Ala Asn Ile Arg Val Ala Leu Gln Tyr Leu Glu Ala Trp Ile
            420                 425                 430

Ser Gly Asn Gly Cys Val Pro Ile Asp Gly Leu Met Glu Asp Ala Ala
        435                 440                 445

Thr Ala Glu Ile Ala Arg Thr Ser Ile Trp Gln Trp Ile Arg His Gln
    450                 455                 460

Lys Ser Leu Leu Asp Gly Gln Pro Val Thr Ala Ala Leu Phe Gln Gln
465                 470                 475                 480

Leu Leu Asn Asp Glu Leu Gln Thr Leu Gln Met His Leu Gly Asp Lys
                485                 490                 495

Thr Phe Ser Ser Gly Arg Tyr Glu Glu Ala Ala Arg Leu Met Ala Gln
            500                 505                 510

Ile Thr Thr Gln Asp Glu Leu Val Ser Phe Leu Thr Leu Pro Gly Tyr
        515                 520                 525

Arg Leu Leu Pro
    530

<210> SEQ ID NO 125
<211> LENGTH: 1302
<212> TYPE: DNA
<213> ORGANISM: Pantoea ananatis

<400> SEQUENCE: 125

```
atgacacgta ctcaacatat tcagcaactt gaaaaacagt ggcaggacgc gcgctggcag      60
ggcattaccc gcccgtacag cgcagaggaa gtgattaacc tgcggggctc tgttgtgccg     120
gcctgtactc tggcagagcg gggggcggtg aagctctggt cgctgctcaa tggcgacgcc     180
aaaaaaggct atatcaacag tctgggagca ttaacgggcg gtcaggctct gcaacaggca     240
aaggccggta tagaagcgat ctacctgtct ggctggcagg tcgctgccga tgccaacgta     300
gcagggcaaa tgtatccgga tcagtcgctt tatccggtca actccgtgcc tgaggtggtc     360
acccgtatta atcagacatt ccagcgcgcc gatcagattc agtgggctaa cggcacagaa     420
ccggggaca gccgctatat cgactatttt ctgcctatag tcgccgatgc agaagcgggc     480
tttggtggcg tgctgaatgc gtttgaactg atgaagtcat tgatcagcgc aggcgcggcg     540
gccgtgcact ttgaagatca actggcggcg gtgaagaaat gcggtcatat gggcggtaag     600
gtgctggtgc aacccagga ggcgatacag aagctggtgg cggcgcgtct ggctgccgat     660
gtcatgggcg tacccacgat cctgctggcg cggaccgatg cggatgccgc agacctgatc     720
acgtctgact gtgacgaata cgaccgccca tttatacgcg gcgaccgcac ggcggaaggt     780
ttcttccgca ccaacgccgg cattgagcag gcaatcagcc gtggactggc ttacgcccct     840
tacgccgatg tcctttggtg tgaaacctcc accccggatt tggccatggc ccagcgtttt     900
gccgatgcga ttcacgcccg ctatccaggc aagctgctgg cttacaactg ttcgccttcg     960
tttaactgga aaaagaatct ggatgacaaa accattgctg ccttccagca ggcgctcagt    1020
gacatgggct atcgctttca gttcattacg ctggcgggca tccacagcat gtggttcaac    1080
```

```
atgttcgatc ttgcgcacgc ttacgctcag ggcgaaggca tgcgccacta tgtggaaaaa   1140
gttcagcagc cggagtttgc tgcgcgcgaa cggggttaca gcttttcatc gcatcagcag   1200
gaggtcggaa caggctattt cgatcaggtg accaacacga ttcagggcgg caagtcatcg   1260
gtgacggccc tgacagggtc caccgaggag catcagtttt ga                     1302
```

<210> SEQ ID NO 126
<211> LENGTH: 433
<212> TYPE: PRT
<213> ORGANISM: Pantoea ananatis

<400> SEQUENCE: 126

```
Met Thr Arg Thr Gln His Ile Gln Gln Leu Glu Lys Gln Trp Gln Asp
1               5                   10                  15

Ala Arg Trp Gln Gly Ile Thr Arg Pro Tyr Ser Ala Glu Glu Val Ile
            20                  25                  30

Asn Leu Arg Gly Ser Val Val Pro Ala Cys Thr Leu Ala Glu Arg Gly
        35                  40                  45

Ala Val Lys Leu Trp Ser Leu Leu Asn Gly Asp Ala Lys Lys Gly Tyr
    50                  55                  60

Ile Asn Ser Leu Gly Ala Leu Thr Gly Gly Gln Ala Leu Gln Gln Ala
65                  70                  75                  80

Lys Ala Gly Ile Glu Ala Ile Tyr Leu Ser Gly Trp Gln Val Ala Ala
                85                  90                  95

Asp Ala Asn Val Ala Gly Gln Met Tyr Pro Asp Gln Ser Leu Tyr Pro
            100                 105                 110

Val Asn Ser Val Pro Glu Val Val Thr Arg Ile Asn Gln Thr Phe Gln
        115                 120                 125

Arg Ala Asp Gln Ile Gln Trp Ala Asn Gly Thr Glu Pro Gly Asp Ser
    130                 135                 140

Arg Tyr Ile Asp Tyr Phe Leu Pro Ile Val Ala Asp Ala Glu Ala Gly
145                 150                 155                 160

Phe Gly Gly Val Leu Asn Ala Phe Glu Leu Met Lys Ser Leu Ile Ser
                165                 170                 175

Ala Gly Ala Ala Ala Val His Phe Glu Asp Gln Leu Ala Ala Val Lys
            180                 185                 190

Lys Cys Gly His Met Gly Gly Lys Val Leu Val Pro Thr Gln Glu Ala
        195                 200                 205

Ile Gln Lys Leu Val Ala Ala Arg Leu Ala Ala Asp Val Met Gly Val
    210                 215                 220

Pro Thr Ile Leu Leu Ala Arg Thr Asp Ala Asp Ala Ala Asp Leu Ile
225                 230                 235                 240

Thr Ser Asp Cys Asp Glu Tyr Asp Arg Pro Phe Ile Arg Gly Asp Arg
                245                 250                 255

Thr Ala Glu Gly Phe Phe Arg Thr Asn Ala Gly Ile Glu Gln Ala Ile
            260                 265                 270

Ser Arg Gly Leu Ala Tyr Ala Pro Tyr Ala Asp Val Leu Trp Cys Glu
        275                 280                 285

Thr Ser Thr Pro Asp Leu Ala Met Ala Gln Arg Phe Ala Asp Ala Ile
    290                 295                 300

His Ala Arg Tyr Pro Gly Lys Leu Leu Ala Tyr Asn Cys Ser Pro Ser
305                 310                 315                 320

Phe Asn Trp Lys Lys Asn Leu Asp Asp Lys Thr Ile Ala Ala Phe Gln
                325                 330                 335
```

```
Gln Ala Leu Ser Asp Met Gly Tyr Arg Phe Gln Phe Ile Thr Leu Ala
            340                 345                 350
Gly Ile His Ser Met Trp Phe Asn Met Phe Asp Leu Ala His Ala Tyr
        355                 360                 365
Ala Gln Gly Glu Gly Met Arg His Tyr Val Lys Val Gln Gln Pro
370                 375                 380
Glu Phe Ala Ala Arg Glu Arg Gly Tyr Ser Phe Ser Ser His Gln Gln
385                 390                 395                 400
Glu Val Gly Thr Gly Tyr Phe Asp Gln Val Thr Asn Thr Ile Gln Gly
                405                 410                 415
Gly Lys Ser Ser Val Thr Ala Leu Thr Gly Ser Thr Glu Glu His Gln
            420                 425                 430
Phe

<210> SEQ ID NO 127
<211> LENGTH: 1806
<212> TYPE: DNA
<213> ORGANISM: Pantoea ananatis

<400> SEQUENCE: 127
atgccgccac gcgaatcact gattgctcac accattctgc agggttttga cgcgcagtat      60
ggtcgttttc tcgacattac cgcaggcgca aacagcgtt ttgaacaggc cgaatggcag      120
gcggtacagc aggcgatgaa ggcgcgtatt catctttacg atcatcacgt ggcattagtc      180
gccgatcaat tgcgcgtgct gaacggggcg gcacactggg acgatgactt ttggctgacg      240
attaaaagcc attacgaaac cctgttgccc ggctatccgc gctacgaaat tgccgagagc      300
ttctttaatt cggtgtactg ccggttgcat ggccataatg cactgcagcc gaaacgcctg      360 tttatttca gctctcagcc agcctcaacg caaacttccc ctgcgcgccc tctggcgcgg      420
acctatctgc cacatcaggg ctggcaagcc ctgttccatc aggtactgcg cgacctgcct      480
ttaacgctgc catggcagga tcgggcgcgc gatgaagcgt ggattcaccg ccatttgcgc      540
gagcagtttt ccgccgccca gttggagcag ggctggctgg acgtgtgcag tgagctgttt      600
tttcgcaaca aaaccgcctg gattgttgcc cggctgcacc tgcccgacgg catatttccc      660
tgtctgttgc cgattcagcg cagcgataag ggcgaactgt ggattgatac ctgcctcacg      720
gacgtcaatg acgcgagcat cgtgtttggc tttgcccgcg cttatttcat ggtctatgcg      780
ccgctgccgg cggcgctggt ggcctggctc aagcctgtat tgccgggtaa aaccctggca      840
gagcgctata tggctatcgg ctgtcaaaaa catggcaaaa cggaaagcta tcgggaatat      900
ctccaggcgc tggcgcaaac cgacgccgcg tttgagattg caccgggtat tcgtggcatg      960
gtgatgctgc tgttcacatt accgggcttt gatcgggtat ttaaagtcat caagatcgg      1020 tttgcaccgc aaaaagaggt cacagaaatg caggtcaggg cctgttatca gcaggtcaaa      1080
gagcacgacc gcgtggggcg catggccgat acacaggctt ttgaacagtt tgcgttgccg      1140
ctcgcgcgta tcgctcccgc gctactggag gaatttcaac acacgattgc cggaaagata      1200
cgtattgagg gcgatcgcct gatcatcagc cacctctggc tggaacgtcg gatgcagccc      1260
ctgaatcttt acctggcgca ggccagtgaa accagcgcc agcacgccat gaagagtat      1320 ggcaatgcga tcaaacagct ggctgcggcc aacatctttc ccggcgacat gctgtttaaa      1380
aactttggca tcacccgaca cgggcgcgtc gtgttttatg attacgatga atccgccct      1440 atgcaggaac tcaattttcg tgaggttcct caggcgcgat atgaagaaga tgagctcagt      1500
```

```
gcggagccct ggtacagcgt ggggccggat gacgtatttc ctgaaacctt ccgctatgca   1560
ttatgcagcg agcctgccat aggcgcgcta ctgcaacagc ggcatccgga aattttgag    1620 gctagctggt ggcgtgcaca acagcagcgc atcgctcagg ggcatattga ggacgtgatc   1680
gcctggcagc atgcccagcg tttctgcatc cgttacggca gcacgttgac gacgtcgtca   1740
cgtgtgcctg ctactgcagg cattcagccg tccgttttg ccagcggcca tgaatcaaac    1800
agataa                                                              1806
```

<210> SEQ ID NO 128
<211> LENGTH: 601
<212> TYPE: PRT
<213> ORGANISM: Pantoea ananatis

<400> SEQUENCE: 128

```
Met Pro Pro Arg Glu Ser Leu Ile Ala His Thr Ile Leu Gln Gly Phe
1               5                   10                  15

Asp Ala Gln Tyr Gly Arg Phe Leu Asp Ile Thr Ala Gly Ala Gln Gln
            20                  25                  30

Arg Phe Glu Gln Ala Glu Trp Gln Ala Val Gln Gln Ala Met Lys Ala
        35                  40                  45

Arg Ile His Leu Tyr Asp His His Val Ala Leu Val Ala Asp Gln Leu
    50                  55                  60

Arg Val Leu Asn Gly Ala Ala His Trp Asp Asp Asp Phe Trp Leu Thr
65                  70                  75                  80

Ile Lys Ser His Tyr Glu Thr Leu Leu Pro Gly Tyr Pro Arg Tyr Glu
                85                  90                  95

Ile Ala Glu Ser Phe Phe Asn Ser Val Tyr Cys Arg Leu His Gly His
            100                 105                 110

Asn Ala Leu Gln Pro Lys Arg Leu Phe Ile Phe Ser Ser Gln Pro Ala
        115                 120                 125

Ser Thr Gln Thr Ser Pro Ala Arg Pro Leu Ala Arg Thr Tyr Leu Pro
    130                 135                 140

His Gln Gly Trp Gln Ala Leu Phe His Gln Val Leu Arg Asp Leu Pro
145                 150                 155                 160

Leu Thr Leu Pro Trp Gln Asp Arg Ala Arg Asp Glu Ala Trp Ile His
                165                 170                 175

Arg His Leu Arg Glu Gln Phe Ser Ala Ala Gln Leu Glu Gln Gly Trp
            180                 185                 190

Leu Asp Val Cys Ser Glu Leu Phe Phe Arg Asn Lys Thr Ala Trp Ile
        195                 200                 205

Val Ala Arg Leu His Leu Pro Asp Gly Ile Phe Pro Cys Leu Leu Pro
    210                 215                 220

Ile Gln Arg Ser Asp Lys Gly Glu Leu Trp Ile Asp Thr Cys Leu Thr
225                 230                 235                 240

Asp Val Asn Asp Ala Ser Ile Val Phe Gly Phe Ala Arg Ala Tyr Phe
                245                 250                 255

Met Val Tyr Ala Pro Leu Pro Ala Ala Leu Val Ala Trp Leu Lys Pro
            260                 265                 270

Val Leu Pro Gly Lys Thr Leu Ala Glu Arg Tyr Met Ala Ile Gly Cys
        275                 280                 285

Gln Lys His Gly Lys Thr Glu Ser Tyr Arg Gly Tyr Leu Gln Ala Leu
    290                 295                 300

Ala Gln Thr Asp Ala Ala Phe Glu Ile Ala Pro Gly Ile Arg Gly Met
305                 310                 315                 320
```

```
Val Met Leu Val Phe Thr Leu Pro Gly Phe Asp Arg Val Phe Lys Val
                325                 330                 335

Ile Lys Asp Arg Phe Ala Pro Gln Lys Glu Val Thr Glu Met Gln Val
            340                 345                 350

Arg Ala Cys Tyr Gln Gln Val Lys Glu His Asp Arg Val Gly Arg Met
        355                 360                 365

Ala Asp Thr Gln Ala Phe Glu Gln Phe Ala Leu Pro Leu Ala Arg Ile
    370                 375                 380

Ala Pro Ala Leu Leu Glu Glu Phe Gln His Thr Ile Ala Gly Lys Ile
385                 390                 395                 400

Arg Ile Glu Gly Asp Arg Leu Ile Ile Ser His Leu Trp Leu Glu Arg
                405                 410                 415

Arg Met Gln Pro Leu Asn Leu Tyr Leu Ala Gln Ala Ser Glu Asn Gln
            420                 425                 430

Arg Gln His Ala Ile Glu Glu Tyr Gly Asn Ala Ile Lys Gln Leu Ala
        435                 440                 445

Ala Ala Asn Ile Phe Pro Gly Asp Met Leu Phe Lys Asn Phe Gly Ile
    450                 455                 460

Thr Arg His Gly Arg Val Val Phe Tyr Asp Tyr Asp Glu Ile Arg Pro
465                 470                 475                 480

Met Gln Glu Leu Asn Phe Arg Glu Val Pro Gln Ala Arg Tyr Glu Glu
                485                 490                 495

Asp Glu Leu Ser Ala Glu Pro Trp Tyr Ser Val Gly Pro Asp Asp Val
            500                 505                 510

Phe Pro Glu Thr Phe Arg Tyr Ala Leu Cys Ser Glu Pro Ala Ile Gly
        515                 520                 525

Ala Leu Leu Gln Gln Arg His Pro Glu Ile Phe Glu Ala Ser Trp Trp
    530                 535                 540

Arg Ala Gln Gln Gln Arg Ile Ala Gln Gly His Ile Glu Asp Val Ile
545                 550                 555                 560

Ala Trp Gln His Ala Gln Arg Phe Cys Ile Arg Tyr Gly Ser Thr Leu
                565                 570                 575

Thr Thr Ser Ser Arg Val Pro Ala Thr Ala Gly Ile Gly Pro Ser Val
            580                 585                 590

Phe Ala Ser Gly His Glu Ser Asn Arg
        595                 600

<210> SEQ ID NO 129
<211> LENGTH: 2808
<212> TYPE: DNA
<213> ORGANISM: Pantoea ananatis

<400> SEQUENCE: 129
atgcagaaca gcgcgatgaa gccctggctg actcctcct ggctggccgg cgcgaatcag      60
tcttacatag agcaactcta tgaggatttc ctgaccgatc ctgactctgt ggatgcagtg    120
tggcgctcga tgttccaaca gttaccaggc acgggagtga aacctgagca gttccactcc    180
gcaactcgcg aatatttccg tcgcctggcg aaagacgcat ctcgttacac ctcctcagtt    240
accgatccga caaccaactc caaacaagtg aaagtgctgc agctgattaa cgcgtttcgt    300
ttccgcggac atcaggaagc aaatctcgat ccgcttggcc tgtggaaaca ggaccgcgtt    360
gccgatctcg atcctgcctt tcacgatctg accgacgccg attttcagga aagctttaac    420
gtaggttctt ttgccattgg caaagaaacc atgaagctgg ccgatctgtt cgacgcgctg    480
```

```
aagcagacct actgtggctc gattggtgca gagtatatgc acatcaataa caccgaagag    540
aaacgctgga tccagcagcg tatcgaatcc ggtgcgagcc agacgtcatt cagtggcgaa    600
gagaaaaaag gtttcctgaa agagctgacc gcggcagaag ggctggaaaa atatctgggc    660
gcgaaattcc cgggtgcaaa acgtttctcg ctggaaggcg gtgatgcgct ggtgccgatg    720
ctgcgcgaga tgattcgtca tgcgggcaaa agcggcacac gtgaagtggt actggggatg    780
gcgcaccgtg gccgtcttaa cgtactgatt aacgtactgg gtaaaaagcc acaggatctg    840
ttcgacgaat tctccggtaa acacaaagag catctgggca ccggtgatgt gaagtatcac    900
atgggcttct cttcggatat tgaaaccgaa ggtggtctgg tgcatctggc gctggcgttt    960
aacccgtctc acctggaaat tgtcagcccg gtggtcatgg gatcggtacg tgcacgtctc   1020
gatcgtctgg ccgaaccggt cagcaataaa gtgttgccta tcaccattca cggtgatgcg   1080
gcggtgattg gtcagggcgt ggttcaggaa accctgaaca tgtctcaggc gcgcggctac   1140
gaagtgggcg gcacggtacg tatcgtcatt aacaaccagg ttggttttac cacctccaac   1200
ccgaaagatg cgcgttcaac cccgtactgt actgacatcg gcaagatggt gctggcaccg   1260 atttttccacg tcaatgctga cgatccggaa gcggtggcct ttgttacccg cctggcgctg   1320
gactatcgca acaccttcaa acgcgatgtg tttatcgatc tggtgtgcta tcgccgtcat   1380
ggtcacaacg aggcggatga gccaagtgct acccagccgt tgatgtacca gaaaatcaaa   1440
aagcatccga cgccgcgtaa aatttacgcc gatcgtctgg aaggcgaagg tgtcgcgtcg   1500
caggaagatg ccaccgagat ggtgaacctg taccgcgatg cgctcgatgc gggcgaatgc   1560
gtggtgccgg aatggcgtcc gatgagcctg cactccttca cgtggtcgcc ttatctgaac   1620
cacgaatggg atgagcctta tccggcacag gttgacatga aacgcctgaa ggaactggca   1680
ttgcgtatca gccaggtccc tgagcagatt gaagtgcagt cgcgcgtggc caagatctat   1740
aacgatcgca agctgatggc cgaaggcgag aaagcgttcg actggggcgg tgccgagaat   1800
ctggcgtacg ccacgctggt ggatgaaggt attccggttc gcctctcggg tgaagactcc   1860
ggtcgtggaa ccttcttcca tcgccacgcg gtcgtgcaca accaggctaa cggttcaacc   1920
tatacgccgc tgcaccatat tcataacagc cagggcgagt caaagtctg ggattcggtg    1980 ctgtctgaag aagcggtgct ggcgtttgaa tacggttacg ccacggctga ccgcgcgtg    2040 ctgaccatct gggaagcgca gtttggtgac tttgccaacg gtgctcaggt ggtgattgac   2100
cagttcatca gctctggcga acagaagtgg ggccgtatgt gtggcctggt gatgttgctg   2160
ccgcatggct acgaaggtca gggaccggaa cactcctctg cccgtctgga acgctatctg   2220
caactttgcg ccgagcagaa catgcaggtt tgcgtcccgt cgacgccggc tcaggtgtat   2280
cacatgctgc gccgtcaggc gctgcgcggg atgcgccgtc cgctggtggt gatgtcgccg   2340
aagtcgctgt tacgccatcc actggcgatc tcgtcgctgg atgaactggc aaacggcagt   2400
ttccagccgg ccattggtga gatcgacgat ctggatccgc agggcgtgaa acgcgtcgtg   2460
ctgtgctccg gtaaggttta ctacgatctg ctggaacagc gtcgtaaaga cgagaaaacc   2520
gatgttgcca tcgtgcgcat cgaacagctt tacccgttcc cgcatcaggc ggtacaggaa   2580
gcattgaaag cctattctca cgtacaggac tttgtctggt gccaggaaga gcctctgaac   2640
cagggcgcct ggtactgtag ccagcatcat ttccgtgatg tcgtgccgtt tggtgccacc   2700
ctgcgttatg caggtcgccc ggcatcggct tctccggccg tgggttatat gtccgtacac   2760
caacaacagc agcaagacct ggttaatgac gcactgaacg tcaattaa                2808
```

<210> SEQ ID NO 130
<211> LENGTH: 935
<212> TYPE: PRT
<213> ORGANISM: Pantoea ananatis

<400> SEQUENCE: 130

```
Met Gln Asn Ser Ala Met Lys Pro Trp Leu Asp Ser Trp Leu Ala
1               5                   10                  15

Gly Ala Asn Gln Ser Tyr Ile Glu Gln Leu Tyr Glu Asp Phe Leu Thr
                20                  25                  30

Asp Pro Asp Ser Val Asp Ala Val Trp Arg Ser Met Phe Gln Gln Leu
            35                  40                  45

Pro Gly Thr Gly Val Lys Pro Glu Gln Phe His Ser Ala Thr Arg Glu
50                  55                  60

Tyr Phe Arg Arg Leu Ala Lys Asp Ala Ser Arg Tyr Thr Ser Ser Val
65                  70                  75                  80

Thr Asp Pro Ala Thr Asn Ser Lys Gln Val Lys Val Leu Gln Leu Ile
                85                  90                  95

Asn Ala Phe Arg Phe Arg Gly His Gln Glu Ala Asn Leu Asp Pro Leu
                100                 105                 110

Gly Leu Trp Lys Gln Asp Arg Val Ala Asp Leu Asp Pro Ala Phe His
            115                 120                 125

Asp Leu Thr Asp Ala Asp Phe Gln Glu Ser Phe Asn Val Gly Ser Phe
130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
                165                 170                 175

Asn Thr Glu Glu Lys Arg Trp Ile Gln Gln Arg Ile Glu Ser Gly Ala
                180                 185                 190

Ser Gln Thr Ser Phe Ser Gly Glu Lys Lys Gly Phe Leu Lys Glu
            195                 200                 205

Leu Thr Ala Ala Glu Gly Leu Glu Lys Tyr Leu Gly Ala Lys Phe Pro
210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
                260                 265                 270

Leu Gly Lys Lys Pro Gln Asp Leu Phe Asp Glu Phe Ser Gly Lys His
            275                 280                 285

Lys Glu His Leu Gly Thr Gly Asp Val Lys Tyr His Met Gly Phe Ser
290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
                325                 330                 335

Arg Ala Arg Leu Asp Arg Leu Ala Glu Pro Val Ser Asn Lys Val Leu
                340                 345                 350

Pro Ile Thr Ile His Gly Asp Ala Ala Val Ile Gly Gln Gly Val Val
            355                 360                 365

Gln Glu Thr Leu Asn Met Ser Gln Ala Arg Gly Tyr Glu Val Gly Gly
370                 375                 380
```

```
Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
            405                 410                 415

Val Leu Ala Pro Ile Phe His Val Asn Ala Asp Asp Pro Glu Ala Val
            420                 425                 430

Ala Phe Val Thr Arg Leu Ala Leu Asp Tyr Arg Asn Thr Phe Lys Arg
            435                 440                 445

Asp Val Phe Ile Asp Leu Val Cys Tyr Arg Arg His Gly His Asn Glu
            450                 455                 460

Ala Asp Glu Pro Ser Ala Thr Gln Pro Leu Met Tyr Gln Lys Ile Lys
465                 470                 475                 480

Lys His Pro Thr Pro Arg Lys Ile Tyr Ala Asp Arg Leu Glu Gly Glu
            485                 490                 495

Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
            515                 520                 525

Ser Leu His Ser Phe Thr Trp Ser Pro Tyr Leu Asn His Glu Trp Asp
530                 535                 540

Glu Pro Tyr Pro Ala Gln Val Asp Met Lys Arg Leu Lys Glu Leu Ala
545                 550                 555                 560

Leu Arg Ile Ser Gln Val Pro Glu Gln Ile Glu Val Gln Ser Arg Val
            565                 570                 575

Ala Lys Ile Tyr Asn Asp Arg Lys Leu Met Ala Glu Gly Glu Lys Ala
            580                 585                 590

Phe Asp Trp Gly Gly Ala Glu Asn Leu Ala Tyr Ala Thr Leu Val Asp
            595                 600                 605

Glu Gly Ile Pro Val Arg Leu Ser Gly Glu Asp Ser Gly Arg Gly Thr
610                 615                 620

Phe Phe His Arg His Ala Val His Asn Gln Ala Asn Gly Ser Thr
625                 630                 635                 640

Tyr Thr Pro Leu His His Ile His Asn Ser Gln Gly Glu Phe Lys Val
            645                 650                 655

Trp Asp Ser Val Leu Ser Glu Glu Ala Val Leu Ala Phe Glu Tyr Gly
            660                 665                 670

Tyr Ala Thr Ala Glu Pro Arg Val Leu Thr Ile Trp Glu Ala Gln Phe
            675                 680                 685

Gly Asp Phe Ala Asn Gly Ala Gln Val Val Ile Asp Gln Phe Ile Ser
            690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
            725                 730                 735

Glu Arg Tyr Leu Gln Leu Cys Ala Glu Gln Asn Met Gln Val Cys Val
            740                 745                 750

Pro Ser Thr Pro Ala Gln Val Tyr His Met Leu Arg Arg Gln Ala Leu
            755                 760                 765

Arg Gly Met Arg Arg Pro Leu Val Val Met Ser Pro Lys Ser Leu Leu
            770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
```

```
                    805                 810                 815
Lys Arg Val Val Leu Cys Ser Gly Lys Val Tyr Tyr Asp Leu Leu Glu
                820                 825                 830

Gln Arg Arg Lys Asp Glu Lys Thr Asp Val Ala Ile Val Arg Ile Glu
                835                 840                 845

Gln Leu Tyr Pro Phe Pro His Gln Ala Val Gln Glu Ala Leu Lys Ala
    850                 855                 860

Tyr Ser His Val Gln Asp Phe Val Trp Cys Gln Glu Pro Leu Asn
865                 870                 875                 880

Gln Gly Ala Trp Tyr Cys Ser Gln His Phe Arg Asp Val Val Pro
                885                 890                 895

Phe Gly Ala Thr Leu Arg Tyr Ala Gly Arg Pro Ala Ser Ala Ser Pro
                900                 905                 910

Ala Val Gly Tyr Met Ser Val His Gln Gln Gln Gln Asp Leu Val
                915                 920                 925

Asn Asp Ala Leu Asn Val Asn
    930                 935

<210> SEQ ID NO 131
<211> LENGTH: 490
<212> TYPE: PRT
<213> ORGANISM: Aspergillus terreus

<400> SEQUENCE: 131

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
                20                  25                  30

Asp Val Leu Glu Arg Ala Lys Tyr Leu Ile Leu Asp Gly Ile Ala Cys
            35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65              70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
    115                 120                 125

Glu Gln Gly Lys Thr Ile Ser Gly Ile Asp Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Gly Leu Thr Pro Asp Ser
            180                 185                 190

Met Glu Asp Ala Leu Gly Ile Ala Cys Thr Gln Ala Cys Gly Leu Met
    195                 200                 205

Ser Ala Gln Tyr Gly Gly Met Val Lys Arg Val Gln His Gly Phe Ala
210                 215                 220

Ala Arg Asn Gly Leu Leu Gly Gly Leu Leu Ala His Gly Gly Tyr Glu
225                 230                 235                 240
```

```
Ala Met Lys Gly Val Leu Glu Arg Ser Tyr Gly Gly Phe Leu Lys Met
            245                 250                 255

Phe Thr Lys Gly Asn Gly Arg Glu Pro Pro Tyr Lys Glu Glu Glu Val
            260                 265                 270

Val Ala Gly Leu Gly Ser Phe Trp His Thr Phe Thr Ile Arg Ile Lys
            275                 280                 285

Leu Tyr Ala Cys Cys Gly Leu Val His Gly Pro Val Glu Ala Ile Glu
            290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
            325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
            355                 360                 365

Leu Leu Ser Gln Phe Ser Glu Phe Asp Asp Asn Leu Glu Arg Pro Glu
            370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
            405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
            435                 440                 445

Ala Gly Ser Val Thr Asp Glu Ser Arg Val Lys Glu Ile Glu Asp Leu
            450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
            485                 490

<210> SEQ ID NO 132
<211> LENGTH: 80
<212> TYPE: DNA
<213> ORGANISM: Artificial Sequence
<220> FEATURE:
<223> OTHER INFORMATION: primer

<400> SEQUENCE: 132
gggtggagtt caggtacaag tatcaataga gacgcggaca gcaggtactt tgaagcctgc    60 tttttttatac taagttggca                                               80

<210> SEQ ID NO 133
<211> LENGTH: 80
<212> TYPE: DNA
<213> ORGANISM: Artificial Sequence
<220> FEATURE:
<223> OTHER INFORMATION: primer

<400> SEQUENCE: 133
gcgctggcgg ttacacgcgc gggcgtttgc gatagagcca cagaccggga cgctcaagtt    60
agtataaaaa agctgaacga                                                80
```